US008580859B2

(12) United States Patent
Bassiri et al.

(10) Patent No.: US 8,580,859 B2
(45) Date of Patent: Nov. 12, 2013

(54) METHIONINE ANALOGS AND METHODS OF USING SAME

(75) Inventors: Mansour Bassiri, Novato, CA (US); Afsaneh Rahimi-Larijani, Novato, CA (US)

(73) Assignee: BioXiness Pharmaceuticals, Inc., Hercules, CA (US)

( * ) Notice: Subject to any disclaimer, the term of this patent is extended or adjusted under 35 U.S.C. 154(b) by 195 days.

(21) Appl. No.: 13/056,102

(22) PCT Filed: Jul. 31, 2009

(86) PCT No.: PCT/US2009/052474
§ 371 (c)(1),
(2), (4) Date: Apr. 29, 2011

(87) PCT Pub. No.: WO2010/014943
PCT Pub. Date: Feb. 4, 2010

(65) Prior Publication Data
US 2011/0196014 A1    Aug. 11, 2011

Related U.S. Application Data

(60) Provisional application No. 61/085,556, filed on Aug. 1, 2008.

(51) Int. Cl.
*A61K 31/13*    (2006.01)
*C07C 239/10*   (2006.01)

(52) U.S. Cl.
USPC ................................. 514/645; 564/301

(58) Field of Classification Search
USPC ................... 564/154, 301; 514/645
See application file for complete search history.

(56) References Cited

U.S. PATENT DOCUMENTS

| | | | |
|---|---|---|---|
| 2,374,807 | A | 5/1945 | Dickey et al. |
| 3,196,173 | A | 7/1965 | Willmund et al. |
| 3,519,683 | A | 7/1970 | Inouye et al. |
| 4,169,950 | A | 10/1979 | Ferguson |
| 4,182,758 | A | 1/1980 | Kamiya et al. |
| 4,469,686 | A | 9/1984 | Andrews |
| 4,524,211 | A | 6/1985 | Drauz et al. |
| 4,859,602 | A | 8/1989 | Zimmermann et al. |
| 5,430,052 | A | 7/1995 | Higashiura et al. |
| 5,760,021 | A | 6/1998 | Ebetino et al. |
| 6,004,771 | A | 12/1999 | Thornton |
| 6,403,632 | B1 | 6/2002 | Duan et al. |
| 6,605,604 | B1 | 8/2003 | Casara et al. |
| 6,878,723 | B1 | 4/2005 | Danvy et al. |
| 2002/0061840 | A1 | 5/2002 | Roques et al. |
| 2004/0197293 | A1 | 10/2004 | Mougin |
| 2005/0107447 | A1 | 5/2005 | Lynch et al. |
| 2006/0183800 | A1 | 8/2006 | Kong et al. |
| 2006/0205695 | A1 | 9/2006 | Roques et al. |
| 2006/0223855 | A1 | 10/2006 | Kong et al. |
| 2007/0134183 | A1 | 6/2007 | Galey et al. |

FOREIGN PATENT DOCUMENTS

| | | |
|---|---|---|
| DE | 27 33 658 A1 | 2/1978 |
| EP | 0 033 919 A2 | 8/1981 |
| EP | 0 033 919 A3 | 8/1981 |
| EP | 0 078 613 A1 | 5/1983 |
| EP | 0 113 429 A1 | 7/1984 |
| EP | 0 120 609 A2 | 10/1984 |
| EP | 0 120 609 A3 | 10/1984 |
| EP | 0 176 068 A2 | 4/1986 |
| EP | 0 309 421 A2 | 3/1989 |
| EP | 0 309 421 A3 | 3/1989 |
| EP | 0 318 091 A2 | 5/1989 |
| EP | 0 343 133 A1 | 11/1989 |
| EP | 0 553 427 A1 | 8/1993 |
| EP | 0 618 221 A2 | 10/1994 |
| EP | 0 708 079 A1 | 4/1996 |
| EP | 1 602 660 A1 | 12/2005 |
| FR | 1 390 191 A | 1/1965 |
| GB | 648 768 | 1/1951 |
| GB | 2 158 071 A | 11/1985 |
| JP | 54-063024 A | 5/1979 |
| JP | 62-215597 A | 9/1987 |
| JP | 02-115147 A | 4/1990 |
| JP | 4-5270 A | 1/1992 |
| JP | 4-077466 A | 3/1992 |
| JP | 9-316474 A | 12/1997 |
| JP | 2001-288078 A | 10/2001 |
| JP | 2005-281209 A | 10/2005 |
| JP | 2006-257069 A | 9/2006 |
| WO | WO-93/01936 A1 | 5/1993 |
| WO | WO-93/15610 A1 | 8/1993 |
| WO | WO-94/20508 A1 | 9/1994 |
| WO | WO-98/15525 A1 | 4/1998 |
| WO | WO-98/17672 A1 | 4/1998 |
| WO | WO-99/06340 A2 | 2/1999 |
| WO | WO-99/06340 A3 | 2/1999 |

(Continued)

OTHER PUBLICATIONS

King, Med. Chem. Principle and Practice (1994), pp. 206-208.*
Boldyrev, B.G. et al. (Dec. 1956). "Studies in the Field of Thiosulfonic Acids. I. Synthesis and Antibacterial Properties of Some Alkyl Esters of Propane-A-Thiosulfonic Acid and Butane-1-Thiosulfonic Acid," *The Journla of Genral Chemistry of the U.S.S.R.* 26(12):3739-3743. (English Translation).
Evans, D.A. et al. (1990). "The Asymmetric Synthesis of α-Amino Acids. Electrophilic Azidation of Chiral Imide Enolates, A Practical Approach to the Synthessis of (R)- and (S)-α-Azido Carboxylic Acids," *J. Amer. Chem. Soc.* 112(10):4011-4030.

(Continued)

*Primary Examiner* — Taofiq A Solola
(74) *Attorney, Agent, or Firm* — Morrison & Foerster LLP

(57) ABSTRACT

Provided are methionine analogs which may be useful for inhibiting protein synthesis, inhibiting microbial growth and/or treating infectious diseases. In some instances, the analogs exhibit bactericidal, antibacterial, anti-infective, antimicrobial, sporicidal, disinfectant, antifungal and/or antiviral properties. Also provided are methods of treatment and methods of preparation, as well as kits and unit dosages.

12 Claims, 6 Drawing Sheets

(56) References Cited

FOREIGN PATENT DOCUMENTS

| | | |
|---|---|---|
| WO | WO-99/18074 A1 | 4/1999 |
| WO | WO-99/59957 A1 | 11/1999 |
| WO | WO-00/00473 A1 | 1/2000 |
| WO | WO-00/34313 A1 | 6/2000 |
| WO | WO-00/43414 A1 | 7/2000 |
| WO | WO-00/59864 A1 | 10/2000 |
| WO | WO-00/59874 A1 | 10/2000 |
| WO | WO-00/63197 A1 | 10/2000 |
| WO | WO-01/03680 A2 | 1/2001 |
| WO | WO-01/03680 A3 | 1/2001 |
| WO | WO-01/93872 A1 | 12/2001 |
| WO | WO-02/18395 A1 | 3/2002 |
| WO | WO-02/28829 A2 | 4/2002 |
| WO | WO-02/28829 A3 | 4/2002 |
| WO | WO-02/29001 A2 | 4/2002 |
| WO | WO-02/29001 A3 | 4/2002 |
| WO | WO-02/39975 A1 | 5/2002 |
| WO | WO-02/070577 A1 | 9/2002 |
| WO | WO-03/061567 A2 | 7/2003 |
| WO | WO-03/061567 A3 | 7/2003 |
| WO | WO-2004/062601 A2 | 7/2004 |
| WO | WO-2004/062601 A3 | 7/2004 |
| WO | WO-2004/113275 A2 | 12/2004 |
| WO | WO-2004/113275 A3 | 12/2004 |
| WO | WO-2005/020973 A2 | 3/2005 |
| WO | WO-2005/020973 A3 | 3/2005 |
| WO | WO-2006/076663 A2 | 7/2006 |
| WO | WO-2006/076663 A3 | 7/2006 |
| WO | WO-2007/069020 A2 | 6/2007 |
| WO | WO-2007/069020 A3 | 6/2007 |

OTHER PUBLICATIONS

Hayward, P. et al. (Mar. 1992). "Fibroblast Growth Factor Reverses the Bacterial Retardation of Wound Contracation," *Am J Surg* 163(3)288-293.
Hoppe, I.. et al. (1985). "Astnnetruc Addition of a Dural cyclic Phosphite to a cyclic Imine—Synthesis of thePhosphonic Acid Analogue of D- and L-Penicillamine," *Angew. Chem* 97(12):1066-1067. (English Translation with Certification.).
Khomutov, R.M. et al. (Jan. 1979). "Organophosphorus Analogs of Biologically Active Compounds," *Soviet Journal of Bioorganic Chemistry* 5(1):41-47.
Kudzin, Z.H. et al. (Mar. 2005). "1-(N-Acylamino)Alkanephosphonates. Part IV. N-Acylation of 1-Aminoalkanephosphonic Acids," *Polish Journal of Chemistry* 79(3):499-513.
Kudzin, Z.H. et al. (1989). "Long Chain 1-Aminothiaalkane-Phosphonates, Their Sulfinyl and Sulfonyl Derivates. A New Type of Complexane Type Surfactants," *Phosphorus, Sulfur and Silicon and the Related Elements* 42(1-2):41-46.
Kuhn, M.A. et al. (Mar. 1, 2001). "Basic Fibroblast Growth Factor in a Carboxymethylcellulose Vehicle Reverses the Bacterial Retardation of Wound Contraction." *Wounds* 13(2):73-80.
Kretschmar, H. et al. (1977). "Untersuchung uber die Wirsamkeit von Konservierungsmitteln in einer 0/W-Emulsion nach Mikrobieler Kontamination," *Pharmazie* 32:781-784. (English Translation with Certification.).
Lazrek, H.B. et al. (1994). "Synthesis of the Nucleotide Analog: (R,S)-9-[1-(2- Hydroxyethylthio)-2-Phosphonylethyl] Adenine," *Nucleosides & Nucleotides* 13(1-3):811-817.
McGregor, D.P. et al. (1996). "Stmulaneous Detection of Microorganisms in Soil Suspension Based on CR Amplification of Bacterial 165 rRNA Fragments," *Biotechniques* 21(3):463, 464, 466, 468, 470-471.
Mizyukova, I.G. et al. (1973). "Interrelation Between the Structure and Detoxifying Action of Some Thiols and Amines During Hexachlorobutadiene Poisoning," 5:22-24. (English Translation with Certification.).
Osipova, T.I. et al. (Nov. 1996). "Synthesis of α.-Substituted α.-Aminophosphinic and α-Aminophosphonic Acids,"*Russian Chemical Bulletin* 45(11):2588-2591.

Pu, Y. et al. (Feb. 1, 1991). "Synthesis and Acylation of Salts of $_L$-Threonine β-Lactone: A Route to β-Lactone Antibiotics," *J. Amer. Chem. Soc.* 56(3):1280-1283.
Renau, T.E. et al. (1998). "Antimicrobial Potentiation Approaches: Targets and Inhibitors," Chapter 12 in *Section III. Cancer and Infectious Diseases*, CA, Plattner, J.J. ed., Chiron Corporation, Emeryville, CA, *Annual Reports in Medicinal Chemistry* 33:121-130.
Robson, M.C. et al. (Apr. 1974). "The Efficacy of Systemic Antibiotics in the Treatment of Granulating Wounds," *Journal of Surgical Research* 16(4):299-306.
Sagripanti, J.L. et al. (2000). "Cytotoxicity of Liquid Disinfectants," *Surg Infect* 1(1):3-14.
Syrku, V.I. et al. (1986). "Chemical Regulation of S-Adenosylmethioine-Dependent Enzymic Reactions by Organophosphorus Analogs of S-Adenosylmethionine and S-Adenosylhomocysteine," *Bio-Organic Chemistry* 12(6):839-841. (English Translation.with Certification).
Tarusova, N. B. et al. (Jul. 1978). "Phosphonate Analogs of 3'(2')-0-Acylaminoacylnucleotides," *Soviet Journal of Bioorganic Chemistry* 4(7):852-856.
Tsunoo, S. (Jan. 1, 1937). "Üon the Derivatives of Amino-Oxy Propane Sulfonic Acid," *The Journal of Biochemistry* 25(2):375-391. (Machine Translation ).
Williams, R.M. et al. (1991). "Asymmetric Syntheis of Monosubstituted and α, α-Disubstitued α-Amino Acids via Diastereoselective Glycine Enolate Alkylations," *J. Amer. Chem. Soc.* 113(24):9276-9286.
Abraham, W.R. et al. (Jun. 2002, e-pub. May 13, 2002). "Polychlorinated Biphenyl-Degrading Microbial Communities in Soils and Sediments," *Curr. Opin. Microbiol.* 5(3):246-253.
Alferov, K.V. et al. (2003). "Stable Organophosphorus Analogues of S-Adneosylmethionine and S-Methylmethionine," *Medeleev Commun* 13(6):243-244.
Alferov, K.V. et al. (Feb. 2001). "Synthesis of Phosphinic and Phosphonic Analogs of Homoserine," *Russian Chemical Bulletin , International Edition* 50(2):316-318.
Ames, B.N. et al. (Feb. 1973). "Illicit Transport: The Oligopeptide Permease," *Proc. Natl. Acad. Sci. USA* 2(70):456-458.
Atherton, F.R. et al. (1986). "Synthesis and Structure-Activity Relationships of Antibacterial Phosphonopeptides Incroporating (1-Aminoethyl)Phosphonic Acid and (Aminomethyl)Phosphonic Acid," *J. Med. Chem.* 29(1):29-40.
Baylis, E.K. et al. (1984). "1-Aminoalkylphosphonous Acids. Part 1. Isosteres of the Protein Amino Acids," *J. Chem. Soc. Perkins Trans.* 1:2845-2853.
Beilstein Registry No. 822809. (1998). "(2S,3R)-2-Amino-3-Hydroxy-15-Methyl-Hexadecane-1-Sulfonic Acid," located in Belstein Online Database, Compounds BRN 8228909, 8235571 one page.
Beilstein Registry No. 316947, 3293966, 3313610. (1935). "2-Hydroxy-3-[(R)-4- ((3R,5S,7R,8R,9S,10S,12S,13R,14S,17R)-3,7,12-Trihydroxy-10,13-Dimethyl-Hexadencahydro-Cyclopental[a]phenanthren-17-yl)-pentanoylamino]-propane-1-sulfonic acid," located in Belstein Online Database, Compounds RN: 3186947, 3293966 and 3313610, three pages.
Beilstein Registry No. 5929916, 5939234. (1987). "2-Hydroxy-3-(2-Hydroxy-1,1-dimethy-ethylamino)-Propane-1-Sulfonic Acid," located in Belstein Online Database, Compounds RN: 5929916 and 5939234, two pages.
Beilstein Registry No. 1777771, 9446010, 9439324. (2003). "3-Diethylamino-2-Hydroxy-Propane-1-Sulfonic Acid," located in Belstein Online Database, Compounds RN: 1777771, 9446010 and 9429324, three pages.
Beilstein Registry No. 3331450. (1955). "3-Benzoylamino-2-Hydroxy-Propane-1-Sulfonic Acid," located in Belstein Online Database, Compounds RN: 3331450 and 1723009, two pages.
Beilstein Registry No. 6041159. (1988). "2-Hydroxy-3-(2-Hydroxy-1,1-bis-hydroxymethyl-ethylamino)-porpane-1-Sulfonatetetrabutyl-ammounium," located in Belstein Online Database, Compound RB: 6041159, two pages.

(56) References Cited

OTHER PUBLICATIONS

Bongini, a. et al. (1996). "Efficient Synthesis of the Four Diasteremoers of Phosphothreonine From Lactaldehyde," *Tetrahedron Asymmetry* 7(5):1467-1476.
CA Accession No. 1958:82299, last visited on Feb. 1, 2010, one page.
CA Accession No. 1974:422018, last visited on Feb. 2, 2010, two pages.
CA Accession No. 1976:69922, last visited on Feb. 2, 2010, two pages.
CA Accession No. 1979:23500, last visited on Aug. 4, 2010, two pages.
CA Accession No. 1980:464519, last visited on Aug. 5, 2010, one pages.
CA Accession No. 1986:510940, last visited on Aug. 4, 2010, three pages.
CA Accession No. 1989:576772, last visited on Aug. 5, 2010, four pages.
CA Accession No. 1994:483860, last visited on Aug. 5, 2010, two pages.
CA Accession No. 1996:554200, last visited on Feb. 1, 2010, two pages.
CA Accession No. 1997:73309, last visited on Aug. 8, 2010, two pages.
Ca Accession No. 2005:284897, last visited on Aug. 5, 2010, two pages.
Cascieri, T., Jr. et al. (Mar. 1974). "New Method of Study for Peptide Transport in Bacteria," *Appl Microbiol* 27(3):457-463.
Chakravarty, P.K. et al. (1987). "An Efficient Syntheis of y-Amino Acid-Ketoalkylphosphonates From α-Amino Acids," *Tetrahedron Letters* 28(6):611-612.
Chauvel, E.N. et al. (1994). "Differential Inhibition of Aminopeptidase A and Aminopeptidase N By New B-Amino Thiols," *J. Med. Chem.* 37(18):2950-2957.
Crepin, T. et al. (2003). "Use of Analogues of Methionline and Metionyl Adenylate to Sample Conformatonal Changes During Catalysis in *Escherichia coli* Methionyl-tRna Synthetase," *J. Mol. Biol.* 332:59-72.
David, C. et al. (1999, e-pub. Nov. 11, 1999). "Investigation of Subsite Preferences in Aminopeptidase A(EC 3.4.11.7) Led to the Design of the First Highly Potent Selective Inhibitors of This Enzyme," *J. Med. Chem.* 42(25):5197-5211.
David-Basei, C. et al. (2001). "Synthesis of [3(R)-Amino-2(S)-sulfydryl-5-sulonate]- pentanoyl-(S)-3-[$^{125}$I]-iodotyrosyl-(S)-aspartic Acid: A Radiolabelled Inhibitor of Aminopeptidase A," *J. Labelled CPD. RadioPharm.* 44:89-98.
Diddens, H. et al. (1976). "On the Transport of Tripeptide Antibiotics in Bacteria," *Eur. J. Biochem.* 66:11-23.
Erdmann, K. et al. (2005). "L-Methionine Reduces oXidant Stress in Endothelial Cells: Role of Heme Oxygenase-1, Ferritin, and Nitric Oxide," *The AAPS Journal* 7(1):E195-E200.
Grant, S.K. et al. (2001). "Inhibition and Structure-Activity Studies of Methionline Hydroxamic Acid Derivatives with Bacterial Peptide Deformylase," *Bioorganic Chemistry* 29(4):211-222.
Hartman, M.C.T. et al. (Mar. 21, 2006). "Enzymatic Aminoacylation of tRNA With Unnatural Amino Acids," *Proc. Natl. Acad. Sci. USA* 103(12):4356-4361.
Hemmi, K. et al. (1982). "Studies on Phosphonic Acid Antibiotics. IV[1)] Synthesis and Antibacterial Activity of Analogs of 3-(N-Acetyl-N-hydroxyamino)-Proplyphosphonic Acid (FR-900098)," *Chem. Pharm. Bull.* 30(1):111-118.
Higashiura, K. et al. (Jan. 1, 1989). "Syntheses and Properties of Optically Active 2-Substituted taurines," *Journal of the Checmical Society Perkin Trans.*, pp. 1479-1481.
Higashiura, H. et al. (1992). "Simple Performic Acid Oxidation of Acetylthio Group to Sulfonic Acid and Its Appliation in Syntheses of 2-Substiutued Taurines," *J. Org. Chem .* 57(2):764-766.
Hudson, H.R. et al. (Jan. 1, 2001). "Organophosphorus Compounds as Potential Fungicides. Part VI.1 Preparation, Characterization, and Biological Activity of Analogues and Derivatives of 1-Aminopropanephosphonic Acid," *Phosphorus, Sulfur, and Silicon* 173(1):143-162.
Hurdle, J.G. et al. (Dec. 2005). "Prospect for Aminoacyl-tRNA Synthetase Inhibitors as New Antimicrobial Agents," *Antimicrob. Agents and Chemother.* 49(12):4821-4833.
International Search Report mailed on Nov. 25, 2010, for PCT Application No. PCT/US2009/052474, filed on Jul. 31, 2009, thirty-six pages.
Jinachitra, S. et al. (1979). "A Synthesis of α-Aminosulphonic Acids," *Tetrahedron* 35:1315-1316
Jo, J.J. et al. (Nov. 1999). "Methionine Analogue Probes Functionally Important Residues in Active Site of Methionyl-tRNA Synthestase," *Journal of Biochemistry and Molecular Biology* 32(6):547-553.
Kim, S. et al. (2003, e-pub. Mar. 1, 2003). "Aminoacyl-tRNA Synthetases and Their Inhibitors as a Novel Family of Antibiotics," *Appl. Microbiol. Biotechnol.* 61:278-288.
Kjelleberg, S. et al. (Jun. 2002, e-pub. May 13, 2002). "Is There a Role for Quorum Sensing Signals in Bacterial Biofilms?," *Curr Opin Micobiol.* 5(3):254-258.
Kudzin, Z.H. (Dec. 1980). "Phosphohomocystein Derivatives," *Synthesis* pp. 1032-1034.
Kudzin, Z.H. (Aug. 1981). "Phosphocysteine Derivates: Thloureldoslkanephosphosates Via Acetals," *Synthesis* pp. 643-645.
Kudzin, Z.H. (Oct. 1983). " Phosphonocysteine and Phosphonohomocysteine; Synthesis and Isolation," Synthesis pp. 812-814.
Kupczuk-Subotkowska , L. et al. (1983). "Synthesis of Phosphonic Analogs of Enkephalins," *Int. J. Peptide Protein Res.* 21:485-490.
Kurzak, B. et al. (2004, e-pub. Jun. 24, 2004). "Copper(II) Complexex of Several Monophosphono Dipeptides: The Role of Phosphonic Oxygen and Thioether Sulfur in Complex Stabilization,"*Polyhedron* 23:1939-1946.
Laske S. et al. (1989). "Investigations on the Antiproliferative Effects of Amino Acid Antagonist Targeting for Aminoacyl-tRNA Synthetases. Part I—The Antibacterial Effect," *Arch. Pharm.* 322:847-852.
Lee, J. et al. (1998). "Methionine Analogues as Inhibitors of Methionyl-tRNA Synthetase," *Bioor. Med. Chem. Lett.* 8:3511-3514.
Lejczak, B. et al. (1986). "Antibacterial Activity of Phosphono Dipeptides Related to Alafosfalin," *J. Med. Chem.* 29(11):2212-2217.
Levine, R. et al. (Dec. 1996). "Methionine Residues as Endogenous Antioxidants in Proteins," *Proc. Natl. Acad. Sci USA* 93:15036-15040.
Martin, L. et al. (1998). "B-Amino-Thiols Inhibit the Zinc Metallopeptidase Activity of Tetanus Toxin Light Chain," *J. Med. Chem.* 41:3450-3460.
Matczak-Jon, E. et al. (1998). "The Phosphonic Analogues of Theronine and B-Phenylserine: Preparation and Analysis of Stereoisomers," *Phosphorus, Sulfur and Silicon* 142:101-115.
Ochsner, U.A. et al. (2007). "Aminoacyl-tRNA Synthetases: Essential and Still Promising Targets for New Anti-Infective Agents," *Expert Opin. Investig. Drugs* 16(5):573-593.
Robson, M.C. et al. (Apr. 11, 2007). "Hyprochlorous Acid as a Potential Wound Care Agent. Part II Stabilized Hypochlorous Acid: Its Role in Decreasing Tissue Bacterial Bioburden and Overcoming the Inhibition of Infection on Wound Healing," *Journal of Burns and Wounds* 6(7):80-90.
Scudiero, D.A. et al. (Sep. 1, 1998). "Evaluation of a Soluble Tetrazolium/Formazan Assay for Cell Growth and Drug Sensitivity in Culture Using Human and Other Tumor Cell Lines," *Cancer Res.* 48(17):4827-4833.
Smith, M.W. et al. (1999). "Substrate Specificity of the Periplasmic Dipeptide-Binding Protein From *Escherichia coli*: Experimental Basis for the Design of Peptide Prodrugs," *Microbiology* 145:2891-2901.
Steere, J.A. et al. (2001). "Synthesis of an α-Aminophosphonate Nucleoside as an Inhibitor of S-Adenosyl-L-Homocysteine Hydrolase," *Bioorganic & Medicinal Chemistry Letters* 12:457-460.
Tam, C.C. et al. (Mar. 1982). "Synthesis of Phosphomethionine and Related Compounds," *Synthesis* pp. 188-190.

(56) References Cited

OTHER PUBLICATIONS

Tamaoku, K. et al. (1982). "New Water-Soluble Hydrogen Donors for the Enzymatic Photometric Determination of Hydrogen Peroxide. 11.[1)] N-Ethyl-N-(2-Hydroxy-3-Sulfopropyl)Aniline Derivitaves," *Chem. Parm. Bull.* 30(7):2492-2497.

Thiel, T. et al. (1998). "New Zwitterionic Putanesulfonic Acids That Extend the Alkaline Range of Four Families of Good Buffers: Evaluation for Use in Biological Systems," *J. Biochem. Biophys. Methods* 37(3):117-129.

Vaughan, M.D. et al. (2002). "Methionine in and Out of Proteins: Targets for Drug Design," *Curr. Med. Chem.* 9(3):385-409.

Vaughan, M.D. et al. (2005). "Investigation of bioisosteric Effects on the Interaction of Substrates/Inhibitors With the Methionyl-tRNA Synethetase From *Escherichia coli*," *Medicinal Chemistry* 1(3):227-237.

Wang, L. et al. (Apr. 11, 2007). "Hypochlorous Acid as a Potential Wound Care Agent," *J. Burns and Wounds* 6:65-79.

Written Opinion mailed on Nov. 25, 2010, for PCT Application No. PCT/US2009/052474, filed on Jul. 31, 2009, twenty-six pages.

Yuan, C. et al. (1991). "Studies on Organophosphorus Compounds 54. Synethsis of 1- Hydroxy-1-Alkyl(Aryl)-2-Aminoethylphosphonic Acids and Derivatives Thereof," *Phosphorus, Sulfur and Silicon* 63:111-118.

Zarbl, E. (2000). "Direct Liquid Chromatographic Enantioseparation of Chiral α- and β-Aminophosphonic Acids Employing Quinine-Derived Chiral Anion Exhangers: Determination of Enantiomeric Excess and Verification of Absolute Configuration," *Analytica Chimica Acta* 404:169-177.

Zygmunt, J. (1985). "Aziridine-2-Phosphonic Acid, The Valuable Synthon for Synthesis of 1- Amino-2-Functionalized Ethanephosphonic Acids," *Tetrahedron* 41(21)4979-4982.

Belmont, P.J. et al. (Spring 2010). "Epidemiology of Combat Wounds in OIF and OEF: Orthopaedic Burden of Disease," *J Surg Orthop Adv.* 19(1):2-7.

Clinicaltrials.Gov. (2008). "Wound Antiseptic Study With Hypochlorous Acid & Lodopovidone (WASH)," located at <http://www.clinicaltrials.gov/ct2/show/NCT00692757?term=NVC-101&rank=1>, last visited on May 30, 2013, three pages.

Clinicaltrials.Gov. (2013). "Search for NVC-422," located at <http://www.clinicaltrials.gov/ct2/results?term=NVC-422&Search=Search>, last visted on May 30, 2013, one page.

Clinicaltrials.Gov. (2013). "Safety and Efficacy Study of NVC-422 on Bacteriuria in Catheterized Patients," located at < http://www.clinicaltrials.gov/ct2/show_study/NCT00781339?term=NVC . . .>, last visited on May 30, 2013, three pages.

Clinicaltrials.Gov. (2013). "Safety and Efficacy of Topical NVC-422 Gel in Impetigo," located at <http://www.clinicaltrials.govict2/show/NCT0136731?/term=NVC422&rank=2 . . .>, last visited on May 30, 2013, three pages.

Clinicaltrials.Gov. (2013). "Study to Evaluate NVC-422 for Urinary Catheter Blockage and Encrustation," < http://www.clinicaltrials.gov/ct2/show/NCT012343125?term-NVC-422&rank3..>, last visited on May 30, 2013, four pages.

Clinicaltrials.Gov. (2013). "Efficacy and Safety of NVC-422 in the Treatment of Adenoviral conjunctivitis (BAYnovation™)," located at <http://www.clinicaltrials.gov/ct2/show/NCT01532336?term=NVC-422&rank=4..>, last visited on May 30, 2013, three pages.

Frackenpohl, J. et al. (2001). "The Outstanding Biological Stability of β- and γ-Peptides Toward Proteolytic Enzymes: An In Vitro Investigation with Fifteen Peptidases," *ChemBioChem.* 2:445-455.

Green, L.S. et al. (Jan. 2009). "Inhibition of Methionyl-tRNA Synthetase by REP8839 and Effects of Resistance Mutations on Enzyme Activity," *Antimicrobial Agents and Chemotherapy* 53(1):86-94.

Lee, J. et al. (1999). "Methionyl Adenylate Analogues as Inhibitors of Methionyl-tRNA Synthetase," *Bioorg. Med. Chem Lett.* 9:1365-1370.

Meredith, D. et al. (2000). "Modified Amino Acids and Peptides as Substrates for the Intestinal Peptide Transporter PepT1," *Eur. J. Biochem.* 267:3723-3728.

Moree, W. J. et al. (1993). "Synthesis of Peptides Containing a Sulfinamide or a Sulfonamide Transition-State Isostere," *Tetrahedron* 49(5):1133-1150.

Murray, C.K. et al. (Apr. 2009). "Infections in Combat Casualties During Operations Iraqi and Enduring Freedom," *J Trauma* 66(4):S138-S144.

Murray, C.K. et al. (Aug. 2011). "Prevention of Infections Associated With Combat-Related Extremity Injuries," *J. Trauma* 71(2)(Supp. 2):S235-S257.

Murray, C.K. et al. (Aug. 2011). "Guidelines for the Prevention of Infections Associated With Combat-Related Injuries: 2011 Updated," *J Trauma.* 71(2)(Suppl 2):S210-234.

Ochsner, U.A. et al. (Oct. 2005). "Mode of Action and Biochemical Characterization of REP8839, A Novel Inhibitor of Methionyl-tRNA Synthetase," *Antimicrob. Agents Chemother.* 49(10):4253-4262.

Owens, B.D. et al. (Apr. 2007). "Characterization of Extremity Wounds in Operation Iraqi Freedom and Operation Enduring Freedom," *J Orthop Trauma* 21(4):254-257.

Ranade, R.M. et al. (Apr. 15, 2013). "Induced Resistance to Methionyl-tRNA Synthetase Inhibitors in *Trypanosoma brucei* is Due to Overexpression of the Target," *Antimicrob. Agents Chemother.* pp. 1-31.

Shibata S. et al. (May 2011, e-pub. Jan. 31, 2011). "Selective Inhibitors of MethionyltRNA Synthetase Have Potent Activity Against *Trypanosoma brucei* Infection in Mice," *Antimicrob Agents and Chemother* 55(5):1982-1989.

Stewart, P.S. et al. (Jul. 14, 2001). "Antibiotic Resistance of Bacteria in Biofilms," *Lancet* 358: 135-138.

Tao, J. et al. (2000). "Inhibitors of Aminoacyl-tRNA Synthetases as Novel Anti-Infectives," *Exp. Opin. Invest. Drugs* 9(8):1767-1775.

Teng, M. et al. (2013, e-pub. Jan. 30, 2013). "Identification of Bacteria Selective Threonyl tRNA Synthetase (ThrRS) Substrate Inhibitors by Structure-Based Design," *J. Med. Chem.* pp. 1-41.

Tribble, D.R. et al. (Jul. 2011). "Infection-Associated Clinical Outcomes in Hospitalized Medical Evacuees After Traumatic Injury: Trauma Infectious Disease Outcome Study," *J. Trauma* 71(1 Suppl.):S33-S42.

Wang, L. et al. (Jun. 2011, e-pub. Mar. 21, 2011). "Chemical Characterization and Biological Properties of NVC-422, a Novel, Stable N-Chlorotaurine Analog," *Antimicrob. Agents and Chemother.* 55(6):2688-2692.

Weigand, H. et al. (2002). "The Outstanding Metabolic Stability of a [14]C-Labeled β-Nonapeptide in Rats—in vitro and in vivo Pharmacokinetic Studies," Biopharm. Drug Dispos. 23:251-262.

Yun, H.C. (Feb. 2008). "Osteomyelitis in Military Personnel Wounded in Iraq and Afghanistan," *J Trauma* 64(2):S163-5168, Discussion S168.

\* cited by examiner

METHIONINE ANALOGS AND METHODS OF USING SAME

CROSS REFERENCE TO RELATED APPLICATIONS

This application is a National Phase application under 35 U.S.C. §371 of International Application No. PCT/US2009/052474, filed Jul. 31, 2009, which claims priority to U.S. Provisional Application No. 61/085,556, filed Aug. 1, 2008, the disclosures of which are incorporated herein by reference in their entirety.

FIELD OF THE INVENTION

The present invention relates to novel methionine analogs which exhibit potential bactericidal, antibacterial, anti-infective, antimicrobial, sporicidal, disinfectant, antifungal and/or antiviral activity.

BACKGROUND OF THE INVENTION

The open-end battle of mankind against disease-causing microorganisms dates back to an era many years before Robert Koch and Louis Pasture's discoveries relating microorganisms as causative agents of disease. Since the early 1900's this era has been followed by the heroic efforts of microbiologists, biochemists and chemist to pave the road by their rigorous research studies to identify natural as well as synthetic sources of antimicrobial agents, including those derived from plants, marine organisms and microorganisms. In this regard, the first report on synthetic antimicrobials, sulfonamides, dates back to the mid-1930. Since this time, numerous natural and semi-synthetic antibacterial agents have been discovered and many of these introduced as chemotherapeutic agents to clinical use. However, over-use of these therapeutic agents within last 50 years has induced emergence of bacterial mutant resistance against these agents, thus, minimizing their therapeutic utilities as effective weapons in fighting infection.

Two parallel approaches are taken to overcome bacterial resistance. The first involves the development of agents to combat the bacterial resistance mechanism in order to revive the antibacterial potency of the parent molecule. These include, for example, inhibitors of β-lactamases and efflux pump inhibitors. The second approach focuses on novel antimicrobial agents with different targets and mechanism of action than those originally used (Mohsen Daneshtalab. Novel Synthetic Antimicrobials. Top Heterocycle Chem. Springer-Verlag Berlin Heidelberg 2006. 2:156-206). Unfortunately, slow progress has been made and additional new bacterial mutant resistance is on the rise.

The prevalence of bacterial resistance to conventional antibacterial agents has prompted multi-disciplinary scientists to search for antimicrobial targets with new antimicrobial agents. Certain bacterial targets, such as enzymes which participate in macromolecule synthesis, and are well characterized and hold promise for the discovery of novel antibacterial agents. For example, one target for discovery of a new class of anti-infectives is protein synthesis. Although there are similarities between the protein synthesizing machinery of prokaryote (microorganism) and eukaryote (mammalian) cells, there are sufficient differences that may be exploited for the development of new and selective antimicrobial agents. Bacterial aminoacyl-tRNA synthetases (aaRS) have been considered as promising antimicrobial targets because of their unique roles in protein biosynthesis (Vaughan M. D., et al. Investigation of Bioisosteric effects on the integration of substrates/inhibitors with the methionyl-tRNA synthetase from *Escherichia coli*. Medicinal Chemistry, 2005, 1:227-237; and Renau T. E., et al. Annual Reports in Medicinal Chemistry 1998, 33:121). Accordingly, it would be desirable to develop novel compounds which provide potential antimicrobial activity.

The disclosures of all publications, patents, patent applications and other references referred to herein are hereby incorporated herein by reference in their entireties.

BRIEF SUMMARY OF THE INVENTION

One aspect described herein are methods of treating an infection in an individual, comprising administering to the individual in need thereof, an effective amount of a compound of formula (I):

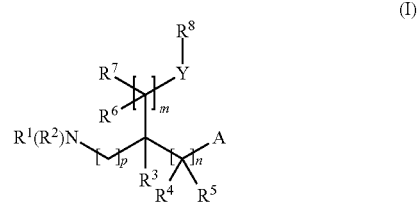

wherein A is $-SO_3H$, $-SO_2R^9$, $-SO_2N(R^{10})(R^{11})$, $-PO_3H_2$, $-PO_4H_2$, or $-C(O)NHOH$; Y is S or O; $R^1$ is hydrogen, $-C(O)R^{12}$, $-(B)_w-C$, $-OH$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; $R^2$ is hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ are taken together to form an optionally substituted 5 or 6-membered heterocyclic ring containing the nitrogen to which they are attached; each $R^3$, $R^4$, $R^5$, $R^6$, and $R^7$ is independently hydrogen, halogen, $-OR^{13}$, $-NO_2$, $-N(R^{14})(R^{15})$, $-SO_2R^{16}$, $-SO_2N(R^{17})(R^{18})$, $-SR^{19}$, $-C(O)R^{20}$, $-C(O)OR^{21}$, $-C(O)NHR^{22}$, $-NHC(O)R^{23}$, $-OC(O)R^{24}$, $-NHC(O)OR^{25}$, $-NHC(O)NHR^{26}$, $-OC(O)OR^{27}$, $-OC(O)NHR^{28}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; $R^8$, $R^{10}$, $R^{11}$, $R^{12}$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, heteroaralkyl; $R^9$ and $R^{16}$ are each independently or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; and m, n, and p are independently 0, 1, 2, 3, or 4; each B and C is an optionally substituted amino acid moiety; and w is 0, 1, or 2;

or a pharmaceutically acceptable salt thereof or solvate of the foregoing.

In another aspect, are provided methods of inhibiting the growth of a microorganism (e.g., a bacteria, spore, fungus, or virus), comprising contacting the microorganism with a compound of the formula (I).

In another aspect, are provided methods of inhibiting protein synthesis in a microorganism (e.g., a bacteria, spore, fungus, or virus), comprising contacting the microorganism with a compound of the formula (I).

In another aspect, is a provided a compound of formula (I) with the proviso that when A is —SO$_3$H, Y is S, p is 0, both R$^1$ and R$^2$ are hydrogen, and R$^8$ is methyl or benzyl, then n is 1, 2, 3 or 4; and with the additional proviso that when A is —PO$_3$H$_2$, Y is S, and p is 0, then n is 1, 2, 3 or 4; or a pharmaceutically acceptable salt thereof or solvate of the foregoing. In some of these embodiments of the compound of formula (I), when A is —C(O)NHOH, R$^1$ is —C(O)R$^{12}$ (e.g., —C(O)H) or —(B)$_w$—C (e.g., R$^1$ is an optionally substituted amino acid moiety, such as

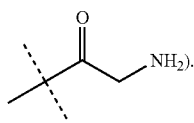

In some embodiments, when A is —C(O)NHOH, R$^1$ is —(B)$_w$—C (e.g., R$^1$ is an optionally substituted amino acid moiety, such as

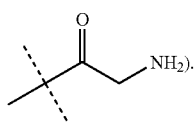

In another aspect, is provided a formulation comprising a compound of formula (I) and a carrier. In some embodiments, the formulation comprises an effective amount of the compound. In some embodiments, the carrier is a pharmaceutically acceptable carrier. In some embodiments, the formulation is stable. In some embodiments, the compound is at a concentration of about 0.1 mM to about 500 mM, and the pH is about 5.0 to about 8.0. In some embodiments, the compound is at a concentration of about 1 mM to about 50 mM and the pH is about 6.5 to about 8.0. In some embodiments, the compound of formula (I) is in a substantially pure form.

In another aspect, is provided a compound of formula (I) for use in a method of treating an infection in an individual.

In another aspect, is provided the use a compound of formula (I) for the manufacture of a medicament for use in a method of treating an infection in an individual.

DETAILED DESCRIPTION

DETAILED DESCRIPTION OF THE INVENTION

Figure 1A:
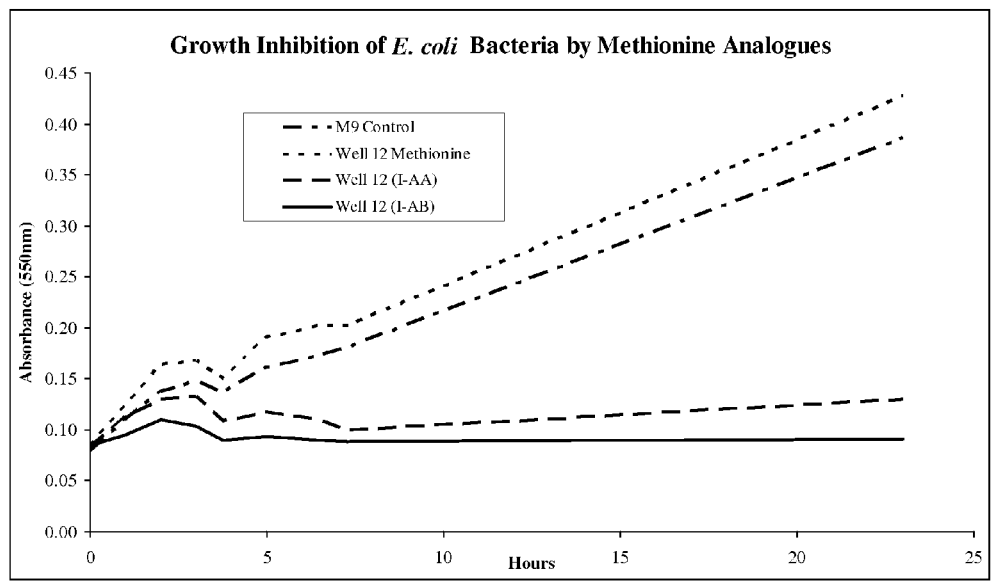
FIG. 1A depicts growth inhibition of *E. coli* bacteria by methionine analogs (12.5 mM) over a 24 hr period.

Provided herein are methionine analogs comprising a modified carboxylate terminus. Such compounds may be useful for inhibiting protein synthesis, inhibiting microbial growth and/or treating infectious diseases.

In one aspect are provided the methionine analogs described herein. In other aspects are provided methods of using the analogs described herein, such as treating an infection in an individual. Also provided are kits and unit dosage forms of the analogs.

Abbreviations and Definitions

The terms "halo" or "halogen," by themselves or as part of another substituent, mean, unless otherwise stated, a fluorine, chlorine, bromine, or iodine atom.

The term "alkyl," by itself or as part of another substituent, means, unless otherwise stated, a fully saturated straight-chain (linear; unbranched) or branched chain, or combination thereof, having the number of carbon atoms specified, if designated (i.e. C$_1$-C$_{10}$ means one to ten carbons). Examples include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. If no size is designated, the alkyl groups mentioned herein contain 1-20 carbon atoms, typically 1-10 carbon atoms, or 1-8 carbon atoms, or 1-6 carbon atoms, or 1-4 carbon atoms. The term "alkylene" is by itself or in combination with other terms, represents a divalent radical derived from an alkyl, as exemplified, but not limited, by —CH$_2$CH$_2$CH$_2$CH$_2$—.

The term "alkenyl" refers to unsaturated aliphatic groups including straight-chain (linear; unbranched), branched-chain groups, and combinations thereof, having the number of carbon atoms specified, if designated, which contain at least one double bond (—C=C—). All double bonds may be independently either (E) or (Z) geometry, as well as mixtures thereof. Examples of alkenyl groups include, but are not limited to, —CH$_2$—CH=CH—CH$_3$; —CH=CH—CH=CH$_2$ and —CH$_2$—CH=CH—CH(CH$_3$)—CH$_2$—CH$_3$. If no size is designated, the alkenyl groups mentioned herein contain 2-20 carbon atoms, typically 2-10 carbon atoms, or 2-8 carbon atoms, or 2-6 carbon atoms, or 2-4 carbon atoms.

The term "alkynyl" refers to unsaturated aliphatic groups including straight-chain (linear; unbranched), branched-chain groups, and combinations thereof, having the number of carbon atoms specified, if designated, which contain at least one carbon-carbon triple bond (—C≡C—). Examples of alkynyl groups include, but are not limited to, —CH$_2$—C≡C—CH$_3$; —C≡C—C≡CH and —CH$_2$—C≡C—CH(CH$_3$)—CH$_2$—CH$_3$. If no size is designated, the alkynyl groups mentioned herein contain 2-20 carbon atoms, typically 2-10 carbon atoms, or 2-8 carbon atoms, or 2-6 carbon atoms, or 2-4 carbon atoms.

The term "cycloalkyl" by itself or in combination with other terms, represents, unless otherwise stated, a saturated or unsaturated cyclic non-aromatic hydrocarbon radical (e.g., cyclic versions of alkyl, alkenyl, or alkynyl, or mixtures thereof). Cycloalkyl may contain additional fused rings (e.g., from 1 to 3 rings), including additionally fused cycloalkyl and/or heterocycloalkyl rings, but excludes additionally fused aryl and/or heteroaryl groups. Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like. If no size is designated, the alkynyl groups mentioned herein contain 3-9 carbon atoms, typically 3-7 carbon atoms.

The term "heterocycloalkyl," by itself or in combination with other terms, represents a saturated or unsaturated cyclic non-aromatic hydrocarbon radical containing of at least one carbon atom and at least one annular heteroatom selected from the group consisting of O, N, P, Si and S, and wherein the nitrogen and sulfur atoms may optionally be oxidized and the nitrogen heteroatom may optionally be quaternized. The heteroatom(s) O, N, P, S and Si may be placed at any interior position of the heterocycloalkyl group or at the position at which the heterocycloalkyl group is attached to the remainder of the molecule. Heterocycloalkyl may contain additional fused rings (e.g., from 1 to 3 rings), including additionally fused cycloalkyl and/or heterocycloalkyl rings, but excludes additionally fused aryl and/or heteroaryl groups. Examples of heterocycloalkyl include, but are not limited to, thiazolidinonyl, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "cycloalkyl-alkyl" and "heterocycloalkyl-alkyl" designate an alkyl-substituted cycloalkyl group and alkyl-substituted heterocycloalkyl, respectively, where the alkyl moiety is attached to the parent structure. Non-limiting examples include cyclopropyl-ethyl, cyclobutyl-propyl, cyclopentyl-hexyl, cyclohexyl-isopropyl, 1-cyclohexenyl-propyl, 3-cyclohexenyl-t-butyl, cycloheptyl-heptyl, norbornyl-methyl, 1-piperidinyl-ethyl, 4-morpholinyl-propyl, 3-morpholinyl-t-butyl, tetrahydrofuran-2-yl-hexyl, tetrahydrofuran-3-yl-isopropyl, and the like. Cycloalkyl-alkyl and heterocycloalkyl-alkyl also include substituents in which at least one carbon atom is present in the alkyl group and wherein another carbon atom of the alkyl group has been replaced by, for example, an oxygen, nitrogen or sulfur atom (e.g., cyclopropoxymethyl, 2-piperidinyloxy-t-butyl, and the like).

The term "aryl" means, unless otherwise stated, a polyunsaturated, aromatic, hydrocarbon substituent. Aryl may contain additional fused rings (e.g., from 1 to 3 rings), including additionally fused aryl, heteroaryl, cycloalkyl, and/or heterocycloalkyl rings. Examples of aryl groups include, but are not limited to, phenyl, 1-naphthyl, 2-naphthyl, 4-biphenyl.

The term "heteroaryl" refers to aryl groups (or rings) that contain from one to four annular heteroatoms selected from N, O, and S, wherein the nitrogen and sulfur atoms are optionally oxidized, and the nitrogen atom(s) are optionally quaternized. A heteroaryl group can be attached to the remainder of the molecule at an annular carbon or annular heteroatom. Heteroaryl may contain additional fused rings (e.g., from 1 to 3 rings), including additionally fused aryl, heteroaryl, cycloalkyl, and/or heterocycloalkyl rings. Non-limiting examples of heteroaryl groups are 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

The term "aralkyl" designates an alkyl-substituted aryl group, where the alkyl portion is attached to the parent structure. Examples are benzyl, phenethyl, and the like. "Heteroaralkyl" designates a heteroaryl moiety attached to the parent structure via an alkyl residue. Examples include furanylmethyl, pyridinylmethyl, pyrimidinylethyl, and the like. Aralkyl and heteroaralkyl also include substituents in which at least one carbon atom of the alkyl group is present in the alkyl group and wherein another carbon of the alkyl group has been replaced by, for example, an oxygen atom (e.g., phenoxymethyl, 2-pyridylmethoxy, 3-(1-naphthyloxy)propyl, and the like).

The term "substituted" refers to the replacement of one or more hydrogen atoms of a moiety with a monovalent or divalent radical. "Optionally substituted" indicates that the moiety may be substituted or unsubstituted. A moiety lacking the terms "optionally substituted" and "substituted" is intended an unsubstituted moiety (e.g., "phenyl" is intended an unsubstituted phenyl unless indicated as a substituted phenyl or an optionally substituted phenyl). Suitable substituent groups include, for example, hydroxyl, nitro, amino (e.g., —$NH_2$ or dialkyl amino), imino, cyano, halo (such as F, Cl, Br, I), haloalkyl (such as —$CCl_3$ or —$CF_3$), thio, sulfonyl, thioamido, amidino, imidino, oxo, oxamidino, methoxamidino, imidino, guanidino, sulfonamido, carboxyl, formyl, alkyl, alkoxy, alkoxy-alkyl, alkylcarbonyl, alkylcarbonyloxy (—OCOR), aminocarbonyl, arylcarbonyl, aralkylcarbonyl, carbonylamino, heteroarylcarbonyl, heteroaralkyl-carbonyl, alkylthio, aminoalkyl, cyanoalkyl, carbamoyl (—NHCOOR— or —OCONHR—), urea (—NHCONHR—), aryl and the like, where R is any suitable group, e.g., alkyl or alkylene. In some embodiments, the optionally substituted moiety is optionally substituted only with select radicals, as described. In some embodiments, the above groups (e.g., alkyl groups) are optionally substituted with, for example, alkyl (e.g., methyl or ethyl), haloalkyl (e.g., —$CCl_3$, —$CH_2CHCl_2$ or —$CF_3$), cycloalkyl (e.g., —$C_3H_5$, —$C_4H_7$, —$O_5H_9$), amino (e.g., —$NH_2$ or dialkyl amino), alkoxy (e.g., methoxy), heterocycloalkyl (e.g., as morpholine, piperazine, piperidine, azetidine), hydroxyl, and/or heteroaryl (e.g., oxazolyl). In some embodiments, a substituent group is itself optionally substituted. In some embodiments, a substituent group is not itself substituted. The group substituted onto the substitution group can be, for example, carboxyl, halo, nitro, amino, cyano, hydroxyl, alkyl, alkenyl, alkynyl, alkoxy, aminocarbonyl, —SR, thioamido, —$SO_3H$, —$SO_2R$ or cycloalkyl, where R is any suitable group, e.g., a hydrogen or alkyl.

When the substituted substituent includes a straight chain group, the substituent can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms (N, O or S).

The term "amino acid" as used herein refers to any of the naturally occurring amino acids, as well as synthetic analogs (e.g., D-stereoisomers of the naturally occurring amino acids, such as D-valine or D-alanine) and derivatives thereof. Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). Unnatural amino acids are also known in the art, as set forth in, for example, Williams (ed.), Synthesis of Optically Active a-Amino Acids, Pergamon Press (1989); Evans et al., J. Amer. Chem. Soc., 112: 4011-4030 (1990); Pu et al., J. Amer. Chem. Soc., 56:1280-1283 (1991); Williams et al., J. Amer. Chem. Soc., 113:9276-9286 (1991) (and all references cited therein), the contents of which are hereby incorporated herein by reference in its entireties, particularly with respect to the amino acids described therein. The analogs described herein include the side chains of unnatural amino acids as well, unless otherwise indicated.

As used herein, "treatment", "treating", or "treat" is an approach for obtaining beneficial or desired results, including clinical results. For purposes herein, beneficial or desired results include, but are not limited to, one or more of the following: decreasing one more symptoms resulting from the condition (e.g., an infection), diminishing the extent of the condition, stabilizing the condition (e.g., preventing or delaying the worsening of the condition, such as an infection), delay or slowing the progression of the condition, ameliorating the condition state, decreasing the dose of one or more other medications required to treat the condition, increasing the quality of life of an individual who has been or is suspected of having the condition, and/or prolonging survival (including overall survival and progression free survival). Also encompassed by "treatment" is a reduction of pathological consequence of the condition (e.g., an infection). The methods described herein contemplate any one or more of these aspects of treatment.

As used herein, "inhibit" means to delay, reduce, slow, postpone, and/or prevent the development of the response or parameter described (e.g., growth of a microorganism, synthesis of a protein, etc). As used herein, "delaying" means to defer, hinder, slow, retard, stabilize, and/or postpone development of, and/or one or more symptoms of the condition (e.g., an infection). This delay can be of varying lengths of time, depending on the history of the condition and/or individual being treated. As is evident to one skilled in the art, a sufficient or significant delay can, in effect, encompass prevention, in that the individual does not develop the condition (e.g., an infection). A method that "delays" development of a condition is a method that may reduce the probability of condition development in a given time frame and/or reduces the extent of the condition in a given time frame, when compared to not using the method. Such comparisons are typically based on clinical studies, using a statistically significant number of subjects. Development of an infection can be detected using standard methods known in the art, such as routine physical exams or clinical detection (e.g., culture enrichment, gene amplification, and/or ELISA detection via microscopy, and other imaging techniques, such as X-rays, CAT scans, PET scans and NMR). Development may also refer to condition progression that may be initially undetectable and includes occurrence and onset.

As used herein, an "at risk" individual is an individual who is at risk of developing a condition (e.g., an infection). An individual "at risk" may or may not have a detectable condition, and may or may not have displayed symptoms associated with a detectable condition prior to the treatment methods described herein. "At risk" denotes that an individual has one or more so-called risk factors, which are measurable parameters that correlate with development of the condition. An individual having one or more of these risk factors has a higher probability of developing the condition than an individual without these risk factor(s).

As used herein, "pharmaceutically acceptable" refers to a material that is not biologically or otherwise undesirable, e.g., the material may be incorporated (e.g., at the time of manufacturing or administration) into a pharmaceutical formulation administered to an individual without causing any significant undesirable biological effects or interacting in a deleterious manner with any of the other components of the formulation in which it is contained. As used herein, the term "pharmaceutically acceptable carrier," refers to, for example, solvents, stabilizers, pH-modifiers, tonicity modifiers, adjuvants, binders, diluents, etc., known to the skilled artisan that are suitable for administration to an individual (e.g., a human). Combinations of two or more carriers are also contemplated. The pharmaceutically acceptable carrier(s) and any additional components, as described herein, should be compatible for use in the intended route of administration (e.g., topical, oral, parenteral) for a particular dosage form. Such suitability will be easily recognized by the skilled artisan, particularly in view of the teaching provided herein. Pharmaceutically acceptable carriers or excipients have preferably met the required standards of toxicological and manufacturing testing and/or are included on the Inactive Ingredient Guide prepared by the U.S. Food and Drug administration.

An "effective amount," as used herein refer to an amount that results in a desired pharmacological and/or physiological effect for a specified condition (e.g., an infection) or one or more of its symptoms and/or to completely or partially prevent the occurrence or recurrence of the condition or symptom thereof and/or may be therapeutic in terms of a partial or complete cure for the condition and/or adverse effect attributable to the condition (e.g., an infection). In reference to conditions described herein (e.g., an infection), a pharmaceutically or therapeutically effective amount may comprise an amount sufficient to, among other things, reduce the number of microbial cells, inhibit microbial cell growth and/or kill existing microbial cells, reduction of morbidity and/or mortality, and/or relieve to some extent one or more of the symptoms associated with the infection. In certain embodiments, the pharmaceutically effective amount is sufficient to prevent the condition, as in being administered to an individual prophylactically. Effective amount includes the eradication or amelioration of the underlying condition being treated and/or eradication or amelioration of one or more of the symptoms associated with the underlying condition such that the individual reports an improvement in feeling or condition (e.g., decreased pain intensity and/or duration), notwithstanding that the individual may still be afflicted with the underlying condition. Effective amount also includes halting or slowing the progression of the condition (e.g., an infection), regardless of whether improvement or the condition is realized.

The "effective amount" may vary depending on the analog being administered, the condition being treated/prevented (e.g., the type of bacterial infection), the severity of the condition being treated or prevented, the age, body size, weight, and relative health of the individual, the route and form of administration, the judgment of the attending medical or veterinary practitioner (if applicable), and other factors appreciated by the skilled artisan in view of the teaching provided herein. An effective amount may be assessed, for example, by using data from one or more clinical, physiological, biochemical, histological, electrophysiological, and/or behavioral evaluations.

As is understood in the art, an "effective amount" may be in one or more doses, i.e., a single dose or multiple doses may be required to achieve the desired treatment endpoint. An effective amount may be considered in the context of administering one or more additional pharmaceutical agents, and an analog may be considered to be given in an effective amount if, in conjunction with one or more additional pharmaceutical agents, one or more desirable or beneficial result(s) may be or are achieved.

When used with respect to methods of treatment/prevention and the use of the analogs and formulations thereof described herein, an individual "in need thereof" may be an individual who has been diagnosed with, previously treated for, and/or suspected of having the condition to be treated (e.g., an infection). With respect to prevention, the individual in need thereof may also be an individual who is at risk for a condition (e.g., a family history of the condition, life-style factors indicative of risk for the condition, etc.).

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children, infants, and preemies. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. In some embodiments, the individual is a non-mammal, including, but not limited to, birds, and the like. The term "individual" does not denote a particular age or sex.

As used herein, "combination therapy" means a first therapy that includes an analog in conjunction with a second therapy (e.g., surgery and/or an additional pharmaceutical agent) useful for treating, stabilizing, preventing, and/or delaying the condition. Administration in "conjunction with" another compound includes administration in the same or different formulation(s), either sequentially, simultaneously, or continuously, through the same or different routes. In some embodiments, the combination therapy optionally includes one or more pharmaceutically acceptable carriers or excipients, non-pharmaceutically active compounds, and/or inert substances.

As used herein, the term "additional pharmaceutical agent," refers to an active agent other than an analog described herein, for example, a drug, which is administered to elicit a therapeutic effect. The pharmaceutical agent(s) may be directed to a therapeutic effect related to the condition that the analogs are intended to treat or prevent (e.g., an infection) or, the pharmaceutical agent may be intended to treat or prevent a symptom of the underlying condition (e.g., fever, chronic wounds, gangrene, ulceration, swelling, diarrhea, dehydration, lethargy, vomiting, inflammation, pain, rash development, etc.) or to further reduce the appearance or severity of side effects of the analogs.

Reference to "about" a value or parameter herein includes (and describes) variations that are directed to that value or parameter per se. For example, a description referring to "about X" includes the description of "X". When used in combination with measured values, "about" includes a range that encompasses at least the uncertainty associated with the method of measuring the particular value, and can include a range of plus or minus one or two standard deviations around the stated value. When used to describe estimated values or compound dosages, it includes a range of plus or minus 10% of the stated value, or in some embodiments a range of plus or minus 5% around the stated value.

As used herein and in the appended claims, the singular forms "a," "or," and "the" include plural referents unless the context clearly dictates otherwise. It is understood that aspect and variations described herein include "consisting" and/or "consisting essentially of" aspects and variations.

Unless defined otherwise or clearly indicated by context, all technical and scientific terms and abbreviations used herein have the same meaning as commonly understood by one of ordinary skill in the art to which this invention belongs.

Target Analogs

Described herein are methionine analogs which may be useful in the treatment of conditions (such as infections), inhibiting the growth of a microorganism, and/or inhibiting protein synthesis.

In one aspect, the analog is a compound of the formula (I):

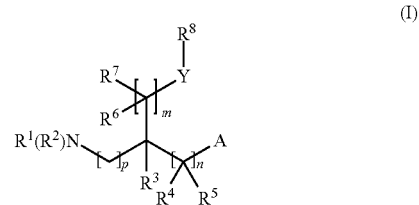

wherein

A is —$SO_3H$, —$SO_2R^9$, —$SO_2N(R^{10})(R^{11})$, —$PO_3H_2$, —$PO_4H_2$ or —C(O)NHOH;

Y is S or O;

$R^1$ is hydrogen, —$C(O)R^{12}$, —$(B)_w$—C, —OH, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

$R^2$ is hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

or wherein $R^1$ and $R^2$ are taken together to form an optionally substituted 5 or 6-membered heterocyclic ring containing the nitrogen to which they are attached;

each $R^3$, $R^4$, $R^5$, $R^6$, and $R^7$ is independently hydrogen, halogen, —$OR^{13}$, —$NO_2$, —$N(R^{14})(R^{15})$, —$SO_2R^{16}$, —$SO_2N(R^{17})(R^{18})$, —$SR^{19}$, —$C(O)R^{20}$, —$C(O)OR^{21}$, —$C(O)NHR^{22}$, —$NHC(O)R^{23}$, —$OC(O)R^{24}$, —$NHC(O)OR^{25}$, —$NHC(O)NHR^{26}$, —$OC(O)OR^{27}$, —$OC(O)NHR^{28}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

$R^8$, $R^{10}$, $R^{11}$, $R^{12}$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

$R^9$ and $R^{16}$ are independently an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, heteroaralkyl;

m, n, and p are independently 0, 1, 2, 3, or 4;

each B and C is an optionally substituted amino acid moiety; and w is 0, 1, or 2;

or a pharmaceutically acceptable salt thereof or solvate of the foregoing.

In some embodiments of the compound of formula I A is —$SO_3H$, —$SO_2R^9$, —$SO_2N(R^{10})(R^{11})$, —$PO_3H_2$, —$PO_4H_2$ or —C(O)NHOH; Y is S or O; $R^1$ is hydrogen, —$C(O)R^{12}$, —$(B)_w$—C, —OH, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; $R^2$ is hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein $R^1$ and $R^2$ are taken together to form an optionally substituted 5 or 6-membered heterocyclic ring containing the nitrogen to which they are attached; each $R^3$, $R^4$, $R^5$, $R^6$, and $R^7$ is independently hydrogen, halogen, —$OR^{13}$, —$NO_2$, —$N(R^{14})(R^{15})$, —$SO_2R^{16}$, —$SO_2N(R^{17})(R^{18})$, —$SR^{19}$, —$C(O)R^{20}$, —$C(O)OR^{21}$, —$C(O)NHR^{22}$, —$NHC(O)R^{23}$, —$OC(O)R^{24}$, —$NHC(O)OR^{25}$, —$NHC(O)NHR^{26}$, —$OC(O)OR^{27}$, —$OC(O)NHR^{28}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; $R^8$, $R^{10}$, $R^{11}$, $R^{12}$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; $R^9$ and $R^{16}$ are independently an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, heteroaralkyl; m, n, and p are independently 0, 1, 2, 3, or 4; each B and C is an optionally substituted amino acid moiety; and w is 0, 1, or 2; or a pharmaceutically acceptable salt thereof or solvate of the foregoing.

In some embodiments, the compound of formula I has the proviso that when A is —$SO_3H$, Y is S, p is 0, both $R^1$ and $R^2$ are hydrogen, and $R^8$ is methyl or benzyl, then n is 1, 2, 3 or 4. In some embodiments, the compound has the additional proviso that when A is —$PO_3H_2$, Y is S, and p is 0, then n is 1, 2, 3 or 4. In some of these embodiments of the compound of formula I, when A is —C(O)NHOH, $R^1$ is —$C(O)R^{12}$ (e.g., —C(O)H) or —$(B)_w$—C (e.g., $R^1$ is an optionally substituted amino acid moiety, such as

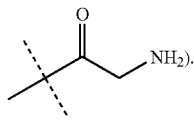

In some embodiments, the compound of formula I has the proviso that when A is —$SO_3H$, both $R^1$ and $R^2$ are hydrogen, and $R^8$ is methyl or benzyl, then n is 1, 2, 3 or 4. In some embodiments, the compound has the additional proviso that when A is —$PO_3H_2$, then n is 1, 2, 3 or 4. In some of these embodiments of the compound of formula I, when A is —C(O)NHOH, $R^1$ is —$C(O)R^{12}$ (e.g., —C(O)H) or —$(B)_w$—C (e.g., $R^1$ is an optionally substituted amino acid moiety, such as

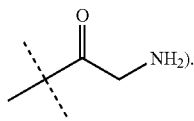

In some embodiments, the compound of formula I has the proviso that when A is —$SO_3H$, both $R^1$ and $R^2$ are hydrogen, and $R^8$ is alkyl or aralkyl, then n is 1, 2, 3 or 4. In some embodiments, the compound has the proviso when A is —$SO_3H$, both $R^1$ and $R^2$ are hydrogen, and $R^8$ is an optionally substituted alkyl or an optionally substituted aralkyl, then n is 1, 2, 3 or 4. In some embodiments, the compound of formula I has the proviso that when A is —$PO_3H_2$, then n is 1, 2, 3 or 4. In some of these embodiments of the compound of formula I, when A is —C(O)NHOH, $R^1$ is —$C(O)R^{12}$ (e.g., —C(O)H) or —$(B)_w$—C (e.g., $R^1$ is an optionally substituted amino acid moiety, such as

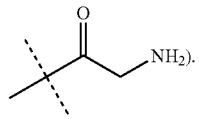

In some of these embodiments of the compound of formula I, each optionally substituted moiety is the indicated moiety optionally substituted with one or more groups selected from hydroxyl, nitro, amino, imino, cyano, halo, haloalkyl, thiol, thioalkyl, sulfonyl, thioamido, amidino, oxo, oxamidino, methoxamidino, imidino, guanidino, sulfonamido, carboxyl, formyl, alkyl, cycloalkyl, alkoxy, alkoxy-alkyl, alkylcarbonyl, alkylcarbonyloxy, aminocarbonyl, aryl, heteroaryl, arylcarbonyl, aralkylcarbonyl, carbonylamino, heteroarylcarbonyl, heteroaralkyl-carbonyl, alkylthio, aminoalkyl, cyanoalkyl, carbamoyl, and urea. In some embodiments, each optionally substituted moiety is the indicated moiety optionally substituted with one or more groups selected from hydroxyl, nitro, amino, cyano, halo, haloalkyl, thiol, thioalkyl, sulfonyl, thioamido, amidino, carboxyl, formyl, alkyl, cycloalkyl, alkoxy, and alkoxy-alkyl.

In some of these embodiments of the compound of formula I, A is —$SO_3H$, —$SO_2R^9$, —$SO_2N(R^{10})(R^{11})$, —$PO_3H_2$ or —C(O)NHOH. In some embodiments, A is —$SO_3H$, —$SO_2R^9$, $SO_2N(R^{10})(R^{11})$ or —$PO_3H_2$. In some embodiments, A is —$SO_3H$ or —$PO_3H_2$. In some embodiments, A is —$PO_4H_2$ or —$PO_3H_2$. In some embodiments, A is —$PO_3H_2$. In some embodiments, A is —$PO_4H_2$. In some embodiments, A is —$SO_3H$. In some embodiments A is —C(O)NHOH. In some embodiments A is —C(O)NHOH and $R^1$ is —$(B)_w$—C (e.g., $R^1$ is an optionally substituted amino acid moiety, such as

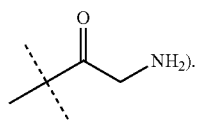

In some of these embodiments, $R^2$ is H.

In some of these embodiments of the compound of formula I, Y is S. In some embodiments, Y is O.

In some of these embodiments of the compound of formula I, m is 1, 2, or 3. In some embodiments, m is 1 or 2. In some embodiments, m is 1. In some embodiments, m is 2. In some embodiments, n is 0, 1, or 2. In some embodiments, n is 0 or 1. In some embodiments, n is 0. In some embodiments, n is 1. In some embodiments, p is 0, 1, or 2. In some embodiments, p is 0 or 1. In some embodiments, p is 0. In some embodiments, wherein p is 1. In some embodiments, m is 1 or 2, n is 0 or 1, and p is 0 or 1. In some embodiments, m is 1 or 2, n is 0, and p is 0. In some embodiments, m is 1 or 2, n is 1, and p is 0. In some embodiments, m is 1 or 2, n is 0, and p is 1. In some embodiments, m is 1, n is 0, and p is 0. In some embodiments, m is 2, n is 0, and p is 0. In some embodiments, m is 1, n is 1, and p is 0. In some embodiments, m is 2, n is 1, and p is 0. In some embodiments, m is 1, n is 0, and p is 1. In some embodiments, m is 2, n is 0, and p is 1.

In some of these embodiments of the compound of formula I, $R^1$ is hydrogen, —C(O)$R^{12}$, —(B)$_q$—C, —OH, or an optionally substituted alkyl. In some embodiments, $R^1$ is hydrogen, —C(O)$R^{12}$, or —(B)$_q$—C. In some embodiments, $R^1$ is hydrogen or —C(O)$R^{12}$. In some embodiments, $R^1$ is hydrogen. In some embodiments, $R^1$ is —(B)$_q$—C. In some embodiments, $R^1$ is —C(O)$R^{12}$. In some of these embodiments, $R^{12}$ is hydrogen, or an optionally substituted alkyl. In some embodiments, $R^{12}$ is hydrogen.

In some of these embodiments of the compound of formula I, $R^1$ is —(B)$_w$—C. In some embodiments, the B moiety attached to $R^1$ is linked through an amide bond. In some embodiments, each B and C moiety is attached to its adjacent B or C moiety through an amide bond. In some embodiments, at least one B or C is an optionally substituted aliphatic amino acid moiety (e.g., glycine, valine, alanine, leucine, and isoleucine). In some embodiments, each B and C is an optionally substituted aliphatic amino acid moiety (e.g., glycine, valine, alanine, leucine, and isoleucine). In some embodiments, each B and C is selected from glycine and valine. In some embodiments, $R^1$ is selected from the group consisting of

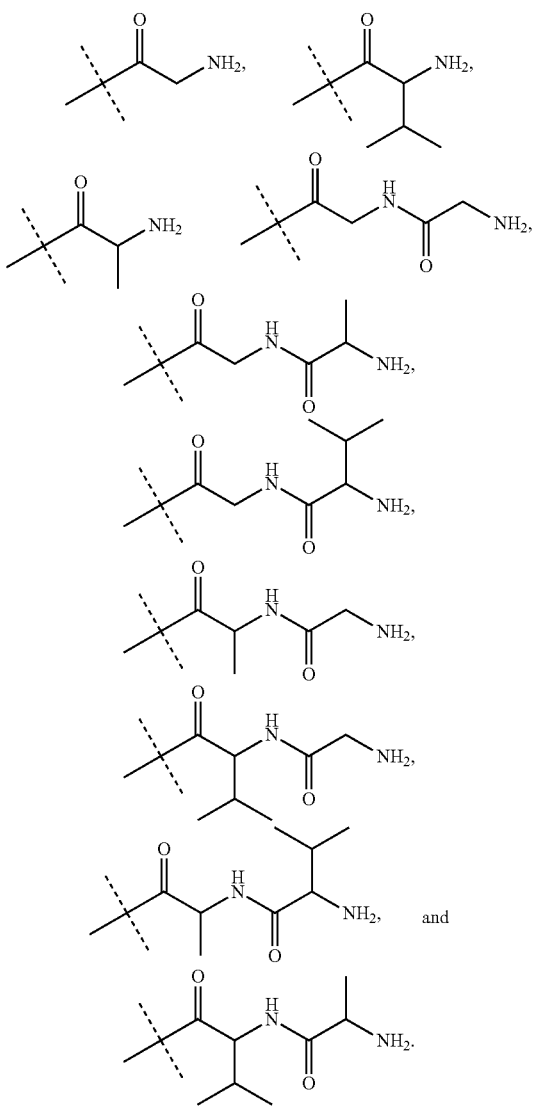

and

In some of these embodiments, $R^2$ is H. In some embodiments, $R^1$ is

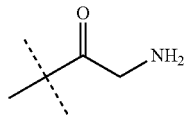

and $R^2$ is H. In some of these embodiments, w is 0. In some embodiments, w is 1. In other embodiments, w is 2. In some embodiments, at least one B or C amino acid is in the D form. In some embodiments, at least one B or C amino acid is in the L form. In some embodiments, each B and C amino acid is in the D form. In some embodiments, each B and C amino acid (e.g., gly-gly-) is in the L form.

In some of these embodiments of the compound of formula I, each $R^3$, $R^4$, $R^5$, $R^6$, and $R^7$ is independently hydrogen, halogen (e.g., Cl, F, I, Br), or —O$R^{13}$. In some embodiments, each $R^3$, $R^4$, $R^5$, $R^6$, and $R^7$ is independently hydrogen or halogen (e.g., Cl, F, I, Br). In some embodiments, $R^3$, $R^4$, $R^5$, $R^6$, and $R^7$ are hydrogen.

In some of these embodiments of the compound of formula I, $R^8$ is an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl. In some embodiments, $R^8$ is hydrogen or an optionally substituted alkyl. In some embodiments, $R^8$ is hydrogen. In some embodiments, $R^8$ is an optionally substituted alkyl. In some embodiments, $R^8$ is alkyl. In some embodiments, $R^8$ is a $C_1$-$C_5$ alkyl. In some embodiments, $R^8$ is methyl or ethyl. In some embodiments, $R^8$ is methyl.

In some embodiments, the compound of formula (I) is any one, combination, or all of:

(I-A):

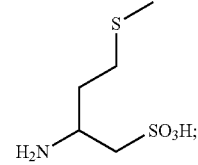

2-amino-4-(methylthio)butane-1-sulfonic acid (I-B):

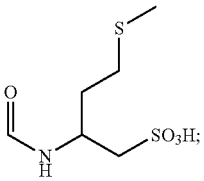

2-formamido-4-(methylthio)butane-1-sulfonic acid (I-C):

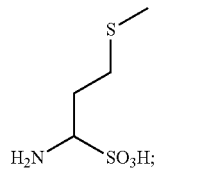

1-amino-3-(methylthio)propane-1-sulfonic acid (I-D):

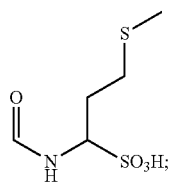

1-formamido-3-(methylthio)propane-1-sulfonic acid (I-E):

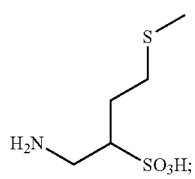

1-amino-4-(methylthio)butane-2-sulfonic acid (I-F):

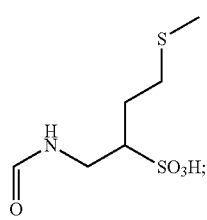

1-formamido-4-(methylthio)butane-2-sulfonic acid (I-G):

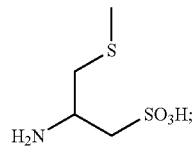

2-amino-3-(methylthio)propane-1-sulfonic acid (I-H):

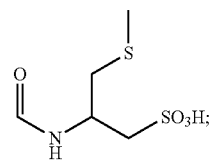

2-formamido-3-(methylthio)propane-1-sulfonic acid (I-I):

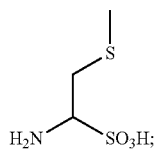

1-amino-2-(methylthio)ethanesulfonic acid (I-J):

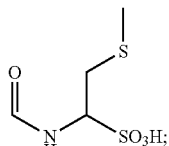

1-formamido-2-(methylthio)ethanesulfonic acid (I-K):

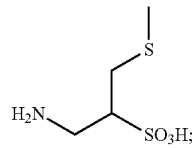

1-amino-3-(methylthio)propane-2-sulfonic acid (I-L):

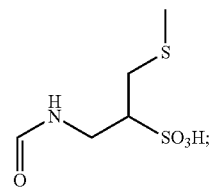

1-formamido-3-(methylthio)propane-2-sulfonic acid (I-M):

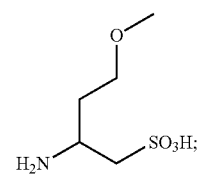

2-amino-4-methoxybutane-1-sulfonic acid (I-N):

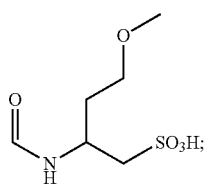

2-formamido-4-methoxybutane-1-sulfonic acid (I-O):

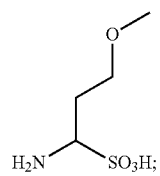

1-amino-3-methoxypropane-1-sulfonic acid (I-P):

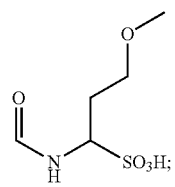

1-formamido-3-methoxypropane-1-sulfonic acid (I-Q):

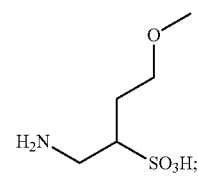

1-amino-4-methoxybutane-2-sulfonic acid (I-R):

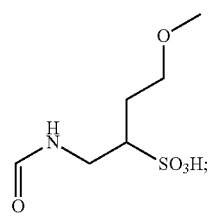

1-formamido-4-methoxybutane-2-sulfonic acid (I-S):

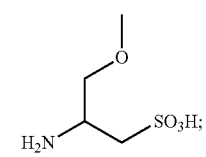

2-amino-3-methoxypropane-1-sulfonic acid (I-T):

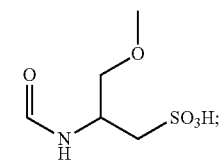

2-formamido-3-methoxypropane-1-sulfonic acid (I-U):

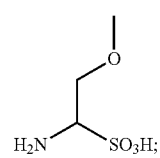

1-amino-2-methoxyethanesulfonic acid (I-V):

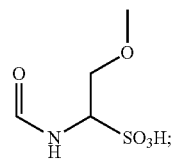

1-formamido-2-methoxyethanesulfonic acid (I-W):

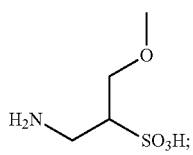

1-amino-3-methoxypropane-2-sulfonic acid (I-X):

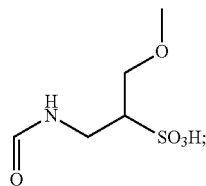

1-formamido-3-methoxypropane-2-sulfonic acid (I-Y):

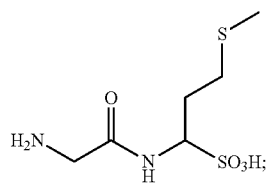

1-(2-aminoacetamido)-3-(methylthio)propane-1-sulfonic acid (I-Z):

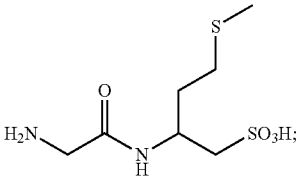

2-(2-aminoacetamido)-3-(methylthio)butane-1-sulfonic acid (I-AA):

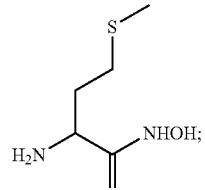

2-amino-N-hydroxy-4-(methylthio)butanamide

-continued (I-AB):

[Structure: H2N-CH2-C(O)-NH-CH(CH2CH2SCH3)-C(O)-NHOH]

2-(2-aminoacetamido)-N-hydroxy-4-(methylthio)butanamide or a pharmaceutically acceptable salt thereof or solvate of the foregoing.

In some embodiments, the compound of formula (I) is 2-amino-4-(methylthio)butane-1-sulfonic acid, 2-formamido-4-(methylthio)butane-1-sulfonic acid; 1-amino-3-(methylthio)propane-1-sulfonic acid; 1-formamido-3-(methylthio)propane-1-sulfonic acid; 2-(2-aminoacetamido)-4-(methylthio)butane-1-sulfonic acid; or 2-(2-aminoacetamido)-N-hydroxy-4-(methylthio)butanamide.

In some embodiments, the compound of formula (I) is 2-amino-4-(methylthio)butane-1-sulfonic acid; 2-(2-aminoacetamido)-4-(methylthio)butane-1-sulfonic acid; or 2-(2-aminoacetamido)-N-hydroxy-4-(methylthio)butanamide.

In some embodiments, the compound of formula (I) is 2-amino-4-(methylthio)butane-1-sulfonic acid, 2-formamido-4-(methylthio)butane-1-sulfonic acid; 1-amino-3-(methylthio)propane-1-sulfonic acid; or 1-formamido-3-(methylthio)propane-1-sulfonic acid.

In some embodiments, the compound of formula (I) is 2-amino-4-(methylthio)butane-1-sulfonic acid. In some embodiments, the compound of formula (I) is 2-(2-aminoacetamido)-4-(methylthio)butane-1-sulfonic acid; or 2-(2-aminoacetamido)-N-hydroxy-4-(methylthio)butanamide. In some embodiments, the compound of formula (I) is 2-(2-aminoacetamido)-4-(methylthio)butane-1-sulfonic acid. In some embodiments, the compound of formula (I) is 2-(2-aminoacetamido)-N-hydroxy-4-(methylthio)butanamide.

In one aspect, the analog is a compound of the formula (II), (III), or (IV):

(II) [Structure with R1-NH, R3, R4, R5, R6, R7, R8, S substituents and SO3H group]

or (III) [Structure with R1-NH, R3, R4, R5, R6, R7, R8, S substituents and PO3H2 group]

or (IV) [Structure with R1-NH, R3, R4, R5, R6, R7, R8, S substituents and C(O)-NH-OH group]

wherein each $R^1$ is independently hydrogen, —C(O)R$^{12}$, —(B)$_w$—C, —OH, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

each $R^3$, $R^4$, $R^5$, $R^6$, and $R^7$ is independently hydrogen, halogen, —OR$^{13}$, —NO$_2$, —N(R$^{14}$)(R$^{15}$), —SO$_2$R$^{16}$, —SO$_2$N(R$^{17}$)(R$^{18}$), —SR$^{19}$, —C(O)R$^{20}$, —C(O)OR$^{21}$, —C(O)NHR$^{22}$, —NHC(O)R$^{23}$, —OC(O)R$^{24}$, —NHC(O)OR$^{25}$, —NHC(O)NHR$^{26}$, —OC(O)OR$^{27}$, —OC(O)NHR$^{28}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

each $R^8$, $R^{12}$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ is independently hydrogen, or an optionally substituted moiety from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

each $R^{16}$ is independently an optionally substituted moiety from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

each q is independently 1 or 2; and each t is independently 0 or 1;

each B and C is independently an optionally substituted amino acid moiety; and each w is independently 0, 1, or 2;

or a pharmaceutically acceptable salt thereof or solvate of the foregoing.

In some embodiments, the compound is of formula II only. In some embodiments, the compound is of formula III only. In some embodiments, the compound is of formula IV only.

In some embodiments, the compound of formula II has the proviso that when $R^1$, $R^3$, $R^4$, $R^5$, $R^6$, and $R^7$ is each hydrogen, and $R^8$ is methyl or benzyl, then t is 1. In some embodiments, the compound of formula II has the proviso that when $R^1$ is hydrogen, and $R^8$ is methyl or benzyl, then t is 1. In some embodiments, the compound of formula II has the proviso that when $R^1$ is hydrogen, and $R^8$ is an optionally substituted alkyl or an optionally substituted aralkyl, then t is 1. In some embodiments, the compound of formula II has the proviso when $R^1$ is hydrogen, and $R^8$ is an optionally substituted alkyl or an optionally substituted aralkyl, then t is 1.

In some embodiments of the compound of formula III, t is 1.

In some embodiments of the compound of formula IV, $R^1$ is other than H. In some embodiments of the compound of formula IV, $R^1$ is —C(O)R$^{12}$ (e.g., —C(O)H) or —(B)$_w$—C (e.g., $R^1$ is an optionally substituted amino acid moiety, such as

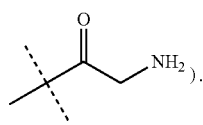

In some embodiments of the compound of formula IV, $R^1$ is —$(B)_w$—C (e.g., $R^1$ is an optionally substituted amino acid moiety, such as

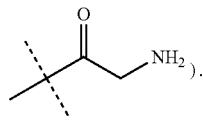

In some of these embodiments of the compound of formula II, III, or IV, each optionally substituted moiety is the indicated moiety optionally substituted with one or more groups selected from hydroxyl, nitro, amino, imino, cyano, halo, haloalkyl, thiol, thioalkyl, sulfonyl, thioamido, amidino, oxo, oxamidino, methoxamidino, imidino, guanidino, sulfonamido, carboxyl, formyl, alkyl, cycloalkyl, alkoxy, alkoxyalkyl, alkylcarbonyl, alkylcarbonyloxy, aminocarbonyl, aryl, heteroaryl, arylcarbonyl, aralkylcarbonyl, carbonylamino, heteroarylcarbonyl, heteroaralkyl-carbonyl, alkylthio, aminoalkyl, cyanoalkyl, carbamoyl, and urea. In some embodiments, each optionally substituted moiety is the indicated moiety optionally substituted with one or more groups selected from hydroxyl, nitro, amino, cyano, halo, haloalkyl, thiol, thioalkyl, sulfonyl, thioamido, amidino, carboxyl, formyl, alkyl, cycloalkyl, alkoxy, and alkoxy-alkyl.

In some of these embodiments of the compound of formula II, III, or IV, q is 1. In some embodiments, q is 2. In some embodiments, t is 0. In some embodiments, t is 1. In some embodiments, q is 1 and t is 0. In some embodiments, q is 1 and t is 1. In some embodiments, q is 2 and t is 0. In some embodiments, q is 2 and t is 1.

In some of these embodiments of the compound of formula II, III, or IV, each $R^1$ is independently hydrogen, —C(O)$R^{12}$, —OH, or an optionally substituted alkyl. In some embodiments, each $R^1$ is independently hydrogen or —C(O)$R^{12}$. In some embodiments, $R^1$ is hydrogen. In some embodiments, $R^1$ is —C(O)$R^{12}$ (e.g., —C(O)H). In some embodiments, each $R^{12}$ is independently hydrogen, or an optionally substituted alkyl. In some embodiments, $R^{12}$ is hydrogen.

In some of these embodiments of the compound of formula II, III, or IV, $R^1$ is —$(B)_w$—C. In some embodiments, the B moiety attached to $R^1$ is linked through an amide bond. In some embodiments, each B and C moiety is attached to its adjacent B or C moiety through an amide bond. In some embodiments, at least one B or C is an optionally substituted aliphatic amino acid moiety (e.g., glycine, valine, alanine, leucine, and isoleucine). In some embodiments, each B and C is an optionally substituted aliphatic amino acid moiety (e.g., glycine, valine, alanine, leucine, and isoleucine). In some embodiments, each B and C is selected from glycine and valine. In some embodiments, $R^1$ is selected from the group consisting of

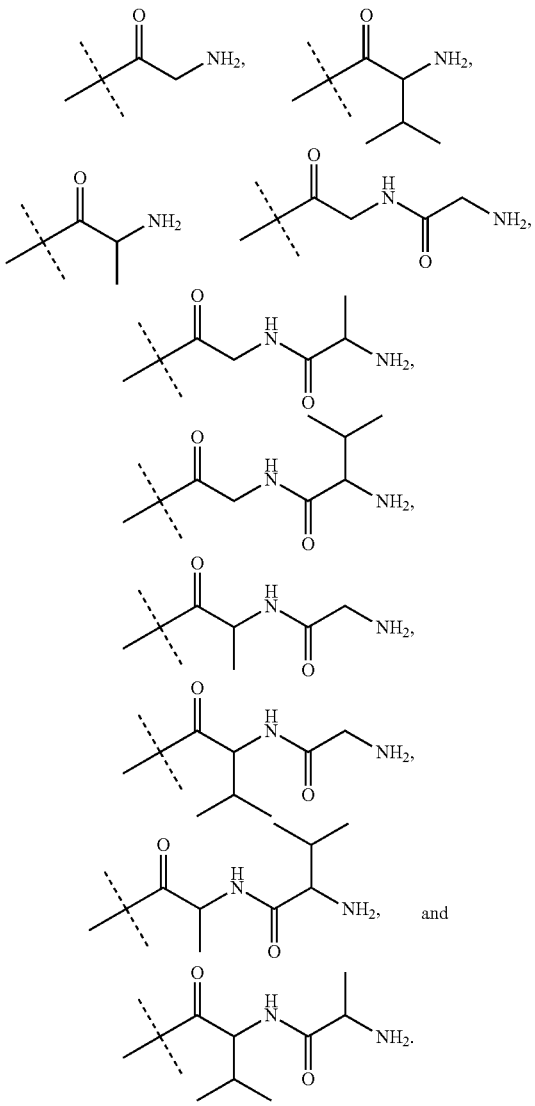

In some embodiments, $R^1$ is

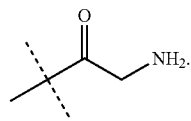

In some of these embodiments, w is 0. In some embodiments, w is 1. In other embodiments, w is 2. In some embodiments, at least one B or C amino acid is in the D form. In some embodiments, at least one B or C amino acid is in the L form. In some embodiments, each B and C amino acid is in the D form. In some embodiments, each B and C amino acid (e.g., gly-gly-) is in the L form.

In some of these embodiments of the compound of formula II, III, or IV, each $R^3$, $R^4$, $R^5$, $R^6$, and $R^7$ is independently hydrogen, halogen (e.g., Cl, F, I, Br), or —$OR^{13}$. In some embodiments, each $R^3$, $R^4$, $R^5$, $R^6$, and $R^7$ is independently hydrogen or halogen (e.g., Cl, F, I, Br). In some embodiments, $R^3$, $R^4$, $R^5$, $R^6$, and $R^7$ are hydrogen.

In some of these embodiments of the compound of formula II, III, or IV, each $R^8$ is independently an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl. In some embodiments, each $R^8$ is independently hydrogen or an optionally substituted alkyl. In some embodiments, $R^8$ is hydrogen. In some embodiments, each $R^8$ is independently an optionally substituted alkyl. In some embodiments, $R^8$ is an alkyl. In some embodiments, $R^8$ is a $C_1$-$C_5$ alkyl. In some embodiments, each $R^8$ is independently methyl or ethyl. In some embodiments, $R^8$ is methyl.

In some embodiments of the compound of formula II, $R^1$ is independently hydrogen or —C(O)H; each $R^3$, $R^4$, $R^5$, $R^6$, and $R^7$ is independently hydrogen or halogen (e.g., Cl, F, I, Br); each $R^8$ is independently hydrogen, or an optionally substituted moiety selected from alkyl, cycloalkyl, cycloalkyl-alkyl, heterocycloalkyl, heterocycloalkyl-alkyl, aryl, aralkyl, heteroaryl, and heteroaralkyl; with the proviso that when $R^1$ is hydrogen, and $R^8$ is alkyl or aralkyl, then t is 1; or a pharmaceutically acceptable salt thereof or solvate of the foregoing. In some of these embodiments, t is 0. In some embodiments, t is 1.

In some embodiments of the compound of formula II, $R^1$ is independently hydrogen or —C(O)H; each $R^3$, $R^4$, $R^5$, $R^6$, and $R^7$ is independently hydrogen or halogen (e.g., Cl, F, I, Br); and each $R^8$ is independently hydrogen or an optionally substituted alkyl (e.g., methyl or ethyl); with the proviso that when $R^1$ is hydrogen, and $R^8$ is alkyl, then t is 1; or a pharmaceutically acceptable salt thereof or solvate of the foregoing. In some of these embodiments, t is 0. In some embodiments, t is 1.

In some embodiments of the compound of formula III, $R^1$ is independently hydrogen or —C(O)H; each $R^3$, $R^4$, $R^5$, $R^6$, and $R^7$ is independently hydrogen or halogen (e.g., Cl, F, I, Br); each $R^8$ is independently hydrogen, or an optionally substituted moiety selected from alkyl, cycloalkyl, cycloalkyl-alkyl, heterocycloalkyl, heterocycloalkyl-alkyl, aryl, aralkyl, heteroaryl, and heteroaralkyl; and t is 1; or a pharmaceutically acceptable salt thereof or solvate of the foregoing. In some of these embodiments, q is 1. In some embodiments, q is 2.

In some embodiments of the compound of formula III, $R^1$ is independently hydrogen or —C(O)H; each $R^3$, $R^4$, $R^5$, $R^6$, and $R^7$ is independently hydrogen or halogen (e.g., Cl, F, I, Br); each $R^8$ is independently hydrogen or an optionally substituted alkyl (e.g., methyl or ethyl); and t is 1; or a pharmaceutically acceptable salt thereof or solvate of the foregoing. In some of these embodiments, q is 1. In some embodiments, q is 2.

In some embodiments of the compound of formula IV, $R^1$ is independently hydrogen or —C(O)H; each $R^3$, $R^4$, $R^5$, $R^6$, and $R^7$ is independently hydrogen or halogen (e.g., Cl, F, I, Br); each $R^8$ is independently hydrogen, or an optionally substituted moiety selected from alkyl, cycloalkyl, cycloalkyl-alkyl, heterocycloalkyl, heterocycloalkyl-alkyl, aryl, aralkyl, heteroaryl, and heteroaralkyl; or a pharmaceutically acceptable salt thereof or solvate of the foregoing. In some of these embodiments, t is 0. In some embodiments, t is 1.

In some embodiments of the compound of formula IV, $R^1$ is independently hydrogen or —C(O)H; each $R^3$, $R^4$, $R^5$, $R^6$, and $R^7$ is independently hydrogen or halogen (e.g., Cl, F, I, Br); and each $R^8$ is independently hydrogen or an optionally substituted alkyl (e.g., methyl or ethyl); or a pharmaceutically acceptable salt thereof or solvate of the foregoing. In some of these embodiments, t is 0. In some embodiments, t is 1.

In some embodiments of the compound of formula IV, $R^1$ is —C(O)H or —(B)$_w$—C (e.g., $R^1$ is an optionally substituted amino acid moiety, such as

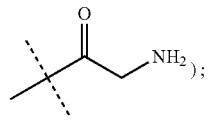

each $R^3$, $R^4$, $R^5$, $R^6$, and $R^7$ is independently hydrogen or halogen (e.g., Cl, F, I, Br); each $R^8$ is independently hydrogen, or an optionally substituted moiety selected from alkyl, cycloalkyl, cycloalkyl-alkyl, heterocycloalkyl, heterocycloalkyl-alkyl, aryl, aralkyl, heteroaryl, and heteroaralkyl; or a pharmaceutically acceptable salt thereof or solvate of the foregoing. In some of these embodiments, t is 0. In some embodiments, t is 1.

In some embodiments of the compound of formula IV, $R^1$ is —C(O)H or —(B)$_w$—C (e.g., $R^1$ is an optionally substituted amino acid moiety, such as

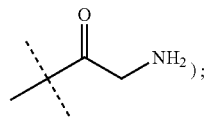

each $R^3$, $R^4$, $R^5$, $R^6$, and $R^7$ is independently hydrogen or halogen (e.g., Cl, F, I, Br); and each $R^8$ is independently hydrogen or an optionally substituted alkyl (e.g., methyl or ethyl); or a pharmaceutically acceptable salt thereof or solvate of the foregoing. In some of these embodiments, t is 0. In some embodiments, t is 1.

In some embodiments of the compound of formula IV, $R^1$ is —(B)$_w$—C (e.g., $R^1$ is an optionally substituted amino acid moiety, such as

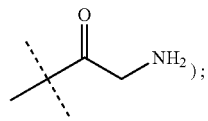

each $R^3$, $R^4$, $R^5$, $R^6$, and $R^7$ is independently hydrogen or halogen (e.g., Cl, F, I, Br); and each $R^8$ is independently hydrogen or an optionally substituted alkyl (e.g., methyl or ethyl); or a pharmaceutically acceptable salt thereof or solvate of the foregoing. In some of these embodiments, t is 0. In some embodiments, t is 1.

In another aspect, the analog is a compound of the formula (V), (VI), or (VII):

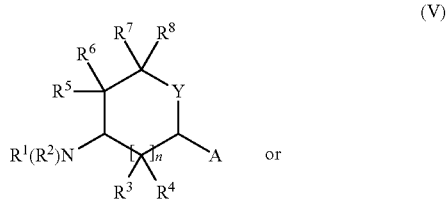

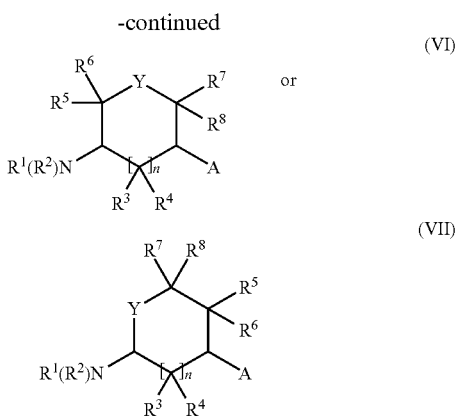

wherein

A is —SO$_3$H, —SO$_2$R$^9$, —SO$_2$N(R$^{10}$)(R$^{11}$), —PO$_3$H$_2$, —PO$_4$H$_2$ or —C(O)NHOH;

Y is S or O;

R$^1$ is hydrogen, —C(O)R$^{12}$, —(B)$_w$—C, —OH, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

R$^2$ is hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

or wherein R$^1$ and R$^2$ are taken together to form an optionally substituted 5 or 6-membered heterocyclic ring containing the nitrogen to which they are attached;

each R$^3$, R$^4$, R$^5$, R$^6$, R$^7$, and R$^8$ is independently hydrogen, halogen, —OR$^{13}$, —NO$_2$, —N(R$^{14}$)(R$^{15}$), —SO$_2$R$^{16}$, —SO$_2$N(R$^{17}$)(R$^{18}$), —SR$^{19}$, —C(O)R$^{20}$, —C(O)OR$^{21}$, —C(O)NHR$^{22}$, —NHC(O)R$^{23}$, —OC(O)R$^{24}$, —NHC(O)OR$^{25}$, —NHC(O)NHR$^{26}$, —OC(O)OR$^{27}$, —OC(O)NHR$^{28}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

R$^{10}$, R$^{11}$, R$^{12}$, R$^{13}$, R$^{14}$, R$^{15}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, and R$^{28}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

R$^9$ and R$^{16}$ are independently an optionally substituted moiety selected from alkyl, alkenyl, alkynyl, cycloalkyl, cycloalkyl-alkyl, heterocycloalkyl, eterocycloalkyl-alkyl, aryl, aralkyl, heteroaryl, heteroaralkyl;

n is 0 or 1;

each B and C is an optionally substituted amino acid moiety; and w is 0, 1, or 2;

or a pharmaceutically acceptable salt thereof or solvate of the foregoing.

In some of these embodiments of the compound of formula V, VI, or VII, each optionally substituted moiety is the indicated moiety optionally substituted with one or more groups selected from hydroxyl, nitro, amino, imino, cyano, halo, haloalkyl, thiol, thioalkyl, sulfonyl, thioamido, amidino, oxo, oxamidino, methoxamidino, imidino, guanidino, sulfonamido, carboxyl, formyl, alkyl, cycloalkyl, alkoxy, alkoxy-alkyl, alkylcarbonyl, alkylcarbonyloxy, aminocarbonyl, aryl, heteroaryl, arylcarbonyl, aralkylcarbonyl, carbonylamino, heteroarylcarbonyl, heteroaralkyl-carbonyl, alkylthio, aminoalkyl, cyanoalkyl, carbamoyl, and urea. In some embodiments, each optionally substituted moiety is the indicated moiety optionally substituted with one or more groups selected from hydroxyl, nitro, amino, cyano, halo, haloalkyl, thiol, thioalkyl, sulfonyl, thioamido, amidino, carboxyl, formyl, alkyl, cycloalkyl, alkoxy, and alkoxy-alkyl.

In some of these embodiments of the compound of formula V, VI, or VII, A is —SO$_3$H, —SO$_2$R$^9$, —SO$_2$N(R$^{10}$)(R$^{11}$), —PO$_3$H$_2$, or —C(O)NHOH; Y is S or O; R$^1$ is hydrogen, —C(O)R$^{12}$, —(B)$_w$—C, —OH, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; R$^2$ is hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; or wherein R$^1$ and R$^2$ are taken together to form an optionally substituted 5 or 6-membered heterocyclic ring containing the nitrogen to which they are attached; each R$^3$, R$^4$, R$^5$, R$^6$, R$^7$, and R$^8$ is independently hydrogen, halogen, —OR$^{13}$, —NO$_2$, —N(R$^{14}$)(R$^{15}$), —SO$_2$R$^{16}$, —SO$_2$N(R$^{17}$)(R$^{18}$), —SR$^{19}$, —C(O)R$^{20}$, —C(O)OR$^{21}$, —C(O)NHR$^{22}$, —NHC(O)R$^{23}$, —OC(O)R$^{24}$, —NHC(O)OR$^{25}$, —NHC(O)NHR$^{26}$, —OC(O)OR$^{27}$, —OC(O)NHR$^{28}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; R$^{10}$, R$^{11}$, R$^{12}$, R$^{13}$, R$^{14}$, R$^{15}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, and R$^{28}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl; R$^9$ and R$^{16}$ are independently an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, heteroaralkyl; n is 0 or 1; each B and C is an optionally substituted amino acid moiety; and w is 0, 1, or 2; or a pharmaceutically acceptable salt thereof or solvate of the foregoing.

In some of these embodiments of the compound of formula V, VI, or VII, A is —SO$_3$H, —SO$_2$R$^9$, —SO$_2$N(R$^{10}$)(R$^{11}$) or —PO$_3$H$_2$. In some embodiments, A is —SO$_3$H, —SO$_2$R$^9$, —SO$_2$N(R$^{10}$)(R$^{11}$), —PO$_3$H$_2$, or —C(O)NHOH. In some embodiments, A is —SO$_3$H or —PO$_3$H$_2$. In some embodiments, A is —PO$_3$H$_2$ or —PO$_3$H$_2$. In some embodiments, A is —PO$_3$H$_2$. In some embodiments, A is —PO$_4$H$_2$. In some embodiments, A is —SO$_3$H.

In some of these embodiments of the compound of formula V, VI, or VII, Y is S. In some embodiments, Y is O.

In some of these embodiments of the compound of formula V, VI, or VII, n is 1. In some embodiments, n is 0.

In some of these embodiments of the compound of formula V, VI, or VII, each R$^1$ is independently hydrogen, —C(O)R$^{12}$, —OH, or an optionally substituted alkyl. In some embodiments, each R$^1$ is independently hydrogen or —C(O)R$^{12}$. In some embodiments, R$^1$ is hydrogen. In some embodiments, R$^1$ is —C(O)R$^{12}$. In some embodiments, each R$^{12}$ is independently hydrogen, or an optionally substituted alkyl. In some embodiments, R$^{12}$ is hydrogen.

In some of these embodiments of the compound of formula V, VI, or VII, R$^1$ is —(B)$_w$—C. In some embodiments, the B moiety attached to R$^1$ is linked through an amide bond. In some embodiments, each B and C moiety is attached to its adjacent B or C moiety through an amide bond. In some embodiments, at least one B or C is an optionally substituted aliphatic amino acid moiety (e.g., glycine, valine, alanine, leucine, and isoleucine). In some embodiments, each B and C is an optionally substituted aliphatic amino acid moiety (e.g., glycine, valine, alanine, leucine, and isoleucine). In some embodiments, each B and C is selected from glycine and valine. In some embodiments, $R^1$ is selected from the group consisting of

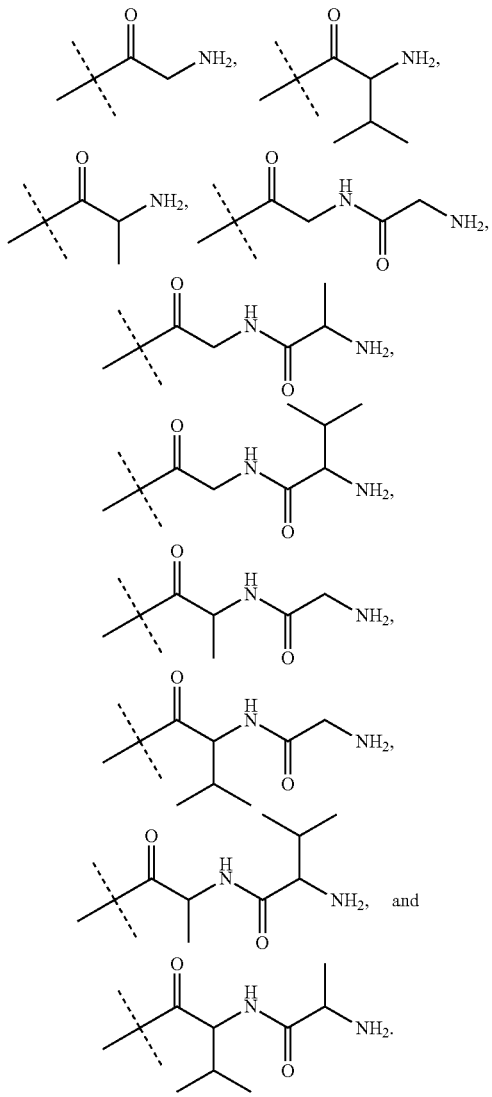

In some of these embodiments, $R^2$ is H. In some embodiments, $R^1$ is

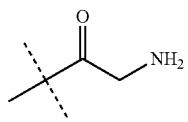

and $R^2$ is H. In some of these embodiments, w is 0. In some embodiments, w is 1. In other embodiments, w is 2. In some embodiments, at least one B or C amino acid is in the D form. In some embodiments, at least one B or C amino acid is in the L form. In some embodiments, each B and C amino acid is in the D form. In some embodiments, each B and C amino acid (e.g., gly-gly-) is in the L form.

In some of these embodiments of the compound of formula V, VI, or VII, each $R^3$, $R^4$, $R^5$, $R^6$, $R^7$, and $R^8$ is independently hydrogen, halogen (e.g., Cl, F, I, Br), optionally substituted alkyl, or $-OR^{13}$. In some embodiments, each $R^3$, $R^4$, $R^5$, $R^6$, $R^7$, and $R^8$ is independently hydrogen, halogen (e.g., Cl, F, I, Br), or alkyl optionally substituted with one or more halogen groups (e.g., Cl, F, I, Br). In some embodiments, $R^3$, $R^4$, $R^5$, $R^6$, $R^7$, and $R^8$ are hydrogen. In some embodiments, at least one of $R^5$, $R^6$, $R^7$, or $R^8$ is an optionally substituted alkyl (e.g., alkyl optionally substituted with one or more halogen groups). In some embodiments, one of $R^5$, $R^6$, $R^7$, or $R^8$ is an optionally substituted alkyl (e.g., alkyl optionally substituted with one or more halogen groups) and the others of $R^5$, $R^6$, $R^7$, or $R^8$ are hydrogen. In some embodiments, the optionally substituted alkyl is a methyl or ethyl group optionally substituted with one or more halogen groups (e.g., $-CF_3$, $-CH_2CF_3$).

In some of these embodiments of the compound of formula V, VI, or VII, $R^7$ is independently an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl. In some embodiments, each $R^7$ is independently hydrogen or an optionally substituted alkyl (e.g., optionally substituted with halogen). In some embodiments, each $R^7$ is independently an optionally substituted alkyl (e.g., $-CF_3$, $-CH_2CF_3$). In some embodiments, $R^7$ is an alkyl. In some embodiments, $R^7$ is a $C_1$-$C_5$ alkyl. In some embodiments, each $R^7$ is independently methyl or ethyl (or an optionally substituted methyl or ethyl). In some embodiments, $R^7$ is methyl.

In some embodiments of the compound of formula V, VI, or VII, $R^1$ is independently hydrogen or $-C(O)H$; $R^2$ is H; each $R^3$, $R^4$, $R^5$, $R^6$, and $R^7$ is independently hydrogen or halogen (e.g., Cl, F, I, Br); $R^8$ is hydrogen, or an optionally substituted moiety selected from alkyl, cycloalkyl, cycloalkyl-alkyl, heterocycloalkyl, heterocycloalkyl-alkyl, aryl, aralkyl, heteroaryl, and heteroaralkyl; or a pharmaceutically acceptable salt thereof or solvate of the foregoing. In some of these embodiments, A is $-SO_3H$, $-PO_3H_2$, or $-C(O)NHOH$, and t is 0. In some of these embodiments, A is $-SO_3H$, $-PO_3H_2$, or $-C(O)NHOH$, and t is 1. In some of these embodiments, Y is S. In some embodiments, Y is O.

In some embodiments of the compound of formula V, VI, or VII, $R^1$ is independently hydrogen or $-C(O)H$; $R^2$ is H; each $R^3$, $R^4$, $R^5$, $R^6$, and $R^7$ is independently hydrogen or halogen (e.g., Cl, F, I, Br); and $R^8$ is hydrogen or an optionally substituted alkyl (e.g., methyl or ethyl); or a pharmaceutically acceptable salt thereof or solvate of the foregoing. In some of these embodiments, A is $-SO_3H$, $-PO_3H_2$, or $-C(O)NHOH$, and t is 0. In some of these embodiments, A is $-SO_3H$, $-PO_3H_2$, or $-C(O)NHOH$, and t is 1. In some of these embodiments, Y is S. In some embodiments, Y is O.

In some embodiments of the compound of formula V, VI, or VII, $R^1$ is independently hydrogen or $-C(O)H$; $R^2$ is H; each $R^3$, $R^4$, $R^5$, $R^6$, and $R^7$ is independently hydrogen or halogen (e.g., Cl, F, I, Br); $R^8$ is hydrogen or an optionally substituted alkyl (e.g., methyl or ethyl, optionally substituted with one or more halogen groups); A is $-SO_3H$, and t is 1; or a pharmaceutically acceptable salt thereof or solvate of the foregoing. In some embodiments, $R^1$ is independently hydrogen or $-C(O)H$; $R^2$ is H; each $R^3$, $R^4$, $R^5$, $R^6$, and $R^7$ is independently hydrogen or halogen (e.g., Cl, F, I, Br); $R^8$ is hydrogen or an optionally substituted alkyl (e.g., methyl or ethyl, optionally substituted with one or more halogen groups); A is —PO$_3$H$_2$, and t is 1; or a pharmaceutically acceptable salt thereof or solvate of the foregoing.

In some embodiments, the compound of formula (V) is the compound:

(V-A):

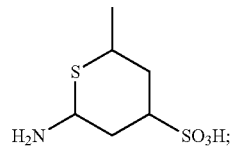

2-amino-6-methyltetrahydro-2H-thiopyran-4-sulfonic acid (V-B):

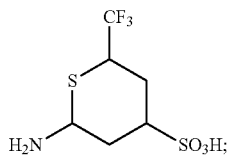

2-amino-6-(trifluoromethyl)tetrahydro-2H-thiopyran-4-sulfonic acid (V-C):

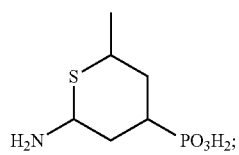

2-amino-6-methyltetrahydro-2H-thiopyran-4-ylphosphonic acid (V-D):

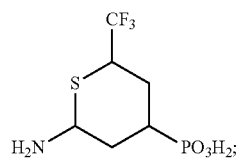

2-amino-6-(trifluoromethyl)tetrahydro-2H-thiopyran-4-ylphosphonic acid or a pharmaceutically acceptable salt thereof or solvate of the foregoing.

In some embodiments, the compound of formula (VI) is the compound:

(VI-A):

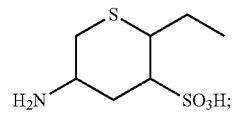

5-amino-2-ethyltetrahydro-2H-thiopyran-3-sulfonic acid (VI-B):

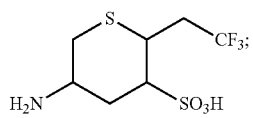

5-amino-2-(2,2,2-trifluoroethyl)tetrahydro-2H-thiopyran-3-sulfonic acid (VI-C):

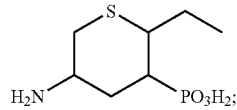

5-amino-2-ethyltetrahydro-2H-thiopyran-3-ylphosphonic acid (VI-D):

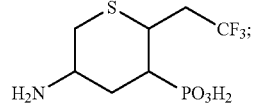

5-amino-2-(2,2,2-trifluoroethyl)tetrahydro-2H-thiopyran-3-ylphosphonic acid (VI-E):

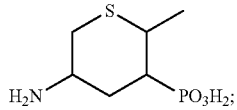

5-amino-2-methyltetrahydro-2H-thiopyran-3-ylphosphonic acid or a pharmaceutically acceptable salt thereof or solvate of the foregoing.

In some embodiments, the compound of formula (VII) is the compound:

(VII-A):

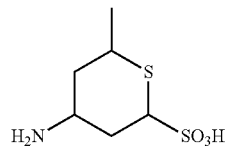

4-amino-6-methyltetrahydro-2H-thiopyran-2-sulfonic acid;

(VII-B):

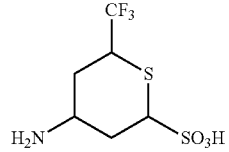

4-amino-6-(trifluoromethyl)tetrahydro-2H-thiopyran-2-sulfonic acid;

(VII-C):

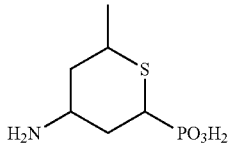

4-amino-6-methyltetrahydro-2H-thiopyran-2-ylphosphonic acid;

(VII-D):

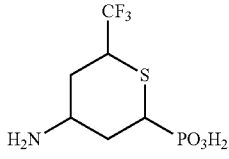

4-amino-6-(trifluoromethyl)tetrahydro-2H-thiopyran-2-ylphosphonic acid;

or a pharmaceutically acceptable salt thereof or solvate of the foregoing.

In some embodiments, the analogs described herein (e.g., any compound of formula I, II, III, IV, V, VI, or VII) is in substantially pure form. Unless otherwise stated, "substantially pure" intends a preparation of the analog that contains no more than 15% impurity, wherein the impurity intends compounds other than the analog, but does not include other forms of the analog (e.g., different salt form or a different stereoisomer, conformer, rotamer, or tautomer of the analog depicted). In one variation, a preparation of substantially pure analog is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

The analogs described herein (e.g., any compound of formula I, II, III, IV, V, VI, or VII) and methods of using the same, unless otherwise stated, include all solvate and/or hydrate forms. In some embodiments, the analogs described herein can exist in unsolvated forms as well as solvated forms (i.e., solvates). The analogs may also include hydrated forms (i.e., hydrates).

The analogs described herein (e.g., any compound of formula I, II, III, IV, V, VI, or VII), as well as methods of using such salts of the analogs, unless otherwise stated, include all salt forms of the analogs. The analogs also include all non-salt forms of any salt of an analog described herein, as well as other salts of any salt of an analog described herein. In some embodiments, the salts of the analogs are pharmaceutically acceptable salts. "Pharmaceutically acceptable salts" are those salts which retain the biological activity and which can be administered as drugs or pharmaceuticals to and individual (e.g., a human). The desired salt of a basic functional group of a compound may be prepared by methods known to those of skill in the art by treating the compound with an acid. The desired salt of an acidic functional group of a compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, bismuth salts, and calcium salts; ammonium salts; and aluminum salts. Examples of organic salts of acid compounds include, but are not limited to, procaine, dibenzylamine, N-ethylpiperidine, N,N'-dibenzylethylenediamine, trimethylamine, and triethylamine salts. Examples of inorganic salts of base compounds include, but are not limited to, hydrochloride and hydrobromide salts. Examples of organic salts of base compounds include, but are not limited to, tartrate, citrate, maleate, fumarate, and succinate.

Unless stereochemistry is explicitly indicated in a chemical structure or chemical name, the chemical structure or chemical name is intended to embrace all possible stereoisomers, conformers, rotamers, and tautomers of the analogs depicted. For example, an analog containing a chiral carbon atom is intended to embrace both the (R) enantiomer and the (S) enantiomer, as well as mixtures of enantiomers, including racemic mixtures; and a compound containing two chiral carbons is intended to embrace all enantiomers and diastereomers (including (R,R), (S,S), (R,S), and (R,S) isomers). In some embodiments, an analog described herein (e.g., any compound of formula I, II, III, IV, V, VI, or VII) is in the form of the (R) enantiomer. In some embodiments, an analog described herein (e.g., any compound of formula I, II, III, IV, V, VI, or VII) is in the form of the (S) enantiomer.

Included in all uses of the analogs disclosed herein, is any or all of the stereochemical, enantiomeric, diastereomeric, conformational, rotameric, tautomeric, solvate, hydrate, salt, and pharmaceutically acceptable salt of the analogs as described.

Synthetic Methods

The analogs described may be prepared using the teachings herein, as well as with certain methods known in the art (e.g., Suchata Jinachitra and A. J. MacLeod 1978: A synthesis of alpha-Aminosulphonic Acids. Tetrahedron Vol. 35: 1315-1316). The discussion below is offered to illustrate certain methods for use in assembling the analogs and is not intended to limit the scope of the reactions or reaction sequences and/or conditions that are useful in preparing the analogs.

Some target analogs described herein may be synthesized by starting with a Boc-protected aminoalcohol, as shown below in Scheme I. The alcohol is converted to the mesylate ester by treatment with methanesulfonyl chloride in the presence of a base (e.g., an amine, such as triethylamine) in a suitable solvent (e.g., dichloromethane). Alternatively, the mesylate ester is generated from the alcohol by treatment with methanesulfonic anhydride in the presence of base. The mesylate is then converted to the Boc-protected sulfonic acid by treatment with sodium sulphate in a suitable solvent (e.g., a co-solvent, such as ethanol/water), then deprotected using a strong acid (e.g., hydrochloric acid) to provide the desired analog.

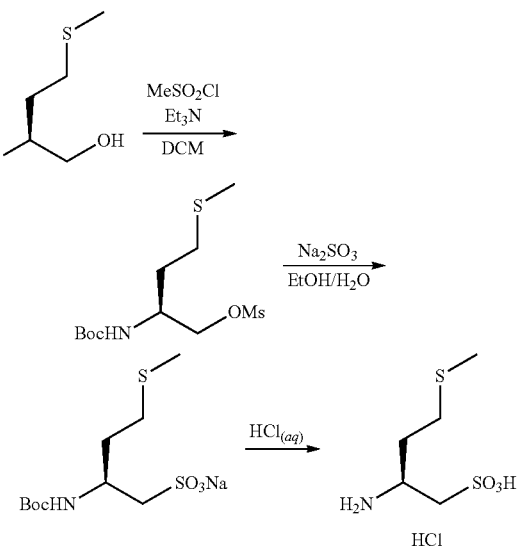

Scheme I

Certain analogs may be further coupled to one or more amino acid moieties (e.g., a glycine) as exemplified for the synthesis of (S)-2-(2-aminoacetamido)-4-(methylthio)butane-1-sulfonic acid shown in Scheme II. An unprotected amine of a methionine analog (e.g., sodium (S)-2-amino-4-(methylthio)butane-1-sulfonate as described above in Scheme I) may be coupled in a suitable solvent in the presence of base to the desired monomer (or dimer, trimer, etc., as appropriate), wherein the amino acid carboxylate is activated (e.g., as a succinimidyl ester).

Scheme II

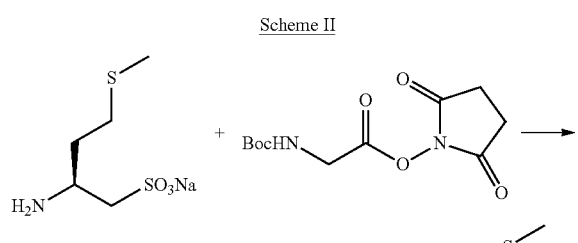

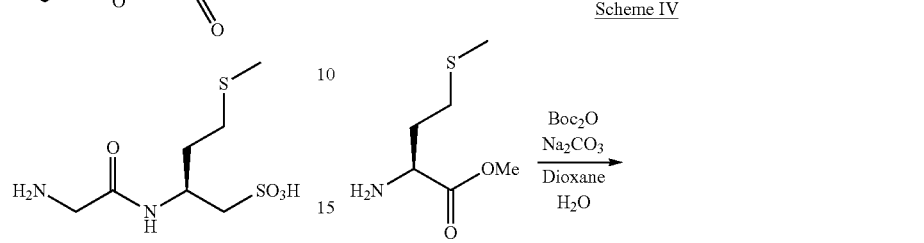

Some target analogs comprising a formamide moiety as described herein may be synthesized by starting with an unprotected, natural or unnatural amino acid, as shown below in Scheme III.

Scheme III

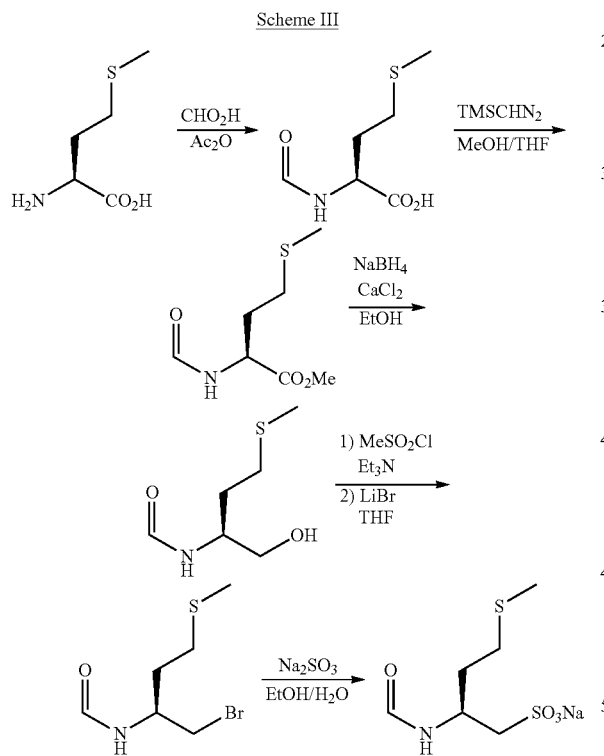

The primary amine is formylated by treatment with formic acid in the presence of acetic anhydride. The carboxylate is then converted to the methyl ester with e.g., (trimethylsilyl) diazomethane, which is then reduced using any number of standard reducing agents (e.g., sodium borohydride). The primary alcohol is converted to the mesylate ester as described above in scheme I, followed by transformation into the bromide by treatment with LiBr. The desired analog is then generated by treatment with sodium sulphate, as described above.

Some target analogs comprising a hydroxyamide moiety as described herein may be synthesized by starting with an ester protected analog, as shown below in Scheme IV. The primary amide may be Boc-protected (e.g., using boc anhydride in a suitable solvent, such as dioxane/H$_2$O, in the presence of base, such as Na$_2$CO$_3$), then treated with hydroxylamine in a suitable solvent (e.g., dioxane/H$_2$O). Removal of the Boc protecting group provides the desired hydroxyamide analog.

Scheme IV

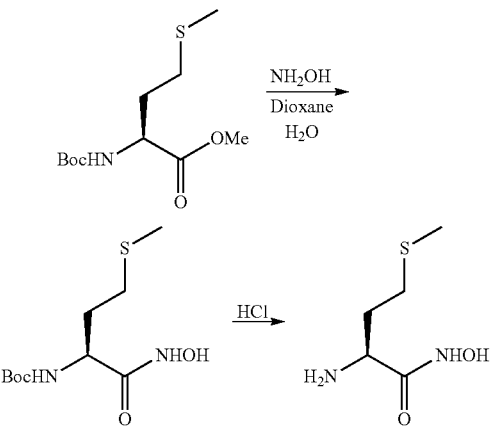

As described above, certain analogs may be further coupled to one or more amino acid moieties (e.g., one or more glycine moieties). The coupling of an amino acid may occur at any stage appropriate for the synthesis of the desired analog product. Scheme V below demonstrates first coupling of a boc-protected amino acid glycine to a methionine analog (e.g., using an appropriate coupling agent such as DCC and a mild base) followed by hydroxyamide formation using treatment with hydroxylamine as described above. Removal of the Boc protecting group provides the desired hydroxyamide analog.

Scheme V

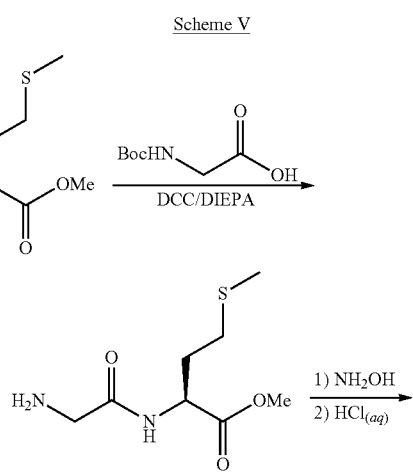

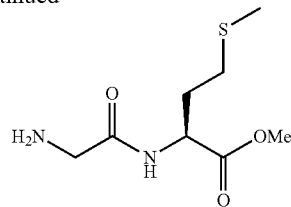

In one aspect is provided a process for preparing a compound of formula (I):

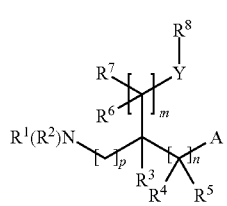

wherein
A is —SO$_3$H, —SO$_2$R$^9$, —SO$_2$N(R$^{10}$)(R$^{11}$), —PO$_3$H$_2$, or —C(O)NHOH;

Y is S or O;

R$^1$ is hydrogen, —C(O)R$^{12}$, —(B)$_w$—C, —OH, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

R$^2$ is hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

or wherein R$^1$ and R$^2$ are taken together to form an optionally substituted 5 or 6-membered heterocyclic ring containing the nitrogen to which they are attached;

each R$^3$, R$^4$, R$^5$, R$^6$, and R$^7$ is independently hydrogen, halogen, —OR$^{13}$, —NO$_2$, —N(R$^{14}$)(R$^{15}$), —SO$_2$R$^{16}$, —SO$_2$N(R$^{17}$)(R$^{18}$), —SR$^{19}$, —C(O)R$^{20}$, —C(O)OR$^{21}$, —C(O)NHR$^{22}$, —NHC(O)R$^{23}$, —OC(O)R$^{24}$, —NHC(O)OR$^{25}$, —NHC(O)NHR$^{26}$, —OC(O)OR$^{27}$, —OC(O)NHR$^{28}$, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

R$^8$, R$^{10}$, R$^{11}$, R$^{12}$, R$^{13}$, R$^{14}$, R$^{15}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, and R$^{28}$ are independently hydrogen, or an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, and heteroaralkyl;

R$^9$ and R$^{16}$ are independently an optionally substituted moiety selected from alkyl, alkenyl, alkynyl, cycloalkyl, cycloalkyl-alkyl, heterocycloalkyl, heterocycloalkyl-alkyl, aryl, aralkyl, heteroaryl, heteroaralkyl;

m, n, and p are independently 0, 1, 2, 3, or 4;

each B and C is an optionally substituted amino acid moiety; and w is 0, 1, or 2;

or a pharmaceutically acceptable salt thereof or solvate of the foregoing;

comprising
(a) reacting a compound of formula SI-A:

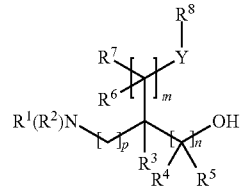

wherein, R$^1$, R$^2$, R$^3$, R$^4$, R$^5$, R$^6$, R$^7$, R$^8$, p, and n are as defined above; or a pharmaceutically acceptable salt thereof or solvate of the foregoing;
and a MsCl or methanesulfonic anhydride in a suitable solvent to form a compound of SI-B:

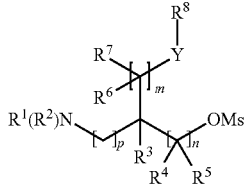

wherein, R$^1$, R$^2$, R$^3$, R$^4$, R$^5$, R$^6$, R$^7$, R$^8$, p, and n are as defined above; or a pharmaceutically acceptable salt thereof or solvate of the foregoing; and
(b) reacting the compound of formula SI-B with X-A in a suitable solvent, wherein X is one or more cationic groups and A is as defined above.

In some embodiments of step (a) for the process for preparing a compound of formula I, compound SI-A is reacted with MsCl in a suitable solvent (e.g., THF or a chlorinated solvent, such as dichloromethane) in the presence of a base (e.g., an amine base, such as triethylamine). In some embodiments of step (b) for the process for preparing a compound of formula I, compound SI-B is reacted with X-A, wherein X is a alkaline or alkaline earth metal (e.g., Na$^+$, K$^+$, or Ca$^{2+}$) in a suitable solvent (e.g., an alcohol, such as EtOH). In some embodiments, X-A is Na$_2$SO$_3$. In some embodiments, the process comprises (e.g., following step (a)) forming the intermediate compound SI-A2:

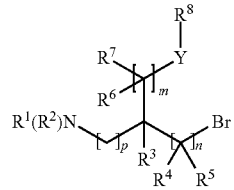

wherein, R$^1$, R$^2$, R$^3$, R$^4$, R$^5$, R$^6$, R$^7$, R$^8$, p, and n are as defined above; or a
pharmaceutically acceptable salt thereof or solvate of the foregoing;
prior to forming compound SI-B. In some embodiments, the intermediate compound SI-A2 is formed following the addition of a brominating agent (e.g., LiBr).

Process for Preparing a Compound of Formula (I)

The compound of formula (I) shown in the process for preparing a compound of formula (I) may include any one or more of the embodiments described herein for formula (I), including any one or more provisos of described formula (I).

Formulations

The analogs described herein (e.g., any compound of formula I, II, III, IV, V, VI, or VII) may be used in the preparation of a formulation, such as a pharmaceutical composition or formulation, by combining the analog(s) described with a pharmaceutical acceptable carrier, excipients, stabilizing agents and/or other agents, which are known in the art, for use in the methods of treatment, methods of administration, and dosage regimes described herein. The formulations may vary or be tailored according to the condition to be treated, the amount of compound to be administered, the condition of the individual, and other variables that will readily be apparent to one of ordinary skill in the art in view of the teachings provided herein. The analogs may be formulated, for example, as a solid, semi-solid, and liquid dosage forms, such as tablets, pills, powders, liquid solutions, aerosols, or suspensions, suppositories, injectable and infusible solutions, foams, gels, and sprays. The preferred form depends on the intended mode of administration and therapeutic application. The following formulations, additives, and methods are merely exemplary and are in no way limiting.

Additives used with the analogs described herein (e.g., any compound of formula I, II, III, IV, V, VI, or VII) include, for example, one or more excipients (e.g., one or more excipients), antioxidants (e.g., one or more antioxidants), stabilizers (e.g., one or more stabilizers), preservatives (e.g., one or more preservatives), pH adjusting and buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents, viscosity-increasing agents (e.g., one or more viscosity-increasing agents), and the like, either alone or together with one or more additional pharmaceutical agents, provided that the additional components are pharmaceutically acceptable for the particular condition to be treated (e.g., an infection). In some embodiments, the formulation may include combinations of two or more of the additional components as described herein (e.g., 2, 3, 4, 5, 6, 7, 8, or more additional components). In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Marck Pub. Co., New Jersey 18$^{th}$ edition (1996), and REMINGTON: THE SCIENCE AND PRACTICE OF PHARMACY, Lippincott Williams & Wilkins, Philadelphia, 20$^{th}$ edition (2003) and 21$^{st}$ edition (2005), the contents of which are hereby incorporated by reference in their entireties.

Formulations suitable for oral administration may comprise, for example, (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, (d) suitable emulsions, and (e) powders. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The analogs can be enclosed in a hard or soft capsule, can be compressed into tablets, or can be incorporated with beverages or food or otherwise incorporated into the diet. Capsules can be formulated by mixing the analog with an inert pharmaceutical diluent and inserting the mixture into a hard gelatin capsule of the appropriate size. If soft capsules are desired, a slurry of the analog with an acceptable vegetable oil, light petroleum or other inert oil can be encapsulated by machine into a gelatin capsule.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The formulations can be presented in unit-dose or multi-dose sealed containers, such as ampules and vials, and can be stored in a freeze-dried (lyophilized) condition requiring only the addition of the sterile liquid excipient methods of treatment, methods of administration, and dosage regimes described herein (i.e., water) for injection, immediately prior to use. Extemporaneous injection solutions and suspensions can be prepared from sterile powders, granules, and tablets of the kind previously described.

Formulation of the analog(s) in liquid form (for oral administration, parenteral administration, or otherwise) may have a pH in the range of about 4.5 to about 9.0, including for example pH ranges of any of about 5.0 to about 8.0, about 6.5 to about 7.5, and about 6.5 to about 7.0. In some embodiments, the pH of the formulation is formulated to no less than about 6, including for example no less than about any of 6.5, 7, or 8 (e.g., about 8). The formulation can also be made to be isotonic with blood by the addition of a suitable tonicity modifier, such as glycerol.

The analogs may also be formulated for administration by inhalation. Formulations suitable for aerosol administration which comprise the analog may include, for example, aqueous and non-aqueous, isotonic sterile solutions, which can contain anti-oxidants, buffers, bacteriostats, and solutes, as well as aqueous and non-aqueous sterile suspensions that can include suspending agents, solubilizers, thickening agents, stabilizing agents, and preservatives, alone or in combination with other suitable components, which can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

The analogs may also be formulated for topical administration, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches or impregnated sutures may also be used.

Also provided are unit dosage forms comprising the formulations described herein. These unit dosage forms can be stored in a suitable packaging in single or multiple unit dosages and may also be further sterilized and sealed. For example, the pharmaceutical formulation (e.g., a dosage or unit dosage form of a pharmaceutical formulation) may include (i) an analog (e.g., any compound of formula I, II, III, IV, V, VI, or VII) and (ii) a pharmaceutically acceptable carrier. In some embodiments, the pharmaceutical formulation also includes one or more other compounds (or pharmaceutically acceptable salts thereof) that are useful for treating an infection. In various variations, the amount of analog in the formulation is included in any of the following ranges: about 5 to about 50 mg, about 20 to about 50 mg, about 50 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of analog in the formulation (e.g., a dosage or unit dosage form) is in the range of about 5 mg to about 500 mg, such as about 30 mg to about 300 mg or about 50 mg to about 200 mg, of the analog. In some embodiments, the carrier is suitable for parental administration (e.g., intravenous administration). In some embodiments, the analog is the only pharmaceutically active agent for the treatment of an infection that is contained in the formulation.

In some embodiments, are provided dosage forms (e.g., a unit dosage form) for the treatment of an infection comprising (i) an analog described herein (e.g., any compound of formula I, II, III, IV, V, VI, or VII), wherein the amount of analog in the unit dosage from is in the range of about 1 mg to about 500 mg, and (ii) a pharmaceutically acceptable carrier. In some embodiments, the amount of analog in the unit dosage form includes about 10 mg to about 100 mg.

Kits

Also provided are kits containing materials useful for the treatment of a condition described herein (e.g., an infection). The kits may contain an analog described herein (e.g., any compound of formula I, II, III, IV, V, VI, or VII) and optionally contain instructions for use (e.g., instructions for preparation and/or administration of a formulation comprising an analog). Information detailing possible side effects of the formulation, and any other relevant information may also be enclosed. The instructions may be in any suitable format, including, but not limited to, printed matter, videotape, computer readable disk, optical disc or directions to internet-based instructions.

In one aspect, is provided a kit for treating an individual who suffers from or is susceptible to a condition described herein, comprising a first container comprising a dosage amount of a formulation as disclosed herein, and instructions for use. The container may be any of those known in the art and appropriate for storage and delivery of the formulation. In certain embodiments the kit further comprises a second container comprising a pharmaceutically acceptable carrier, diluent, adjuvant, etc. for preparation of the formulation to be administered to the individual.

In some embodiments, the kits comprise a container with a label. Suitable containers include, for example, bottles, vials, and test tubes. The containers may be formed from a variety of materials such as glass or plastic. The containers may hold an analog described herein or a formulation of an analog (e.g., a formulation comprising an analog and further comprising one or more additional pharmaceutical agents). The label on the container may indicate that the analog or the formulation is used for treating or suppressing a condition described herein (e.g., an infection), and may also indicate directions for either in vivo or in vitro use, such as those described herein.

The kit may further include other materials desirable from a commercial and user standpoint, including other buffers, diluents, filters, needles, syringes, and/or package inserts with instructions for performing any methods described herein. In some embodiments, the kit comprises the container described above and a second container comprising a buffer.

The kits may include additional pharmaceutical agents for use in conjunction with the formulation described herein. In some variations, the additional pharmaceutical agent(s) may be one or more antibacterial agents. These agents may be provided in a separate form, or mixed with the analogs described herein, provided such mixing does not reduce the effectiveness of either the pharmaceutical agent or formulation described herein and is compatible with the route of administration. Similarly the kits may include additional agents for adjunctive therapy or other agents known to the skilled artisan as effective in the treatment or prevention of the conditions described herein.

Kits may also be provided that contain sufficient dosages of the compounds described herein (including formulations thereof) to provide effective treatment for an individual for an extended period, such as 1-3 days, 1-5 days, a week, 2 weeks, 3, weeks, 4 weeks, 6 weeks, 8 weeks, 3 months, 4 months, 5 months, 6 months, 7 months, 8 months, 9 months or more.

The kits may include the formulation as described herein packaged in either a single unit dosage form or in a multi-use form. The kits may also include multiple units of the unit dose form. The kits may be used for any of the methods described herein, including, for example, to treat an individual with an infection. In certain embodiments, the kits may include a dosage amount of at least one formulation as disclosed herein. Kits may also comprise a means for the delivery of the formulation thereof.

Methods of Use

The analogs described herein (e.g., any compound of formula I, II, III, IV, V, VI, or VII) may be capable of treating one or more conditions responsive the analogs (e.g., an infection). In some embodiments are provided methods of treating an infection in an individual, comprising administering to the individual an effective amount of an analog described herein (e.g., any compound of formula I, II, III, IV, V, VI, or VII). Infections may include, for example, one or more of bacterial, sporal, fungal, and viral. In some embodiments, the infection does not include viral.

Examples of bacteria and bacterial infections that may be responsive to the analogs and/or applicable with the methods described herein include, but are not limited to, *Escherichia coli, Pseudomonas aeruginosa, Staphylococcus aureus, Staphylococcus aureus* (MSRA), *Serratia marcescens, Helicobacter pylori, Saccharomyces cerevisiae, Streptococcus thermophilus, Lactococcus lactis, Streptococcus agalactiae, Beta Hemolytic streptococcus, Mycobacterium bovis, Listeria monocytogenes, Peptostreptococcus micros, Fusobacterium nucleatum, Porphyromonas gingivalis, Salmonella typhimurium,* and/or *Bacciluss subtillus*, which may infect, for example, wounds, skin, eyes, ears, nose, and/or the GI tract. Examples of spores and sporal infections that may be applicable with methods described herein include, but are not limited to, Clostridium, Bacilli and anthrax. Examples of fungus and fungal infections that may be applicable with methods described herein include, but are not limited to, skin, wound and nail pathogens (e.g., Onycomycosis). Examples of viruses and viral infections that may be applicable with methods described herein include, but are not limited to, RNA and DNA viruses, such as Picornoviruses, HSV-1, HSV-2, and HIV. Also contemplated are *Candida albicans* (yeast) and *Aspergillus niger* (mold).

In some variations, the individual being treated for a condition described herein (e.g., an infection) has been identified as having one or more of the symptoms described herein. Identification of the conditions as described herein by a skilled physician is routine in the art such as routine physical exams or clinical detection (e.g., culture enrichment, gene amplification, and/or ELISA detection via microscopy, and other imaging techniques, such as X-rays, CAT scans, PET scans and NMR) and may also be suspected by the individual or others, for example, due to fever, chronic wounds, gangrene, abscess development, ulceration, swelling, diarrhea, dehydration, lethargy, vomiting, inflammation, pain, rash development, etc. In some embodiments, the individual has been identified as susceptible to one or more of the conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle or habits.

In some embodiments, the analogs (e.g., any compound of formula I, II, III, IV, V, VI, or VII) and/or formulations used herein are capable of reducing the severity of one or more symptoms associated with the condition (e.g., an infection) by at least about any of about 10%, 20%, 30%, 40%, 50%, 60%, 70%, 80%, 90%, 95%, or 100% compared to the corresponding symptom in the same individual prior to treatment or compared to the corresponding symptom in other individuals not receiving the methods and/or formulations. In some embodiments are provided methods of reducing the severity of one or more symptoms associated with the condition (e.g., an infection) by at least about any of about 10%, 20%, 30%, 40%, 50%, 60%, 70%, 80%, 90%, 95%, or 100% compared to the corresponding symptom in the same individual prior to treatment or compared to the corresponding symptom in other individuals not receiving the methods and/or formulations, comprising administering to the individual an effective amount of an analog described herein (e.g., any compound of formula I, II, III, IV, V, VI, or VII).

In some embodiment, the analogs described herein (e.g., any compound of formula I, II, III, IV, V, VI, or VII) are capable of inhibiting the growth of a microorganism (e.g., bacteria, spore, fungus, or virus). In some embodiments are provided methods of inhibiting the growth of a microorganism, comprising contacting the microorganism with an effective amount of a compound of an analog described herein (e.g., any compound of formula I, II, III, IV, V, VI, or VII). In some embodiments, the analogs described herein (e.g., any compound of formula I, II, III, IV, V, VI, or VII) may be used as bactericidal, antibacterial, anti-infective, antimicrobial, sporicidal, disinfectant, antifungal and/or antiviral agents.

In some embodiments, the analogs described herein (e.g., any compound of formula I, II, III, IV, V, VI, or VII) are capable of inhibiting protein synthesis (e.g., in a microorganism). In some embodiments, the analogs are capable of inhibiting protein synthesis by at least about any of about 10%, 20%, 30%, 40%, 50%, 60%, 70%, 80%, 90%, 95%, or 100% compared to not receiving the analog. In some embodiments are provided methods of inhibiting protein synthesis in a microorganism (e.g., bacteria, spore, fungus, or virus), comprising contacting the microorganism with an effective amount of an analog described herein (e.g., any compound of formula I, II, III, IV, V, VI, or VII). In some of these embodiments, protein synthesis is inhibited by at least about any of about 10%, 20%, 30%, 40%, 50%, 60%, 70%, 80%, 90%, 95%, or 100% compared to not receiving the analog.

In some embodiments, the analogs are capable of selectively inhibiting microbial protein synthesis (e.g., bacterial) over eukaryotic protein synthesis (e.g., by greater than about 10%, 20%, 30%, 40%, 50%, 60%, 70%, 80%, 90%, 95%, or 98% selective over eukaryotic protein synthesis). In some embodiments are provided methods of selectively inhibiting microbial protein synthesis (e.g., bacteria), over eukaryotic protein synthesis (e.g., by greater than about 10%, 20%, 30%, 40%, 50%, 60%, 70%, 80%, 90%, 95%, or 98% selective over eukaryotic protein synthesis) comprising contacting the microorganism with an effective amount of an analog described herein (e.g., any compound of formula I, II, III, IV, V, VI, or VII).

The analogs described herein may exhibit potential inhibitory properties of tRNA synthetases (e.g., bacterial aminoacyl-tRNA synthetases, such as methionyl-tRNA synthetase). In some embodiments, the analogs described herein (e.g., any compound of formula I, II, III, IV, V, VI, or VII) are capable of inhibiting a bacterial aminoacyl-tRNA synthetase (e.g., methionyl-tRNA synthetase). In some embodiments, the analogs are capable of inhibiting bacterial aminoacyl-tRNA synthetase (e.g., methionyl-tRNA synthetase) by at least about any of about 10%, 20%, 30%, 40%, 50%, 60%, 70%, 80%, 90%, 95%, or 100% compared to not receiving the analog. In some embodiments are provided methods of inhibiting bacterial aminoacyl-tRNA synthetase (e.g., methionyl-tRNA synthetase), comprising contacting the enzyme with an effective amount of an analog described herein (e.g., any compound of formula I, II, III, IV, V, VI, or VII). In some of these embodiments, bacterial aminoacyl-tRNA synthetase (e.g., methionyl-tRNA synthetase) is inhibited by at least about any of about 10%, 20%, 30%, 40%, 50%, 60%, 70%, 80%, 90%, 95%, or 100% compared to not receiving the analog. In some of these embodiments, bacterial aminoacyl-tRNA synthetase (e.g., methionyl-tRNA synthetase) is inhibited with an analog described herein (e.g., any compound of formula I, II, III, IV, V, VI, or VII) having a K, of less than about 10 mM, or 5 mM, 2.5 mM, 1 mM, 750 μM, 500 μM, 250 μM, 100 μM, 75 μM, 50 μM, 10 μM, 5 μM, 2 μM, 1 μM, 750 nM, 500 nM, 250 nM, 100 nM, 75 nM, 50 nM, 25 nM, 10 nM, 5 nM, 2.5 nM, or 1 nM. Methods used to measure inhibitory effects toward bacterial aminoacyl-tRNA synthetases can be found in the Examples section below and, for example, Vaughan M. D., et al. Investigation of Bioisosteric effects on the integration of substrates/inhibitors with the methionyl-tRNA synthetase from *Escherichia coli*. Medicinal Chemistry, 2005, 1:227-237, the content of which is hereby incorporated by reference in its entirety.

The analogs described herein (e.g., any compound of formula I, II, III, IV, V, VI, or VII) may exhibit antioxidant properties. In some embodiments, the analogs are capable of reducing free-radical formation (e.g., NADPH-mediated radical formation). In some embodiments, the analogs are capable of reducing free-radical formation (e.g., NADPH-mediated radical formation) by greater than about 5%, 10%, 15%, 20%, 25%, 30%, 35%, 40%, 45%, 50%, 55%, 60%, 65%, 75%, 85%, or 95% (e.g., as measured by the formation of reactive oxygen species (ROS) such as described in Erdmann K., et al. L-Methionine Reduces Oxidant Stress in Endothelial Cells: Role of Heme Oxygenase-1, Ferritin, and Nitric Oxide. *The AAPS Journal*, 2005, 7:E195-E200, the content of which is hereby incorporated by reference). In some embodiments are provided methods of reducing free-radical formation (e.g., NADPH-mediated radical formation) in an individual, comprising administering to the individual an effective amount of an analog described herein (e.g., any compound of formula I, II, III, IV, V, VI, or VII). In some of these embodiments, the reduction in free-radical formation is greater than about 5%, 10%, 15%, 20%, 25%, 30%, 35%, 40%, 45%, 50%, 55%, 60%, 65%, 75%, 85%, or 95% compared to not administering the analog. In some embodiments, the analogs described herein (e.g., any compound of formula I, II, III, IV, V, VI, or VII) are capable of reducing oxidant levels (e.g., hydrogen peroxide levels, as described in Levine R., et al. Methionine residues as endogenous antioxidants in proteins. *PNAS.*, 1996, 93:15036-15040, the content of which is hereby incorporated by reference). In some embodiments are provided methods of reducing oxidant levels, comprising contacting the oxidant with an effective amount of an analog described herein (e.g., any compound of formula I, II, III, IV, V, VI, or VII). In some of these embodiments, the oxidant level is reduced by greater than about 5%, 10%, 15%, 20%, 25%, 30%, 35%, 40%, 45%, 50%, 55%, 60%, 65%, 75%, 85%, or 95%.

The analogs described herein (e.g., any compound of formula I, II, III, IV, V, VI, or VII) and formulations comprising the analogs described herein, may be useful in any application in which antimicrobial properties are desirable. Such applications and methods include, without limitation, use of the analogs (e.g., in an effective amount) for the treatment of wounds, burns, and canker sores; irrigation and/or cleaning of tissue sites (e.g., pre- and post-operative); ophthalmic applications (e.g., in contact lens cleaning solutions or for irrigation of the eye before, during, or post ophthalmic surgery); for dermatological applications, psoriasis; and numerous applications which are readily apparent to one skilled in the art. Applications and methods also include the use of the analogs described herein (e.g., in an effective amount) for the elimination or reduction of pathogens on surfaces including medical equipment, instruments, devices or food (without limiting to meat, fruits, vegetables) and food contact surfaces including the elimination or reduction of bacterial biofilms. The analogs described herein may also be useful as an irrigation solution, for example, during dental, endodontics filling, periodontal, month wash, toothpaste, impregnated night-gard and ophthalmic procedures, as well as for pre- and post-operative cleaning of tissue sites, and as a gargling solution for treatment of canker sores.

In one aspect, is provided a method for the treatment of various medical conditions such as promoting wound healing, reduction of pathogens in open wounds, wound decontamination, ocular disinfection or decontamination, oral disinfection, antifungal therapy, ophthalmic applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis and related diseases, treatment of viral infections, treatment of skin diseases, tissue repair and regeneration, which comprises using an analog described herein (e.g., any compound of formula I, II, III, IV, V, VI, or VII), for example, by applying the solution to the site where treatment is required. Non-limiting examples of biofilm that may be treated using the solutions of the present invention include those cited in the review article entitled "Is there a role for quorum signals in bacterial biofilms?" by S. Kjelleberg, and S. Molin, PMID: 12057677 (PubMed-indexed for MEDLINE), which is hereby incorporated by reference in its entirety.

The analogs described herein (e.g., any compound of formula I, II, III, IV, V, VI, or VII) and formulations thereof may be effective in reducing bacterial load, thus improving wound healing. The analogs could be well tolerated, improve the granulation of wound tissue, and/or reduce the need for debridement. In one aspect, is provided a method for the treatment of a wound in an individual comprising administering an effective amount of an analog described herein (e.g., any compound of formula I, II, III, IV, V, VI, or VII) or a formulation thereof. The analogs described herein and formulations thereof may be used in the treatment of many different types of wounds, including, without limitation, diabetic ulcers, gangrene, venous ulcers, decubitus ulcers, pressure ulcers, wounds due to bites, acute trauma wounds, surgical wounds, burns, deep wounds (e.g., wounds which do not respond to usual medications and locally applied treatments), as an adjunct treatment with Vacuum Assisted Wound Closure (V.A.C) devices, and/or prevention or treatment of infection associated with gun-shot wounds (e.g., for military use).

The analogs described herein (e.g., any compound of formula I, II, III, IV, V, VI, or VII) and formulations thereof may be used in methods for wound care as follows: a gauze material or gauze pad is presoaked with sufficient solution containing the analog to saturate it and is then squeezed to remove excess solution. This removes species present in the gauze which would react with and reduce the effectiveness of the solution of the invention. The gauze is wetted after this procedure, but not soaked. Additional solution is then applied to completely wet the gauze, which is then immediately applied to the wound. In the alternative, the gauze may be applied to the wound and then additional solution is applied. Typically the wound site is packed with the solution-soaked gauze, and optionally, a Vaseline gauze can be applied on top of the packed wound to keep it moist and free of contaminating germs. The wound site is then wrapped with wound dressings as is standard in the art. The analog may also be used to clean a wound by pouring a solution comprising the analog directly on the wound site to remove any necrotic tissue by a mechanical procedure, and also as a cleanser or irrigant.

The analogs described herein (e.g., any compound of formula I, II, III, IV, V, VI, or VII) and formulations thereof may be used to treat canker sores (mouth ulcers) or cold sores by rinsing the affected area. In one aspect, is provided a method for the treatment of a canker sore in an individual comprising administering an effective amount of an analog described herein (e.g., any compound of formula I, II, III, IV, V, VI, or VII) or a formulation thereof. For example, a solution comprising the analog can be used by soaking the cold sore 3-4 times a day, each time with 2-3 applications, and putting the solution in contact with the sore for 20-30 seconds. The analog may also be used with a mouth rinse for dental and mouth hygiene and to control infection. In this instance, the analog may be used in a solution form as a gargling solution to fight throat infection. The solution the analog may be applied with the help of a cotton swab for more specific areas. The solution can be used once or several times a day according to a patient's needs and condition.

The analogs described herein (e.g., any compound of formula I, II, III, IV, V, VI, or VII) and formulations thereof may be used in place of a saline solution to remove a foreign body from, to rinse, and/or to irrigate the eyes. In some of these embodiments, the analog is in the form of a physiologically-balanced solution. The analog may also be applied topically before or after surgery to disinfect an eye and surrounding tissues. The analog (e.g., in solution form) can be used once or several times a day according to a patient's needs and condition. The solution can be applied by dropping it directly into the eyes as necessary.

The analogs described herein (e.g., any compound of formula I, II, III, IV, V, VI, or VII) and formulations thereof (e.g., a physiologically-balanced solution comprising the analog) may be used for the treatment of ocular infection or contamination. In one aspect, is provided a method for the treatment of ocular infection or contamination in an individual comprising administering an effective amount of an analogs described herein (e.g., any compound of formula I, II, III, IV, V, VI, or VII) or a formulation thereof. The analogs may be used as a replacement for silver nitrate in the disinfection of the eyes of neonates.

The analogs described herein (e.g., any compound of formula I, II, III, IV, V, VI, or VII) and formulations thereof may be used for the cleaning eyes in adults and in pediatrics. For example, various viral infections, bacterial or fungal infections, or pathogenic agents may be effectively treated with the solution of the present invention. Non-limiting examples of pathogenic agents that could be successfully treated with the solution of the present invention include *chlamydia trachomatis*, gonorrhea as well as other bacterial, fungal, and viral infections.

The analogs described herein (e.g., any compound of formula I, II, III, IV, V, VI, or VII) and formulations thereof may be used as a means of ensuring that microbes cannot survive in solutions intended for use in injection, infusion or for use in the eye by incorporation of an appropriate amount of such compound into the solution at the time of manufacture.

The analogs described herein (e.g., any compound of formula I, II, III, IV, V, VI, or VII) and formulations thereof may also be used to treat skin that is infected. In one aspect, is provided a method for the treatment of infected skin in an individual comprising administering an effective amount of an analog described herein (e.g., any compound of formula I, II, III, IV, V, VI, or VII) or a formulation thereof. In a skin of a patient showing medical signs of infection, the analog may be applied directly to the area of the skin that is infected. After at least one application of the solution onto the infected skin using standard methods of application known in the art, the disinfective properties of the solution may be noted.

The analogs described herein (e.g., any compound of formula I, II, III, IV, V, VI, or VII) may be used to treat topical infections by incorporating them into creams, ointments or lotions for use in such conditions (e.g., as used with an impregnated toweled or bandage). Such creams, ointments, lotions, or gels might be used a broad variety of skin conditions and may incorporate penetration enhancers in order to deliver the antimicrobial activity of the analog to microbes present beneath the outer (epidermis) layers of the skin.

The analogs described herein (e.g., any compound of formula I, II, III, IV, V, VI, or VII) and formulations thereof may be used for the reduction of pathogens in pulmonary infections. For example, various viral or bacterial and fungal infections may be effectively treated with the solution of the present invention. In one aspect, is provided a method for the treatment of a pulmonary infection in an individual comprising administering an effective amount of an analog described herein (e.g., any compound of formula I, II, III, IV, V, VI, or VII) or a formulation thereof. Non-limited examples of infections that may be effectively treated using the solution of the present invention include anthrax spores present in the lungs, and the reduction of pneumonia causing bacteria in the lungs, including strep bacteria and the like (e.g., conditions associated with Cystic fibrosis).

The analogs described herein (e.g., any compound of formula I, II, III, IV, V, VI, or VII) and formulations thereof may be used for the treatment of gynecological infections, such as urinary tract infections and the like. In one aspect, is provided a method for the treatment of a gynecological infection in an individual comprising administering an effective amount of an analog described herein (e.g., any compound of formula I, II, III, IV, V, VI, or VII) or a formulation thereof. For example, various microorganisms, yeasts (e.g., Monilia, *Candida albicans*, etc), bacterial infections, HSV-2, HIV or other pathogenic agents may be effectively treated with the solution of the present invention. Optionally, the application of the analogs can be used with other medications for the treatment of gynecological infections. For example, use as a lavage of birth canal in pregnant female patients with suspected venereal diseases, and potentially as a bathing and cleansing solution on babies right after birth in the deliver rooms of hospitals or as disinfectant on catheters and shunt in dialysis room.

Isotonic solutions comprising one or more analogs described herein (e.g., any compound of formula I, II, III, IV, V, VI, or VII) may be used as an irritant during surgery in order to prevent the development of surgical site infections, that frequently lead to prolonged hospitalizations and, occasionally, in death. In one aspect, is provided a method for preventing the development of surgical site infections comprising contacting the surgical site with an effective amount of an analog described herein (e.g., any compound of formula I, II, III, IV, V, VI, or VII) or a formulation thereof. The use of a solution comprising an analog described herein in place of saline could substantially reduce the risks of such infections especially in the case of gastric surgery and of prolonged operations, where the rate of infections may be as high as 10%.

The analogs described herein (e.g., any compound of formula I, II, III, IV, V, VI, or VII) and formulations thereof may be used as a means of safely and rapidly disinfecting the hands of surgeons and nurses to reduce the risk of transporting infectious agents into an operating theatre. Additionally, solution of the present invention may be used to reduce or eliminate the infectious agent from the skin of patients (pre and post operative) in the area of a surgical incision.

The analogs described herein (e.g., any compound of formula I, II, III, IV, V, VI, or VII) and formulations thereof may be used for the reduction of pathogens on the surfaces of medical devices (e.g., as a lock solution or gel) and/or surgical implements to prevent infection to the patient on whom the devices and/or implements are used, or in whom they are implanted. In one aspect, is provided a method for the reduction of pathogens on the surfaces of a medical device or surgical implement comprising contacting the device or implement with an effective amount of an analog described herein (e.g., any compound of formula I, II, III, IV, V, VI, or VII) or a formulation thereof. The analogs may also be used for the reduction and/or elimination of infections that occur at the entry ports of catheters and shunts that are particularly prone to such infections.

The analogs described herein (e.g., any compound of formula I, II, III, IV, V, VI, or VII) and formulations thereof may be applied directly or through delivery from a device that creates a mist (aerosolization) to the surfaces of a room, vehicle interior or other such largely confined space in order to reduce or eliminate infectious pathogens that may be suspected to be present. In one aspect, is provided a method reduce or eliminate infectious pathogens on a surface comprising contacting the surface with an effective amount of an analog described herein (e.g., any compound of formula I, II, III, IV, V, VI, or VII) or a formulation thereof. In such an application, it could be used to decontaminate operating theaters where infectious pathogens have been detected or rooms, vehicles and other surfaces where biological warfare agents have been dispersed.

The analogs described herein (e.g., any compound of formula I, II, III, IV, V, VI, or VII) and formulations thereof may be used for reducing pathogens on food (including, without limitation, meats, fruits and vegetables). In one aspect, is provided for reducing pathogens on food comprising contacting the food with an effective amount of an analog described herein (e.g., any compound of formula I, II, III, IV, V, VI, or VII) or a formulation thereof. In some embodiments, the analog is applied as a wash or mist to the food. In some embodiments, the food is dipped in a solution comprising the analog. The analogs may also be applied to surfaces and implements used in the preparation of foods to prevent the transfer of pathogens from such surfaces and implements to the food.

Combination Therapy

The analogs described herein (e.g., any compound of formula I, II, III, IV, V, VI, or VII) may be formulated and/or administered in conjunction with one or more additional pharmaceutical agents, as described herein and as known in the art, including one or more additional pharmaceutical agents to further reduce the occurrence and/or severity of symptoms and/or clinical manifestations thereof, as well as additional pharmaceutical agents that treat or prevent the underlying conditions, and/or in conjunction with (e.g., prior to, concurrently with, or after) additional treatment modalities. As used herein, the term "additional treatment modality" refers to treatment/prevention of the conditions described herein without the use of a pharmaceutical agent (e.g., surgery, abscess incision & drainage, etc.). Where combinations of pharmaceutical agent(s) and/or additional treatment modality(ies) are used, they may be, independently, administered prior to, concurrently with, or after administration of one or more of the analogs (or formulation(s) thereof) as described herein.

The additional pharmaceutical agents (e.g., antibacterial agents) administered with one or more of the analogs described herein (e.g., any analog of formula I, II, or III) can be administered at the recommended maximum clinical dosage or at lower doses, such as those indicated in the PHYSICIANS' DESK REFERENCE (PDR) 53rd Edition (1999), or at such therapeutically useful amounts as would be known to one of ordinary skill in the art. Dosage levels of the additional pharmaceutical agents in the formulations may be varied so as to obtain a desired therapeutic response depending on the route of administration, severity of the disease and the characteristics and response of the patient. When administered as a combination, the analogs described herein can be formulated as separate formulations, which are given at the same time or different times, or the analogs can be given with the additional pharmaceutical agent as a single formulation.

The optimal combination of one or more additional pharmaceutical agents and/or one or more additional treatment modalities in conjunction with administration of the analogs described herein can be determined by an attending physician or veterinarian based on the individual and taking into consideration the various factors affecting the particular individual, including those described herein.

Dosing and Methods of Administration

The amount of the analog administered to an individual (such as a human) may vary with the particular formulation, the method of administration, and the particular type of condition being treated, and should be sufficient to produce a desirable beneficial effect. The amount administered in order to achieve an effective amount will depend upon a variety of factors, including, for example, the particular condition being treated, the frequency of administration, the particular formulation being administered, the severity of the condition being treated and the age, weight and general health of the individual, the adverse effects experienced by the individual being treated, etc. A pharmaceutical unit dosage chosen may be fabricated and administered to provide a defined final concentration of drug in the blood, tissues, organs, or other targeted region of the body. Determination of an effective amount for a given situation can be readily determined by routine experimentation (e.g., using in vivo animal models) and is within the skill and judgment of the ordinary clinician, particularly in view of the teachings provided herein.

In some embodiments, the amount of the analog is effective to result in an objective response (such as a partial response or a complete response). In some embodiments, the amount of the analog is sufficient to result in a complete response in the individual. In some embodiments, the amount of the analog is sufficient to result in a partial response in the individual. In some embodiments, the amount of the analog administered alone is sufficient to produce an overall response rate (e.g., by decreasing the size reduce the number of microbial cells, inhibiting microbial cell growth and/or killing existing microbial cells, reducing morbidity and/or mortality, and/or relieving to some extent one or more of the symptoms associated with the an infection, such as levels of redness, pain, fever, and inflammation) by more than any of about 10%, 20%, 30%, 40%, 50%, 60%, 70%, 80%, 90%, or 95% among a population of individuals treated with the analog. A complete response can be defined as a return to a normal range value of at least 1, 2, 5, 10, 15, 20, 28, 60, or 90 days from the pretreatment value.

In some embodiments, the amount of the analog is below the level that induces a toxicological effect (i.e., an effect above a clinically acceptable level of toxicity) or is at a level where a potential side effect can be controlled or tolerated when the analog is administered to the individual. In some embodiments, the amount of the analog is close to a maximum tolerated dose (MTD) of the analog following the same dosing regime. In some embodiments, the amount of the analog is more than about any of 80%, 90%, 95%, or 98% of the MTD.

In some embodiments, the amount of analog (e.g., an analog in a formulation) is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of analog in the effective amount of the formulation (e.g., a unit dosage form) is in the range of about 5 mg to about 500 mg, such as about 30 mg to about 300 mg or about 50 mg to about 200 mg.

In some embodiments, the concentration of the analog in the formulation is dilute (about 0.1 mg/mL) or concentrated (about 100 mg/mL), including for example any of about 0.1 to about 50 mg/mL, about 0.1 to about 20 mg/mL, about 1 to about 10 mg/mL, about 2 mg/mL to about 8 mg/mL, about 4 to about 6 mg/mL, about 5 mg/mL. In some embodiments, the concentration of the analog is at least about any of 0.5 mg/mL, 1.3 mg/mL, 1.5 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 40 mg/mL, or 50 mg/mL. In some embodiments, the concentration of the analog in the formulation is about 0.1% to 95%, or 0.1% to 80%, or 0.5% to 70%, or 0.5% to 60%, or 0.5% to 60%, or 0.5% to 50%, or 0.5% to 40%, or 0.5% to 30%, or 0.5% to 25%, or 0.5% to 20%, or 0.5% to 15%, or 0.5% to 10%, or 0.5% to 5%, or 0.1% to 2%, 0.1% to 1%, 0.1% to 0.5%.

Examples of the analog (e.g., any compound of formula I, II, III, IV, V, VI, or VII, alone or in combination with an additional pharmaceutical agent) which can be used are an effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight.

Exemplary dosing frequencies include, but are not limited to, weekly without break; weekly, three out of four weeks; once every three weeks; once every two weeks; weekly, two out of three weeks. In some embodiments, the analog (or formulation thereof) is administered about once every 2 weeks, once every 3 weeks, once every 4 weeks, once every 6 weeks, or once every 8 weeks. In some embodiments, the analog is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 12 days, 10 days, 9 days, 8 days, 7 days, 6 days, 5 days, 4 days, 3 days, 2 days, or 1 day. The administration of the analogs described herein can be extended over an extended period of time, such as from about a month up to about seven years. In some embodiments, the analog is administered over a period of at least about any of 2, 3, 4, 5, 6, 7, 8, 9, 10, 11, 12, 18, 24, 30, 36, 48, 60, 72, or 84 months. In some embodiments, there is no break in the dosing schedule. In some embodiments, the interval between each administration is no more than about a week.

The analogs described herein allow, in some embodiments, infusion of the analog to an individual over an infusion time that is shorter than about 24 hours. For example, in some embodiments, the analog is administered over an infusion period of less than about any of 24 hours, 12 hours, 8 hours, 5 hours, 3 hours, 2 hours, 1 hour, 30 minutes, 20 minutes, or minutes. In some embodiments, the analog is administered over an infusion period of about 30 minutes.

Any of the analogs described herein (e.g., any compound of formula I, II, III, IV, V, VI, or VII) may be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, the analog is administered by sustained continuous release. In one variation, the analogs can be administered by any acceptable route including, but not limited to, orally, intramuscularly, transdermally, intravenously, through an inhaler or other air borne delivery systems and the like. Additional methods of administration are known in the art.

In some embodiments, the analogs described herein (e.g., any compound of formula I, II, III, IV, V, VI, or VII) are administered parenterally (e.g., intravenously). In some embodiments are provided methods of treating a condition (e.g., an infection) comprising parenterally (e.g., intravenously) administering an analog described herein. Injectable preparations (for example, sterile injectable aqueous or oleaginous suspensions) may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. The sterile injectable preparation may also be a sterile powder to be reconstituted using acceptable vehicles prior to administration. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables.

In some embodiments, the analogs described herein (or formulations thereof) are suitable for oral administration. The analogs described for oral use herein can be administered in solid form, in liquid form, in aerosol form, and/or in the form of tablets, pills, powder mixtures, capsules, granules, etc.

Solid dosage forms for oral administration may include capsules, tablets, pills, powders, and granules. In such solid dosage forms, the analog may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such formulations may also comprise adjuvants, such as wetting agents, emulsifying and suspending agents, cyclodextrins, and sweetening, flavoring, and perfuming agents.

As described herein, the analogs may be administered with an additional therapeutic agent and/or an additional treatment modality. The dosing frequency of the analog and the additional therapeutic agent may be adjusted over the course of the treatment based on the judgment of the administering physician. In some embodiments, the analog and the additional therapeutic agent are administered simultaneously, sequentially, or concurrently. When administered separately, the analog and the additional therapeutic agent can be administered at different dosing frequency or intervals. For example, the analog can be administered weekly, while the additional therapeutic agent can be administered more or less frequently. In some embodiments, sustained continuous release formulation of the analog and/or the additional therapeutic agent may be used. Various formulations and devices for achieving sustained release are known in the art. A combination of the administration configurations described herein can be used.

The present invention will be understood more readily by reference to the following examples, which are provided by way of illustration and are not intended to be limiting of the present invention.

EXAMPLES

Example 1

Synthesis of (S)-2-amino-4-(methylthio)butane-1-sulfonic acid hydrochloride (HCl salt, S-enantiomer of I-A)

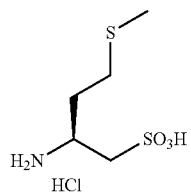

To a solution of (S)-tert-butyl 1-hydroxy-4-(methylthio)butan-2-ylcarbamate (1.0 g, 1.0 eq, Chem-Impex, Catalog #03206) in DCM at −25° C. was added triethylamine (2.5 eq), followed by methanesulfonyl chloride (2.0 eq). The mixture was stirred at −25° C. for 1 h and RT for 30 min, washed with 1 N HCl, sat. NaHCO$_3$ and brine, dried and concentrated to give a residue, which was purified by flash chromatography column on silica gel using ethyl acetate and hexane (1:2) as eluent to give (S)-2-(tert-butoxycarbonylamino)-4-(methylthio)butyl methanesulfonate (1.1 g, 75%). 1H NMR (CDCl$_3$, 300 MHz) d 4.25 (m, 2H, OCH$_2$), 4.0 (br s, 1H, BocNHCH), 3.05 (s, 3H, SO$_2$CH$_3$), 2.55 (m, 2H, SCH$_2$), 2.15 (s, 3H, SCH$_3$), 1.85 (m, 2H, BocNHCHCH$_2$CH2S), 1.45 (s, 9H, OC(CH$_3$)$_3$).

(S)-2-(tert-butoxycarbonylamino)-4-(methylthio)butyl methanesulfonate (1.1 g, 3.51 mmol, 1.0 eq) was dissolved in EtOH (10 mL) and water (8.0 mL). Sodium sulfite (2.21 g, 5.0 eq) was added. The mixture was heated to reflux for 16 hours, and concentrated. The residue was purified by reversed phase column (Diaion HP-20) using distilled water (200 ml) first, then 10% CH$_3$CN in water and finally 20% CH$_3$CN in water to give sodium (S)-2-(tert-butoxycarbonylamino)-4-(methylthio)butane-1-sulfonate (376 mg, 37%). 1H NMR (DMSO-d6, 300 MHz) d 6.75 (d, 1H, NH), 3.50 (br s, 1H, BocNHCH), 2.3-2.5 (m, 4H, SCH$_2$ and OSCH$_2$, overlapped with DMSO solvent peak), 2.0 (s, 3H, SCH$_3$), 1.8 (m, 1H, NHCHCH$_2$CH2S), 1.6 (m, 1H, NHCHCH$_2$CH2S), 1.35 (s, 9H, OC(CH$_3$)$_3$). LC-MS: 2.03 min; MS (ESI-) m/z 298 (M-Na)$^+$, 198 (M-Na-Boc)$^+$.

Sodium (S)-2-(tert-butoxycarbonylamino)-4-(methylthio)butane-1-sulfonate (350 mg) was treated with 6 N HCl in water at 40° C. for 1 h. The reaction mixture was purified on Diaion HP-20 column eluting with water (200 mL), then 20% CH$_3$CN in water. The fractions were concentrated and dried under vacuum to give (S)-2-amino-4-(methylthio)butane-1-sulfonic acid hydrochloride as a light yellow solid (53 mg, 21%). 1H NMR (DMSO-d6, 300 MHz) d 8.05 (br s, 3H, NH$_3$), 3.4 (br s, 1H, NCH), 2.65 (m, 4H, SCH$_2$ and OSCH$_2$), 2.1 (s, 3H, SCH$_3$), 1.8-2.1 (m, 2H, NCHCH$_2$CH$_2$SCH$_3$). LC-MS: 0.15 min (eluted along with solvent peak); MS (ESI-) m/z 198 (M-1)$^+$. Purity: >95% by 1H NMR and LC-MS. The chirality of the final product was based on the commercially available starting material, (S)-tert-butyl 1-hydroxy-4-(methylthio)butan-2-ylcarbamate, which has a natural configuration (L−). The reactions did not change the chiral center.

LC conditions: Mobile phase A: 10 mM ammonium acetate in water (pH 5.0); Mobile phase B: acetonitrile; Column: Eclipse-XDB-C18 (2.1×50 mm) at 40° C.; Gradient (1 mL/min); conditions (min, A %, B %): 0:00, 97, 3; 0.25, 97, 3; 3:00, 5, 95; 4:50, 5, 95; 4:60, 97, 3.

Example 2

Synthesis of (S)-2-(2-aminoacetamido)-4-(methylthio)butane-1-sulfonic acid hydrochloride (HCl salt, S-enantiomer of I-Z)

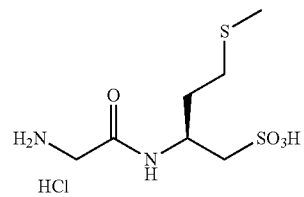

(S)-2-(2-aminoacetamido)-4-(methylthio)butane-1-sulfonic acid hydrochloride was synthesized by coupling a 2,5-dioxopyrrolidin-1-yl 2-(tert-butoxycarbonylamino)acetate to sodium (S)-2-amino-4-(methylthio)butane-1-sulfonate in the presence of mild base. The resulting (S)-2-(2-(tert-butoxycarbonylamino)acetamido)-4-(methylthio)butane-1-sulfonic acid was deprotected in the presence of 6M HCl$_{(aq.)}$ to provide the desired product. (M+H)$^+$=256.9.

Example 3

Synthesis of (S)-2-amino-N-hydroxy-4-(methylthio)butanamide hydrochloride (HCl salt, S-enantiomer of I-AA)

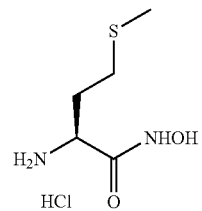

To a solution of (S)-methyl 2-amino-4-(methylthio)butanoate (5 g, 30.7 mmol) in dioxane (50 mL) and water (20 mL) at room temperature was added sodium carbonate (5.3 g, 50 mmol) and boc anhydride (7.96 g, 36.8 mmol). The mixture was stirred overnight at room temperature followed by dioxane removal under vacuum. The aqueous layer was extracted with ethyl acetate (3×). The combined organic layers were washed with 1N HCl, brine, and dried over sodium sulfate, filtered and concentrated to give a residue, which was purified on silica gel column to give (S)-methyl 2-(tert-butoxycarbonylamino)-4-(methylthio)butanoate (5.1 g, 63%). MS calcd for $(C_{11}H_{21}NO_4S+H)^+$: 264.1; MS found: $(M+H)^+$=264.1, 164.1 (-Boc).

A solution of (S)-methyl 2-(tert-butoxycarbonylamino)-4-(methylthio)butanoate (1 g, 3.8 mmol) in dioxane (10 mL) and hydroxylamine (50% in water, 10 mL) was stirred at room temperature for 2 days. The solution was diluted with ethyl acetate (200 mL). The organic layer was washed with 1N HCl, brine, and dried over sodium sulfate, filtered and concentrated to give a residue, which was purified on silica gel column (hexane:ethyl acetate, 1:1 to pure acetate) to give (S)-tert-butyl 1-(hydroxyamino)-4-(methylthio)-1-oxobutan-2-ylcarbamate as a white solid (0.33 g, 33%). MS calcd for $(C_{10}H_{20}N_2O_4S+H)^+$: 265.1; MS found: $(M+H)^+$=266.2, 166.2 (-Boc).

To solid (S)-tert-butyl 1-(hydroxyamino)-4-(methylthio)-1-oxobutan-2-ylcarbamate (0.33 g, 1.25 mmol) was added 4 N HCl in dioxane (2 mL, 8 mmol). The mixture was stirred at room temperature for one hour, and concentrated. The residue was triturated with ether, and dried to provide 1-Hydroxycarbamoyl-3-methylsulfanyl-propyl-amine hydrochloride (S)-2-amino-N-hydroxy-4-(methylthio)butanamide hydrochloride (0.18 g, 80%). MS calcd for $(C_5H_{12}N_2O_2S—H)^+$: 163.1; MS found: $(M-H)^+$=163.0

Example 4

Synthesis of (S)-2-(2-aminoacetamido)-N-hydroxy-4-(methylthio)butanamide hydrochloride (HCl salt, S-enantiomer of I-AB)

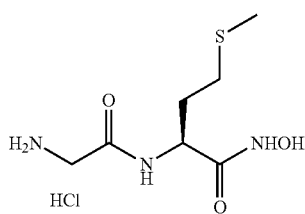

To a solution of (S)-methyl 2-amino-4-(methylthio)butanoate (5 g, 30.7 mmol) and Boc-glycine (6.4 g, 36.8 mmol) in dichloromethane (100 mL) at room temperature was added diisopropylcarbodiimide (4.6 g, 36.8 mmol) and diisopropylethylamine (4.75 g, 36.8 mmol). The mixture was stirred overnight at room temperature, washed with 1N HCl, brine, and dried over sodium sulfate, filtered and concentrated to give a residue, which was purified on silica gel column to give (S)-methyl 12,12-dimethyl-7,10-dioxo-11-oxa-2-thia-6,9-diazatridecane-5-carboxylate (7 g, 71%). MS calcd for $(C_{13}H_{24}N_2O_5S+H)^+$: 321.1; MS found: $(M+H)^+$=321.2.

A solution of (S)-methyl 12,12-dimethyl-7,10-dioxo-11-oxa-2-thia-6,9-diazatridecane-5-carboxylate (7 g, 21 mmol) in dioxane (120 mL) and hydroxylamine (50% in water, 80 mL) was stirred at room temperature for 4 hours. The solution was concentrated and extracted with ethyl acetate (200 mL). The organic layers were washed with 1N HCl, brine, and dried over sodium sulfate, filtered and concentrated to give a residue, which was purified on silica gel column (hexane: ethyl acetate, 1:1 to pure acetate) to give (S)-tert-butyl 2-(1-(hydroxyamino)-4-(methylthio)-1-oxobutan-2-ylamino)-2-oxoethylcarbamate (2 g, 28%). MS calcd for $(C_{12}H_{23}N_3O_5S+H)^+$: 322.1; MS found: $(M+H)^+$=322.0.

To (S)-tert-butyl 2-(1-(hydroxyamino)-4-(methylthio)-1-oxobutan-2-ylamino)-2-oxoethylcarbamate (200 mg, 0.62 mmol) was added 4N HCl in dioxane (1 mL). The mixture was stirred at rt for 1 h, concentrated and triturated with ether to give (S)-2-(2-aminoacetamido)-N-hydroxy-4-(methylthio)butanamide hydrochloride as a white solid after drying under vacuum (0.12 g, 75%). MS calcd for $(C_7H_{16}N_3O_3S—H)^+$: 220.1; MS found: $(M+H)^+$=220.0.

Example 5

Bactericidal Activity

*Escherichia coli* (ATCC 11229) is diluted in sterile saline to prepare inocula. Various test articles are transferred to individual tubes already containing $1.0 \times 10^5$ to $2.0 \times 10^5$ Colony Forming Units (CFU)/mL bacteria and mixed by gentle vortexing and then incubated at 37° C. for 1 or 24 hours. Bacterial plating in a Petri dish is performed immediately after the designated exposure time without the addition of a neutralizer, and independently with addition of neutralizer (as control). Thus, 0.1 mL is removed after 1 or 24 hours exposure times and plated. Plates are incubated at 37° C., and the numbers of bacteria are counted by direct colony count to numerate the surviving bacteria as CFU/mL. Positive growth controls are made with sterile 0.9% saline. All test articles were tested three times. The results are tabulated to show the comparison of antimicrobial effectiveness range of 1-24 hr.

Example 6

Bactericidal Activity for Methionine Analogs

Comparative Minimum Bactericidal Concentration (MBC) results provide estimates of the susceptibility of various test articles against test organisms. A modification of the National Committee Consensus on Laboratory (NCCL) Standardized Protocol "Methods for dilution antimicrobial susceptibility tests for bacteria that grow aerobically" was used in these studies. Sterile Phosphate Buffer Saline (PBS) at pH 7.0 (vehicle) was used as the diluent. Use of such diluent allows for the determination of the intrinsic activity of our test articles in the absence of any interfering molecules. Specifically, each test article was diluted using 2-fold serial dilution in 96-well plate to give a range of concentrations from approximately 50 mM to 0.05 mM in a final volume of 0.1 mL. Each dilution was inoculated with 5×105 CFU/mL test bacteria. The initial optical density as absorbance of each well was read at OD 550 nm using ThermoMax plate reader. After the initial OD reading co-incubation was carried out at 37° C. temperatures for up to 24 hour. At various time intervals post-treatment, OD reading at 550 nm was recorded at various time intervals. FIG. 1A and Table 1 show time dependent growth inhibition capability of analogs on *E. coli* at 12.5 mM.

TABLE 1

Growth Inhibition of E. coli by Methionine Analogs

| Absorbance | Concentration | Time (hrs) | | | | | | | | |
|---|---|---|---|---|---|---|---|---|---|---|
| | | 0 | 1 | 2 | 3 | 3.75 | 5 | 6.5 | 7.25 | 23 |
| M9 Control | NMF | 0.080 | 0.110 | 0.138 | 0.148 | 0.137 | 0.162 | 0.173 | 0.181 | 0.387 |
| Well 12 Methionine | 12.5 | 0.085 | 0.123 | 0.164 | 0.168 | 0.151 | 0.191 | 0.202 | 0.202 | 0.427 |
| Well 12 (I-AA) | 12.5 | 0.084 | 0.113 | 0.130 | 0.133 | 0.109 | 0.118 | 0.110 | 0.100 | 0.130 |
| Well 12 (I-AB) | 12.5 | 0.085 | 0.095 | 0.111 | 0.104 | 0.090 | 0.094 | 0.090 | 0.089 | 0.091 |

Figure 1B:
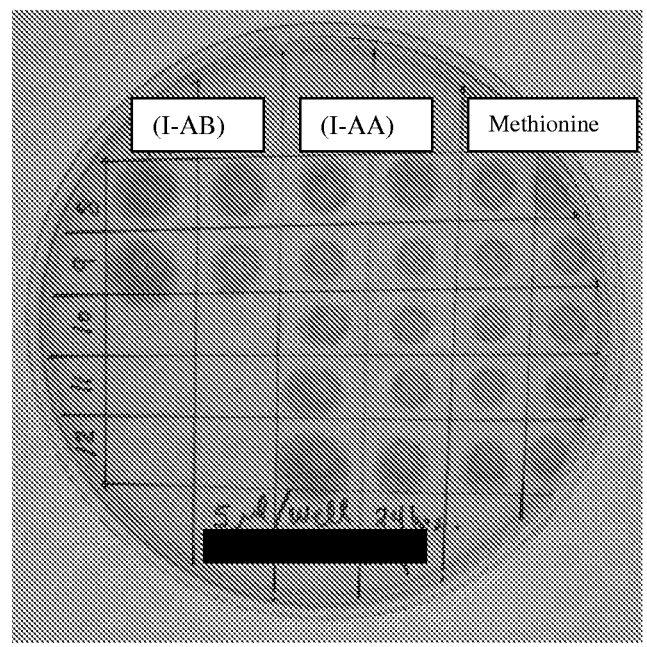
FIG. 1B depicts a gridded agar plate following incubation of samples from the *E. coli* bacterial growth inhibition experiments after 24 hrs.

MBC was determined by plating 5 µL of each sample onto a gridded agar plate (see, for example, FIG. 1B). Plates were then incubated overnight at 37° C., and examined for growth or no growth. The concentration at which there was a complete absence of colony growth was determined to be the MBC.

most bacteria were killed within 24 hours, as opposed to continuous growth of each species of test bacteria in M9 media (data not shown). These results show that the tested analogs eradicated test bacteria quickly (in less than 24 h) as opposed to un-inhibited growth of all bacteria in M9 media (data not shown).

TABLE 2

Broad Spectrum Bacterial Growth Inhibition Data

| Well | Conc. | Bacteria | | | | | |
|---|---|---|---|---|---|---|---|
| | | S. aureus | S. epidermids | Ps. sturtzeri | B. subtillus | E. coli | P. aeruginosa |
| 4 | 0.0 | 0.6 | 0.7 | 0.5 | 0.5 | 0.4 | 1.1 |
| 5 | 0.1 | 0.6 | 0.7 | 0.5 | 0.5 | 0.4 | 1.0 |
| 6 | 0.2 | 0.5 | 0.6 | 0.3 | 0.4 | 0.4 | 1.0 |
| 7 | 0.4 | 0.5 | 0.3 | 0.3 | 0.4 | 0.4 | 1.0 |
| 8 | 0.8 | 0.5 | 0.2 | 0.2 | 0.2 | 0.5 | 1.0 |
| 9 | 1.6 | 0.4 | 0.2 | 0.2 | 0.2 | 0.4 | 1.0 |
| 10 | 3.1 | 0.2 | 0.1 | 0.2 | 0.2 | 0.2 | 1.0 |
| 11 | 6.3 | 0.1 | 0.1 | 0.2 | 0.2 | 0.2 | 0.1 |
| 12 | 12.5 | 0.1 | 0.1 | 0.2 | 0.2 | 0.2 | 0.1 |

For FIGS. 1A and 1B, the 96-well plate format was used to culture E. coli (DH5-α) cells in M9 minimal media supplemented with glucose (M9) or same media supplemented with a range of concentrations of various analogs. Experiments were carried out in duplicate. E. coli growth was significantly inhibited by the I-AB analog as compared to M9 and other analogs. Bacterial growth inhibition was concentration-dependent by I-AB as seen in spot inoculated agar plate (FIG. 1B; absence of re-growth: spot inoculation from well 12, 11 and 10).

Example 7

Broad Spectrum Growth Inhibition by Methionine Analogs

Figure 2:
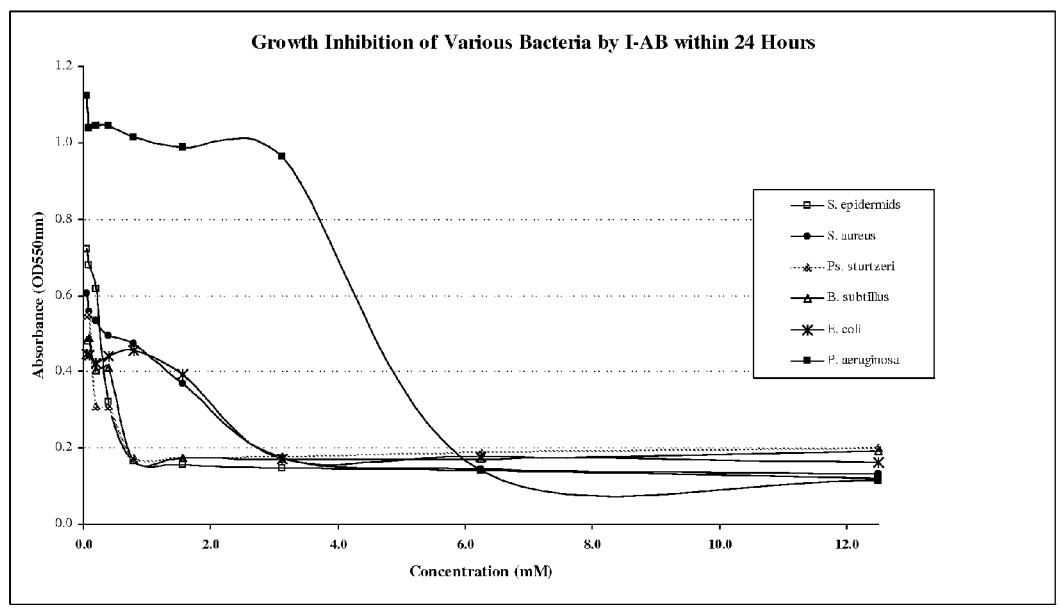
FIG. 2 depicts growth inhibition curves for various bacteria in the presence of methionine analog I-AB.

Preliminary in vitro studies demonstrate that the analogs possess antibacterial capabilities. Table 2 and FIG. 2 summarizes a series of studies, which were performed to test eradication of bacterial growth using various species (representative strains of gram positive and gram negative microorganisms commonly associated with wound infection). A 96-well plate format was used to culture different bacteria in M9 minimal media supplemented with glucose (M9) or same media supplemented with a range of concentrations of various analogues (Methionine, I-AA and I-AB). Experiments were carried out in duplicate. In these experiments bacterial growth inhibition was concentration-dependent by I-AB (as seen for E. coli in FIGS. 1A and 1B), and Example 8

Cytotoxicity Activity

Cytotoxicity is assessed by a colorimetric assay system (Sagripanti J-L, Bonifacino A. Cytotoxicity of Liquid Disinfectants. Surgical Infections, 2000; 1(1): 3-14, the content of which is hereby incorporated by reference, particularly with respect to the experimental methods described therein), using 3'-(phenylamino-carbonyl)-3,4-tetrazol-lium-bis(4-methoxy-6-nitro)benzene sulfonic acid hydrate (XTT), ProCheck™ cell viability assay (Evaluation of a soluble tetrazolium/formazan assay for cell growth and drug sensitivity in culture using human and other tumor cell lines described by Scudiero D A, Shoemaker R A H, Paul K D, Monks A, Tierney S, Nofziger T H, Currens M J, Seniff D, Boyd M R. Cancer Res. 1988 Sep. 1; 48(17):4827-33, the content of which is hereby incorporated by reference, particularly with respect to the experimental methods described therein). Similar approaches for determining the cell viability are used by other investigators. Three cell types are used: mouse lung epithelial cells (L929), primary human skin fibroblast and primary human keratinocyte cells cultured in Dulbecco Modified Eagle's Medium and Keratinocyte defined medium with corresponding growth factors plus antibiotics. Cells are trypsinized and counted under the microscope and seeded at 1000-to-2000 cells per well of a flat-bottom 96-well plate. Cells are allowed to grow overnight at 37° C. Tissue culture media is removed the following day and cells are rinsed with fresh media 1× and then left in 50 µL of tissue culture media. Test articles are prepared as 2-fold dilutions and 200 µL is added into each set of 4-wells (total volume per well is 250 µL). Cells are exposed to test articles for 60 min at room temperature. Immediately after the exposed time, test article from each well is removed and cells are fed with 250 µL of fresh media. Plates are incubated at 37° C. for 18-20 hr. The following day media is removed again and replaced with 100 µL/well of fresh media containing 10/100 µL XTT-reagent. Cells are incubated under growth conditions (5% $CO_2$ at 37° C. humidified incubator), protected from light, until color development is achieved. Absorbance is read at 450 nm with reference wavelength at 750 nm using Molecular Device ThermoMax Plate reader, blanking the plate on the medium-only assay blank wells. Untreated cells receiving XTT reagents-only serve as positive cell proliferation control.

Example 9

Cytotoxicity Activity for Methionine Analogs

Preliminary studies of cytotoxicity were performed in a mammalian cell viability assay. While different from the various types of cells found in skin, the CV-1 (African Green Monkey Kidney Cells) cells are as sensitive as L929 cells, and readily available, making them a suitable for initial cytotoxicity target cells.

CV-1 cells were propagated in DMEM plus 8% FBS according to supplier's recommendations. CV-1 cells were seeded at $1.5 \times 10^4$ cells per well in 96-well plates and incubated overnight at 37° C. On the day of testing, growth medium was aspirated from each well, and 20 µl fresh medium was added per well. Test articles were diluted from 50 mM to 0.05 mM by 2-fold serial dilution using PBS at pH 7.0 for each test article. After which 80 µl of each dilution was added to each well for a total volume of 100 µl per well. Following 60 minutes exposure at 37° C., test articles were aspirated and replaced with fresh 100 µl tissue culture media and incubated for 24 hours at 37° C. Next day cell culture media was removed and cell viability was determined by addition of WST-8 (Dojindo, Japan) reagent and the absorption at 450 nm read spectrophotometrically. Orange-red formazan, which is produced by live cells, is a direct measure of cell viability in this assay.

Figure 3:
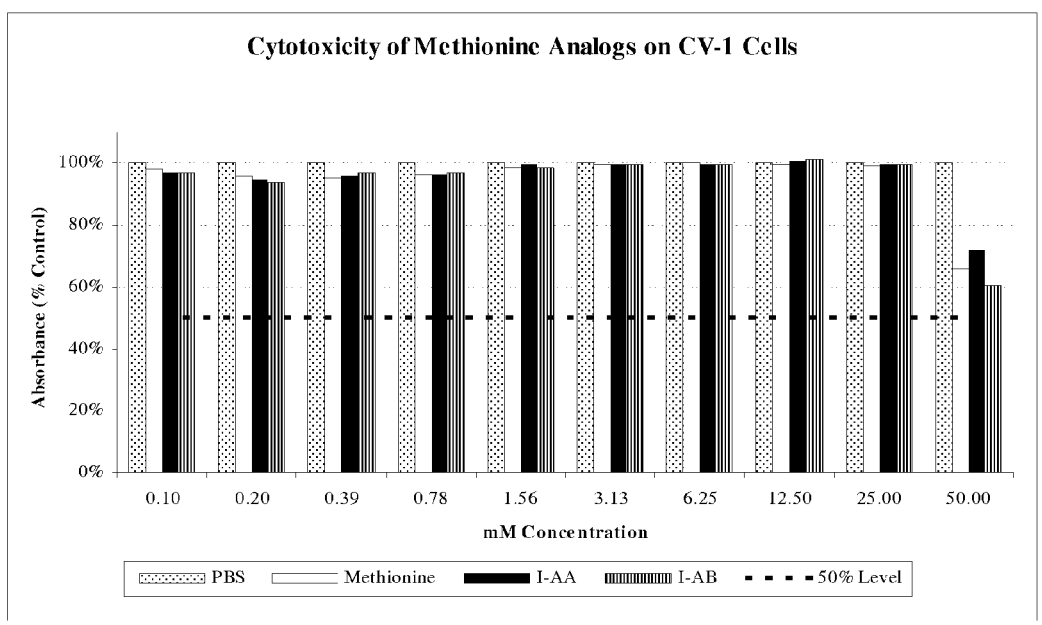
FIG. 3 depicts the cytotoxicity for methionine analogs with CV-1 cells.
Figure 4:
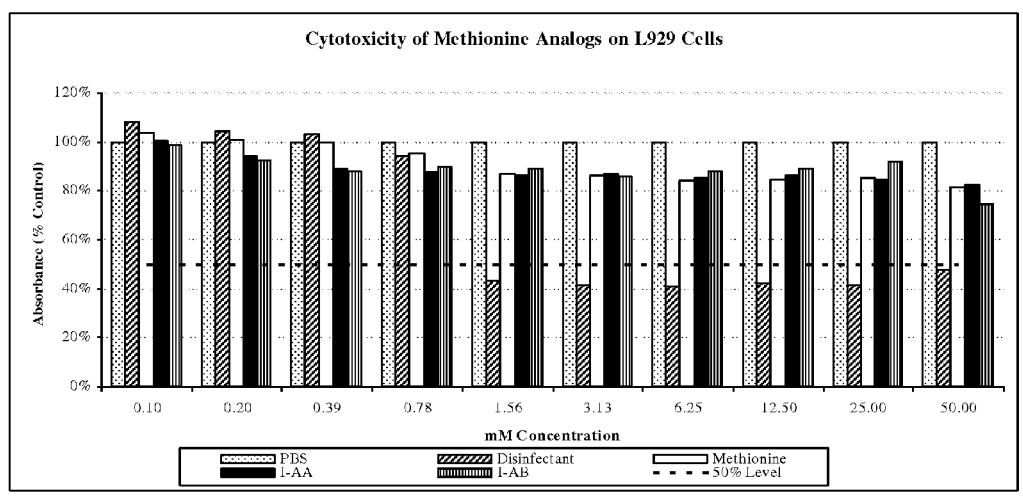
FIG. 4 depicts the cytotoxicity for methionine analogs with L929 cells.

Data for methionine analogs are shown in Table 3 and FIG. 3. The cytotoxicity of the tested analogs, at concentrations similar to those used in MBC assays is not toxic to CV-1 cells. At high concentrations (50 mM) cytotoxicity is observed in the cell viability assay. Results are expressed as percentage of cells surviving the treatment as compared to PBS. Cytotoxicity data for methionine analogs using L929 cells are shown in Table 4 and FIG. 4.

TABLE 3

Percentage of Surviving CV-1 cells for methionine analogs relative to PBS

| Well Number | 3 | 4 | 5 | 6 | 7 | 8 | 9 | 10 | 11 | 12 |
|---|---|---|---|---|---|---|---|---|---|---|
| Concentration (mM) | 0.1 | 0.2 | 0.39 | 0.78 | 1.56 | 3.13 | 6.25 | 12.5 | 25.0 | 50.0 |
| Methionine | 98% | 96% | 95% | 96% | 99% | 100% | 100% | 99% | 99% | 66% |
| I-AA | 97% | 95% | 96% | 96% | 100% | 100% | 99% | 101% | 99% | 72% |
| I-AB | 97% | 94% | 97% | 97% | 98% | 100% | 100% | 101% | 100% | 60% |

TABLE 4

Percentage of Surviving L929 cells for methionine analogs relative to control

| Well Number | 3 | 4 | 5 | 6 | 7 | 8 | 9 | 10 | 11 | 12 |
|---|---|---|---|---|---|---|---|---|---|---|
| Concentration (mM) | 0.1 | 0.2 | 0.39 | 0.78 | 1.56 | 3.13 | 6.25 | 12.5 | 25.0 | 50.0 |
| Methionine | 104% | 101% | 100% | 95% | 87% | 86% | 84% | 85% | 85% | 81% |
| I-AA | 100% | 94% | 89% | 87% | 87% | 87% | 85% | 86% | 85% | 82% |
| I-AB | 99% | 92% | 88% | 90% | 89% | 86% | 88% | 89% | 92% | 75% |
| Disinfectant* | 108% | 104% | 103% | 94% | 43% | 41% | 41% | 42% | 41% | 47% |

*0.6% bleach in PBS

Example 10

Enzymatic Aminoacylation tRNA Charging Assay

The assay system is as described by Hartman M et al, 2006 Enzymatic aminoacylation of tRNA with unnatural amino acids. *PNAS*. 103(12):4356-4361 (the content of which is hereby incorporated by reference, particularly with respect to the experimental methods described therein). Each assay contains 40 mM Hepes (pH 7.4), 17 mM $MgCl_2$, 45 mM KCl, 3.4 mM 2-mercaptoethanol, 6 mM ATP, 6% glycerol, 350 µM *E. coli* tRNA (Roche), 0.09 mg/mL BSA, 910 nM Methionyl-tRNA synthetase (MetRS) and amino acids in 100-1,000 µM range. The assay is initiated by addition of the mixture of AARS and incubated at 25-30° C. for 10 minutes. Samples are transferred to ice bath to stop the reactions and then small aliquot (2 µL) samples are precipitated using 500 µL of 5% cold TCA onto Whatmann filter papers and vacuumed and then dried under a heat lamp. Radioactivity of each sample is measured as counts per minute (CPM), as compared to controls (without the analog). Results for the S enantiomer of I-A ((S)-2-amino-4-(methylthio)butane-1-sulfonic acid hydrochloride) are shown below in Table 11.

TABLE 11

Pattern of *E. coli* Methionyl-tRNA synthetase inhibition for analog I-A

| Tube Number | Mix | I-A (mM) | Volume | $H_2O$ | Counts Per Minute 1 Minute | 10 Minutes |
|---|---|---|---|---|---|---|
| Experiment #1 | | | | | | |
| 6 | 15 ul | 0.00 | 0 | 5 | 2,564 | 3,735 |
| 5 | 15 ul | 0.04 | 5 | 0 | 2,476 | 3,466 |
| 4 | 15 ul | 0.20 | 5 | 0 | 2,333 | 3,147 |
| 3 | 15 ul | 1.00 | 5 | 0 | 2,372 | 3,218 |
| 2 | 15 ul | 5.00 | 5 | 5 | 2,007 | 2,891 |
| Experiment #2 | | | | | | |
| 1 | 15 ul | 0.00 | 0 | 5 | | 1,946 |
| 2 | 15 ul | 0.25 | 5 | 0 | | 1,701 |
| 3 | 15 ul | 1.25 | 5 | 0 | | 1,907 |
| 4 | 15 ul | 5.00 | 5 | 0 | | 1,575 |
| 5 | 15 ul | 12.5 | 5 | 0 | | 1,672 |

Example 12

Zone of Inhibition (Solid Support Assay)

Diameter of zone of inhibition is determined as described by Ames B. A, et al 1973. Ellicit Transport: The oligopeptide permease. *PNAS*. 70(2):456-458, the content of which is hereby incorporated by reference, particularly with respect to the experimental methods described therein. A 0.1 mL of a nutrient broth culture of each bacterial strain is spread as a lawn to the soft agar layer of a minimal medium Petri plate. Filter paper discs (6 mm) are placed on the inoculated plate and then 15 uL of different concentration ranges of each test article is placed on each disc. Incubation is carried at 37° C. overnight and diameter of each zone of inhibition (mm) is measured in by appropriate ruler. The efficacy of each test articles is compared to positive and negative control.

Example 13

Zone of Inhibition for Methionine Analogs

Figure 5:
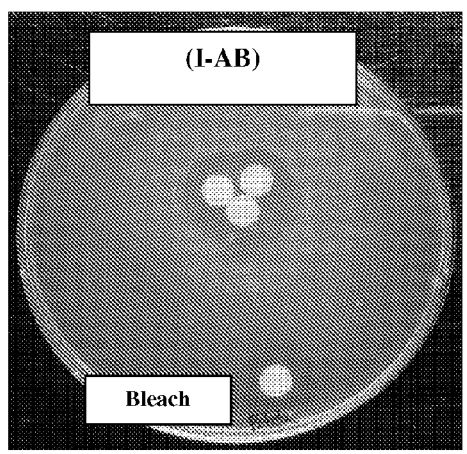
FIG. 5 depicts the results of *E. coli* zone of inhibition assays for methionine analogs.
Figure 5:
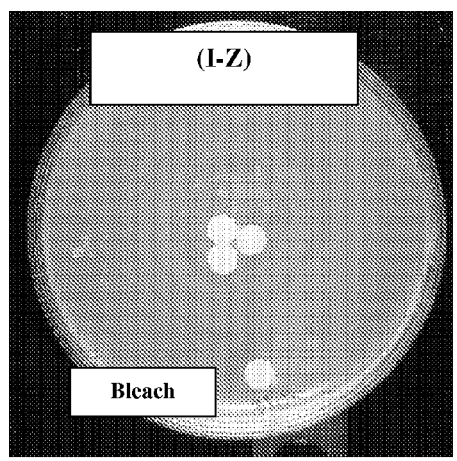

The Zone of Inhibition assay was prepared by mixing 3 g of powder (Difco nutrient agar) with 100 ml (3% w/v) of distilled water in a 250 mL flask, placing the flask in a boiling-water bath until the medium was clear. After sterilization (autoclaving) flask containing the melted agar was placed in a water bath at 56° C. to maintain a liquid state until poured. To prepare plates, 50 mL of melted agar was mixed with 50 mL (1:1 ratio) of Minimal media (called M9). To provide a layer which is uniformly about 5 mm deep, 20 ml of agar media was poured onto an assay plate (100 mm in diameter) and allowed to harden. For seed the cells, 100 µL of over night grown culture of *E. coli* cells are evenly spread over the agar surface using sterile spreader. To test the antimicrobial activity, sterile filter paper disks (5 mm in diameter) are aseptically placed on designated spots and then each disk is impregnated with 10 µL of 15.6 mM test analogs (I-Z or I-AB) or control solutions (10 µL of 0.06% diluted bleach in PBS). Plates are allowed to incubate at 37° C. for 24-to-48 hours until zone of inhibition is observed. The zone of inhibition in this assay is directly proportional to the strength of antimicrobial agent. Results for analog I-Z and I-AB are shown in FIG. 5.

Example 13

Bacterial Growth Inhibition (Liquid Assay)

This assay is performed as described by Cascieri, T and M. F. Mallette 1974. New method for study of peptide transport in bacteria. Applied Microbiology, 27(3): 457-463, the content of which is hereby incorporated by reference, particularly with respect to the experimental methods described therein. A 1 mL of test bacterial cells grown overnight is inoculated into 100 mL of fresh minimal media containing the following materials in grams per litter of distilled water: 8 g of $Na_2HPO_4.12H_2O$, 10.0 g of $KH_2PO_4$, 1.0 g of $NH_4Cl$, 0.5 g of NaCl, 0.41 g $MgSO_4.7H_2O$, 20.0 g glucose. Cells were incubated in 37° C. shaker and growth curves are determined from turbidity (optical density) at 650 nm over hourly intervals for total of 6-12 hr. The efficacy of each test articles is compared to positive and negative control.

Example 14

Wound Healing of Methionine Analogs

Established rat chronic granulating wound models may be utilized to test for topical wounds treatment therapy. Chronic granulating wounds are prepared as previously described (Robson et al. Hypochlorous acid as a potential wound care agent. *J of Burns and Wounds*. 2007. Apr. 11; 80-90. Robson et al. The efficacy of systemic antibiotics in the treatment of granulating wounds. *J. Surg Res*. 1974; 16:299-3006). Male Sprague-Dawley rats weighing 300-350 grams are acclimated in the facility for a week prior to use. Under intraperitoneal Nembutal anesthesia (35 mg/kg), the rat dorsum is shaved and depilated. A full thickness dorsal burn measuring 30 $cm^2$ is created by immersion in boiling water. Infected groups are seeded with $5 \times 10^9$ CFU *Escherichia coli* (ATCC 25922) after animals have been allowed to cool for 15 min. Animals are individually caged and given food and water ad libitum. Uninfected, control animals are kept in a physically separate facility. Five days after burning, the eschar is excised from anesthetized animals resulting in a chronic granulating wound. Histological characterization of the wound with comparison to a human granulating wound is done. All experiments are conducted in accordance with the AALAC Guidelines, and IAACUC at TOXiKON (Bedford, Mass.).

Treatment Groups: 24 rats are divided into 6 groups of 3-5 animals each. The groups are treated as shown in Table 12.

TABLE 12

Rat Treatment Groups for Wound Healing Study.

| Group | Treatment Option | Animals Per Group |
|---|---|---|
| I | Uninfected | 3 |
| II | Infected/Normal Saline | 3 |
| III | Infected/Methionine Analog (low dose) changed q24 hrs | 5 |
| IV | Infected/Methionine Analog (mid dose) changed q24 hrs | 5 |
| V | Infected/Methionine Analog (high dose) changed q24 hrs | 5 |
| VI | Infected/Silvadene changed q24 hrs | 3 |

Animal Procedures: In these experiments, rats are premedicated with buprenorphine (0.1 mg/kg) and anesthetized with halothane inhalation on post-escharectomy days 4, 8, 12, 16 and 20. Any dried exudates that formed are atraumatically removed. Wounds are biopsied for quantitative bacteriology on the day of escharectomy (day 0) and on each of the days of re-anesthesia according to the methods described by Heggers and Robson (Heggers J P, Robson M C. *Quantitative Bacteriology: Its role in the armamentarium of the surgeon*. Boca Raton, Fla.: CRC; 1991.). The wound surface is cleaned with 70% isopropyl alcohol prior to biopsy to exclude surface contamination. Biopsies are aseptically weighed, homogenized, serially diluted, and back plated onto non-selective media. Bacterial counts are completed after 48 hours incubation and expressed as colony forming units (CFU) per gram of tissue.

While the rats are anesthetized for the wound biopsies, outlines of the of the wounds are traced onto acetate sheets, and area calculations are performed using computerized digital planimetry (Sigma Scan Jandel Scientific, Corte Madera, Calif.). Care is taken only to record the perimeter of the wound that represents the advancing full-thickness margin rather than the edge of any advancing epithelium. This avoids the small component of advancement provided by the smooth, pink translucent, hairless neoepithelium (Kuhn et al. Basic fibroblast growth factor in a carboxymethylcellulose vehicle reverses the bacterial retardation of wound contraction. *Wounds*. 2001; 13:73-80). All animals are weighed at the time of biopsy and wound measurement. The animals are sacrificed by Nembutal overdose and bilateral Thoracotomies when the wound has completely healed or decreased to less than 10 percent of its original area. Hayward et al demonstrated that measurement of very small wounds by manual tracing introduced significant systematic error and found that wounds followed past this point remained static for prolonged periods of time (Hayward et al. Fibroblast growth factor reverses the bacterial retardation of wound contraction. *Am. J. Surg.* 1992; 288-293).

Statistical Analysis. Mean bacterial counts for each group of animals in both experiments are determined and expressed a CFU/gram of tissue. These values are compared for each experiment separately using a one-way analysis of variance. Post-hoc analyses of differences between groups are carried out using Tukey's Test (all pairs, multiple-comparison test) with $p<0.05$ considered significant. Sigma Stat statistical software (Jandel Scientific, Corte Madera, Calif.) is used for data analysis.

Serial wound area measurements are plotted against time. For each animal's data a Gompertz equation is fitted (typical $r2=0.85$) (18). Using this approach a best fit curve is generated for each group. Comparison between groups is performed using life table analyses and the Wilcoxon rank test. These statistical analyses are performed using SAS (SAS/STAT Guide for Personal Computers, Version 6 edition, Cary, N.C., 1987, p 1028) and BMDP (BMDP Statistical Software Manual, Los Angeles, BMDP Statistical Software, Inc. 1988) package on a personal computer.

Example 15

In Vitro Protein Translation Inhibition

Prokaryotic Cell-Free Translation Systems or Rabbit Reticulocyte Lysate Translation Systems (RRLTS) may be used in to study the properties of the methionine compounds as inhibitors of protein translation. These in vitro systems play an important role in characterization of mRNA translation products, investigation of transcriptional and translational control, and co-translational processing of secreted proteins by the addition of microsomal membranes to the translation reaction. Rabbit Reticulocyte Lysate is prepared from New Zealand white rabbits injected with phenylhydrazine using a standard protocol to increase reticulocyte production (Pelham and Jackson, 1976). The reticulocytes are harvested, and any contaminating cells that could otherwise alter the translational properties of the final extract are removed. After lysis of the reticulocytes, the extract is treated with micrococcal nuclease to digest endogenous mRNA and thus reduce background translation to a minimum. The lysate contains the cellular components necessary for protein synthesis: tRNA, ribosomes, amino acids, and initiation, elongation and termination factors. Rabbit reticulocyte lysate has been reported to contain a variety of post-translational processing activities, including acetylation, isoprenylation, proteolysis and some phosphorylation activity (Glass and Pollard, 1990). Processing events such as signal peptide cleavage and core glycosylation can be examined by adding canine microsomal membranes to a translation reaction (Andrews, 1987; Walter and Blobel, 1983; Thompson and Beckler, 1992)

General guideline for setting up of an in vitro translation reaction: The reaction uses [35S]methionine as the radiolabel; other isotopes may also be used. For the positive control reaction, one can use 1-2 µl of the Luciferase Control RNA. The reaction components shown in Table 13 are then set up in a 0.5 mL or 1.5 mL tube. A negative control is also prepared containing no added template to allow measurement of background incorporation of labeled amino acids. The translation reaction is incubated at 30° C. for 60-90 minutes. The results of translation are analyzed by gel electrophoresis and autoradiography.

TABLE 13

Rat Treatment Groups for Wound Healing Study.

| Component | Volume |
|---|---|
| Flexi ® Rabbit Reticulocyte Lysate | 33 µl |
| Amino Acid Mixture Minus Methionine (plus various BXP analogs), 1 mM | 1 µl |
| [35S]methionine (1,200 Ci/mmol at 10 mCi/ml) | 2 µl |
| Magnesium Acetate, 25 mM | 0-4 µl |
| Potassium Chloride, 2.5M | 1.4 µl |
| DTT, 100 mM | 0-1 µl |
| RNasin ® Ribonuclease Inhibitor (40 u/ml) | 1 µl |
| RNA substrate | 1-12 µl |
| Nuclease-Free Water to final volume | 50 µl |

What is claimed is:

1. A compound of the formula:

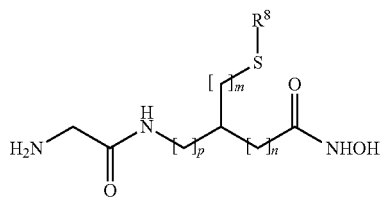

wherein
$R^8$ is hydrogen or alkyl; and
m, n, and p are independently 0, 1, 2, 3, or 4;
or a pharmaceutically acceptable salt thereof or solvate of the foregoing.

2. The compound of claim 1, wherein m is 1, 2, or 3, n is 0, 1, or 2, and p is 0, 1, or 2.

3. The compound of claim 2, wherein m is 2, n is 0, and p is 0.

4. The compound of claim 1, wherein $R^8$ is alkyl.

5. The compound of claim 4, wherein $R^8$ is methyl.

6. The compound of claim 1, wherein the compound is

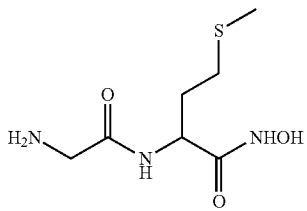

or a pharmaceutically acceptable salt thereof or solvate of the foregoing.

7. A formulation comprising a compound of claim 1 and a pharmaceutically acceptable carrier.

8. A method of treating a bacterial infection in an individual, comprising administering to the individual an effective amount of a compound of claim 1, wherein the bacterial infection is caused by S. epidermids, S. aureus, Ps. sturtzeri, B. subtillus, E. coli, or P. aeruginosa.

9. The method of claim 8, wherein the bacterial infection is caused by E. coli or S. aureus.

10. A method of inhibiting the growth of a microorganism, comprising contacting the microorganism with an effective amount of a compound of claim 1, wherein the microorganism is S. epidermids, S. aureus, Ps. sturtzeri, B. subtillus, E. coli, or P. aeruginosa.

11. The method of claim 10, wherein the microorganism is E. coli or S. aureus.

12. The compound of claim 1, wherein m is 1, 2, 3, or 4, n is 0, and p is 0.

* * * * *